US012398198B2

(12) United States Patent
Zhan et al.

(10) Patent No.: US 12,398,198 B2
(45) Date of Patent: Aug. 26, 2025

(54) PARVOVIRUS ANTIBODIES FOR VETERINARY USE

(71) Applicant: Elanco US Inc., Greenfield, IN (US)

(72) Inventors: Hangjun Zhan, Foster City, CA (US); Lam Nguyen, Union City, CA (US); Ellen Ratcliff, Burlingame, CA (US); Richard Chin, San Francisco, CA (US); Shyr Jiann Li, Millbrae, CA (US)

(73) Assignee: Elanco US Inc., Greenfield, IN (US)

( * ) Notice: Subject to any disclaimer, the term of this patent is extended or adjusted under 35 U.S.C. 154(b) by 880 days.

(21) Appl. No.: 17/630,685

(22) PCT Filed: Jul. 30, 2020

(86) PCT No.: PCT/US2020/044302
§ 371 (c)(1),
(2) Date: Jan. 27, 2022

(87) PCT Pub. No.: WO2021/022067
PCT Pub. Date: Feb. 4, 2021

(65) Prior Publication Data
US 2022/0267414 A1 Aug. 25, 2022

Related U.S. Application Data

(60) Provisional application No. 63/030,123, filed on May 26, 2020, provisional application No. 62/968,970, filed on Jan. 31, 2020, provisional application No. 62/880,650, filed on Jul. 30, 2019.

(51) Int. Cl.
*C07K 16/08* (2006.01)
*A61P 31/20* (2006.01)

(52) U.S. Cl.
CPC ............ *C07K 16/081* (2013.01); *A61P 31/20* (2018.01); *C07K 2317/24* (2013.01); *C07K 2317/515* (2013.01); *C07K 2317/52* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,063,905 A | 5/2000 | Capra et al. | |
| 6,372,426 B1 | 4/2002 | Zens | |
| 7,604,801 B2 | 10/2009 | Smith-Norowitz et al. | |
| 8,052,971 B2 | 11/2011 | Meyer | |
| 8,512,981 B2 | 8/2013 | Hermens et al. | |
| 8,790,651 B2 | 7/2014 | Bammert et al. | |
| 8,828,400 B2 | 9/2014 | Leuchs et al. | |
| 9,556,261 B2 | 1/2017 | Gnauer et al. | |
| 10,080,798 B2 | 9/2018 | David et al. | |
| 10,092,647 B2 | 10/2018 | Feugier et al. | |
| 2007/0248612 A1 | 10/2007 | Wilson | |
| 2009/0162831 A1 | 6/2009 | Delwart et al. | |
| 2014/0044713 A1 | 2/2014 | Lau et al. | |
| 2014/0170187 A1 | 6/2014 | Settembre et al. | |
| 2015/0086558 A1 | 3/2015 | Chang et al. | |
| 2016/0046723 A1 | 2/2016 | Reyes et al. | |
| 2016/0213778 A1 | 7/2016 | Feugier et al. | |
| 2017/0158756 A1 | 6/2017 | Bergeron et al. | |
| 2018/0009869 A1 | 1/2018 | Lu et al. | |

FOREIGN PATENT DOCUMENTS

| | | |
|---|---|---|
| EP | 914831 B1 | 4/2003 |
| EP | 1009756 B1 | 9/2004 |
| EP | 2384761 B1 | 9/2013 |
| EP | 2332986 B1 | 10/2013 |
| EP | 2566491 B1 | 7/2015 |
| EP | 2736921 B1 | 6/2018 |
| EP | 3019524 B1 | 4/2020 |
| JP | 2005006583 A | 1/2005 |
| WO | 2004105792 A1 | 12/2004 |
| WO | 2012164372 A1 | 12/2012 |
| WO | 2016210097 A1 | 12/2016 |
| WO | 2018/102795 A2 | 6/2018 |
| WO | 2019035010 A1 | 2/2019 |
| WO | 2020256419 A1 | 12/2020 |
| WO | 2021022067 A2 | 2/2021 |

OTHER PUBLICATIONS

Hafenstein, S, et al., "Structural Comparison of Different Antibodies Interacting with Parvovirus Capsids", Journal of Virology, Jun. 2009, 83(11): 5556-5566.
Salazar G, et al., "Antibody therapies for the prevention and treatment of viral infections", npj Vaccines, Jul. 10, 2017, 2:19; doi:10.1038/s41541-017-0019-3 (12 pages).
Carmichael, L.E., et al., "A Modified Live Canine Parvovirus Vaccine. II. Immune Response", Cornell Vet., 1983, 73: 13-29.
Nelson, C.D.S., et al., "Different mechanisms of antibody-mediated neutralization of parvoviruses revealed using the Fab fragments of monoclonal antibodies", Virology, May 1, 20070; 361(2): 283-293 (NIH Public Access Author Manuscript, 23 pages).
Extended European Search Report issued in corresponding European Patent Application No. 20847060.9 (9 pages), dated May 25, 2023.

(Continued)

*Primary Examiner* — Phuong Huynh
(74) *Attorney, Agent, or Firm* — McBee, Moore & Vanik IP, LLC

(57) ABSTRACT

Provided are various embodiments relating to parvovirus antibodies, including caninized, felinized, and chimeric antibodies, that bind to canine and/or feline parvovirus, for example, having improved expression characteristics. In various embodiments, the parvovirus antibodies have ADCC, ADCP, and/or CDC effector functions. In various embodiments, such monoclonal parvovirus antibodies can be used in methods to prevent and/or treat parvoviral infection in subjects, such as dogs and cats. For example, the parvovirus antibodies provided may be used to provide passive immunity against infection with a canine or feline parvovirus.

28 Claims, 7 Drawing Sheets
Specification includes a Sequence Listing.

(56) References Cited

OTHER PUBLICATIONS

Ayyar, et al., "Optimizing antibody expression: The nuts and bolts," Methods, 116:51-62 (2017).
Li, et al., "Antibody Aggregation: Insights from Sequence and Structure," Antibodies, 5(19) doi: 10.3390/antib5030019 (2016).
International Search Report and Written Opinion received in PCT/US2020/044302, dated Dec. 17, 2020, 15 pages.

Fig. 3C

SEQUENCE LISTING

<160> NUMBER OF SEQ ID NOS: 99

<210> SEQ ID NO 1
<211> LENGTH: 38
<212> TYPE: PRT
<213> ORGANISM: Artificial Sequence
<220> FEATURE:
<223> OTHER INFORMATION: Synthetic: Epitope 1

<400> SEQUENCE: 1

Glu Ser Glu Asn Tyr Arg Arg Val Val Asn Asn Met Asp Lys Thr
1               5                   10                  15

Ala Val Asn Gly Asn Met Ala Leu Asp Asp Ile His Ala Glu Ile Val
            20                  25                  30

Thr Pro Trp Ser Leu Val
        35

<210> SEQ ID NO 2
<211> LENGTH: 44
<212> TYPE: PRT
<213> ORGANISM: Artificial Sequence
<220> FEATURE:
<223> OTHER INFORMATION: Synthetic: Epitope 2

<400> SEQUENCE: 2

Thr Pro Trp Arg Tyr Tyr Phe Gln Trp Asp Arg Thr Leu Ile Pro Ser
1               5                   10                  15

His Thr Gly Thr Ser Gly Thr Pro Thr Asn Ile Tyr His Gly Thr Asp
            20                  25                  30

Pro Asp Asp Val Gln Phe Tyr Thr Ile Glu Asn Ser
        35                  40

<210> SEQ ID NO 3
<211> LENGTH: 24
<212> TYPE: PRT
<213> ORGANISM: Artificial Sequence
<220> FEATURE:
<223> OTHER INFORMATION: Synthetic: Minimal epitope 2

<400> SEQUENCE: 3

Thr Pro Trp Arg Tyr Tyr Phe Gln Trp Asp Arg Thr Leu Ile Pro Ser
1               5                   10                  15

His Thr Gly Thr Ser Gly Thr Pro
            20

<210> SEQ ID NO 4
<211> LENGTH: 10
<212> TYPE: PRT
<213> ORGANISM: Artificial Sequence
<220> FEATURE:
<223> OTHER INFORMATION: Synthetic: Variable heavy chain CDRH1 of Mab A

<400> SEQUENCE: 4

Gly Phe Ser Leu Ser Ser Tyr His Val His
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic: Variable heavy chain CDRH2 of Mab A

<400> SEQUENCE: 5

```
Val Met Trp Asn Asp Gly Asp Thr Ser
1               5

<210> SEQ ID NO 6
<211> LENGTH: 14
<212> TYPE: PRT
<213> ORGANISM: Artificial Sequence
<220> FEATURE:
<223> OTHER INFORMATION: Synthetic: Variable heavy chain CDRH3 of Mab A

<400> SEQUENCE: 6

Pro Glu Leu Pro Gly Leu Thr Tyr Gly Val Trp Phe Pro Tyr
1               5                   10

<210> SEQ ID NO 7
<211> LENGTH: 25
<212> TYPE: PRT
<213> ORGANISM: Artificial Sequence
<220> FEATURE:
<223> OTHER INFORMATION: Synthetic: Variable heavy chain framework
      region HC-FR1 of Mab A

<400> SEQUENCE: 7

Gln Val Gln Leu Lys Glu Ser Gly Pro Gly Leu Val Gln Pro Ser Gln
1               5                   10                  15

Thr Leu Ser Leu Thr Cys Thr Val Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic: Variable heavy chain framework
      region HC-FR1 of Mab A variant 2 (v2), Q13A

<400> SEQUENCE: 8

Gln Val Gln Leu Lys Glu Ser Gly Pro Gly Leu Val Ala Pro Ser Gln
1               5                   10                  15

Thr Leu Ser Leu Thr Cys Thr Val Ser
            20                  25

<210> SEQ ID NO 9
<211> LENGTH: 14
<212> TYPE: PRT
<213> ORGANISM: Artificial Sequence
<220> FEATURE:
<223> OTHER INFORMATION: Synthetic: Variable region heavy chain
      framework region HC-FR2 of Mab A

<400> SEQUENCE: 9

Trp Val Arg Gln Pro Pro Gly Lys Gly Leu Glu Trp Leu Gly
1               5                   10

<210> SEQ ID NO 10
<211> LENGTH: 39
<212> TYPE: PRT
<213> ORGANISM: Artificial Sequence
<220> FEATURE:
<223> OTHER INFORMATION: Synthetic: Variable heavy chain framework
      region HC-FR3 of Mab A

<400> SEQUENCE: 10

Tyr Asn Leu Ala Leu Asn Ser Arg Leu Ser Ile Ser Arg Asp Thr Ser
1               5                   10                  15

Lys Ser Gln Val Phe Phe Lys Met Ser Ser Leu Gln Thr Glu Asp Thr
```

```
                20                  25                  30
Ala Thr Tyr Tyr Cys Ala Arg
        35

<210> SEQ ID NO 11
<211> LENGTH: 11
<212> TYPE: PRT
<213> ORGANISM: Artificial Sequence
<220> FEATURE:
<223> OTHER INFORMATION: Synthetic: Variable heavy chain framework
      region HC-FR4 of Mab A

<400> SEQUENCE: 11

Trp Gly Gln Gly Thr Leu Val Thr Val Ser Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic: Variable heavy chain framework
      region HC-FR4 of Mab A variant 2 (v2), S11A

<400> SEQUENCE: 12

Trp Gly Gln Gly Thr Leu Val Thr Val Ser Ala
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic: Variable light chain CDRL1 of Mab A

<400> SEQUENCE: 13

Lys Ala Ser Gln Asn Val Asp Ser Asn Val Asp
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic: Variable light chain CDRL2 of Mab A

<400> SEQUENCE: 14

Lys Ala Ser Asn Arg Asn Thr
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic: Variable light chain CDRL3 of Mab A

<400> SEQUENCE: 15

Met Gln Ser Thr Ser Tyr Pro Leu Thr Phe
1               5                   10

<210> SEQ ID NO 16
<211> LENGTH: 23
<212> TYPE: PRT
<213> ORGANISM: Artificial Sequence
<220> FEATURE:
<223> OTHER INFORMATION: Synthetic: Variable light chain framework
``` region LC-FR1 of Mab A

<400> SEQUENCE: 16

Asp Ile Val Met Thr Gln Thr Pro Ala Ser Met Ser Ile Ser Val Gly
1               5                   10                  15

Asp Arg Val Thr Met Asn Cys
            20

<210> SEQ ID NO 17
<211> LENGTH: 15
<212> TYPE: PRT
<213> ORGANISM: Artificial Sequence
<220> FEATURE:
<223> OTHER INFORMATION: Synthetic: Variable light chain framework
      region LC-FR2 of Mab A

<400> SEQUENCE: 17

Trp Tyr Gln Gln Lys Thr Gly Gln Ser Pro Asn Leu Leu Ile Tyr
1               5                   10                  15

<210> SEQ ID NO 18
<211> LENGTH: 32
<212> TYPE: PRT
<213> ORGANISM: Artificial Sequence
<220> FEATURE:
<223> OTHER INFORMATION: Synthetic: Variable light chain framework
      region LC-FR3 of Mab A

<400> SEQUENCE: 18

Gly Val Pro Asp Arg Phe Thr Gly Ser Gly Ser Gly Thr Asp Phe Thr
1               5                   10                  15

Phe Thr Ile Ser Asn Met Gln Ala Glu Asp Leu Ala Val Tyr Tyr Cys
            20                  25                  30

<210> SEQ ID NO 19
<211> LENGTH: 9
<212> TYPE: PRT
<213> ORGANISM: Artificial Sequence
<220> FEATURE:
<223> OTHER INFORMATION: Synthetic: Variable light chain framework
      region LC-FR4 of Mab A

<400> SEQUENCE: 19

Gly Ser Gly Thr Lys Leu Glu Ile Lys
1               5

<210> SEQ ID NO 20
<211> LENGTH: 122
<212> TYPE: PRT
<213> ORGANISM: Artificial Sequence
<220> FEATURE:
<223> OTHER INFORMATION: Synthetic: Variable heavy chain of Mab A, (Mab
      A HC)

<400> SEQUENCE: 20

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Ser Ser Tyr
            20                  25                  30

His Val His Trp Val Arg Gln Pro Pro Gly Lys Gly Leu Glu Trp Leu
                35                  40                  45

Gly Val Met Trp Asn Asp Gly Asp Thr Ser Tyr Asn Leu Ala Leu Asn
        50                  55                  60

Ser Arg Leu Ser Ile Ser Arg Asp Thr Ser Lys Ser Gln Val Phe Phe

```
                65                  70                  75                  80
Lys Met Ser Ser Leu Gln Thr Glu Asp Thr Ala Thr Tyr Tyr Cys Ala
                    85                  90                  95

Arg Pro Glu Leu Pro Gly Leu Thr Tyr Gly Val Trp Phe Pro Tyr Trp
                100                 105                 110

Gly Gln Gly Thr Leu Val Thr Val Ser Ser
            115                 120

<210> SEQ ID NO 21
<211> LENGTH: 122
<212> TYPE: PRT
<213> ORGANISM: Artificial Sequence
<220> FEATURE:
<223> OTHER INFORMATION: Synthetic: Variable heavy chain of Mab A
      variant 2, HC-FR1 Q13A, HC-FR4 S11A, (Mab A HC v2)

<400> SEQUENCE: 21

Gln Val Gln Leu Lys Glu Ser Gly Pro Gly Leu Val Ala Pro Ser Gln
1               5                   10                  15

Thr Leu Ser Leu Thr Cys Thr Val Ser Gly Phe Ser Leu Ser Ser Tyr
                20                  25                  30

His Val His Trp Val Arg Gln Pro Pro Gly Lys Gly Leu Glu Trp Leu
            35                  40                  45

Gly Val Met Trp Asn Asp Gly Asp Thr Ser Tyr Asn Leu Ala Leu Asn
        50                  55                  60

Ser Arg Leu Ser Ile Ser Arg Asp Thr Ser Lys Ser Gln Val Phe Phe
65                  70                  75                  80

Lys Met Ser Ser Leu Gln Thr Glu Asp Thr Ala Thr Tyr Tyr Cys Ala
                    85                  90                  95

Arg Pro Glu Leu Pro Gly Leu Thr Tyr Gly Val Trp Phe Pro Tyr Trp
                100                 105                 110

Gly Gln Gly Thr Leu Val Thr Val Ser Ala
            115                 120

<210> SEQ ID NO 22
<211> LENGTH: 107
<212> TYPE: PRT
<213> ORGANISM: Artificial Sequence
<220> FEATURE:
<223> OTHER INFORMATION: Synthetic: Variable light chain of Mab A, (Mab
      A LC)

<400> SEQUENCE: 22

Asp Ile Val Met Thr Gln Thr Pro Ala Ser Met Ser Ile Ser Val Gly
1               5                   10                  15

Asp Arg Val Thr Met Asn Cys Lys Ala Ser Gln Asn Val Asp Ser Asn
                20                  25                  30

Val Asp Trp Tyr Gln Gln Lys Thr Gly Gln Ser Pro Asn Leu Leu Ile
            35                  40                  45

Tyr Lys Ala Ser Asn Arg Asn Thr Gly Val Pro Asp Arg Phe Thr Gly
        50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Thr Ser Tyr Pro Leu
                    85                  90                  95

Thr Phe Gly Ser Gly Thr Lys Leu Glu Ile Lys
                100                 105
```

-continued

```
<210> SEQ ID NO 23
<211> LENGTH: 457
<212> TYPE: PRT
<213> ORGANISM: Artificial Sequence
<220> FEATURE:
<223> OTHER INFORMATION: Synthetic: Chimeric variable heavy chain of Mab
      A and canine IgG-B , (Chimeric A HC IgG-B)

<400> SEQUENCE: 23
```

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Ser Ser Tyr
            20                  25                  30

His Val His Trp Val Arg Gln Pro Pro Gly Lys Gly Leu Glu Trp Leu
        35                  40                  45

Gly Val Met Trp Asn Asp Gly Asp Thr Ser Tyr Asn Leu Ala Leu Asn
    50                  55                  60

Ser Arg Leu Ser Ile Ser Arg Asp Thr Ser Lys Ser Gln Val Phe Phe
65                  70                  75                  80

Lys Met Ser Ser Leu Gln Thr Glu Asp Thr Ala Thr Tyr Tyr Cys Ala
                85                  90                  95

Arg Pro Glu Leu Pro Gly Leu Thr Tyr Gly Val Trp Phe Pro Tyr Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
    210                 215                 220

Asn Gly Arg Val Pro Arg Pro Pro Asp Cys Pro Lys Cys Pro Ala Pro
225                 230                 235                 240

Glu Met Leu Gly Gly Pro Ser Val Phe Ile Phe Pro Pro Lys Pro Lys
                245                 250                 255

Asp Thr Leu Leu Ile Ala Arg Thr Pro Glu Val Thr Cys Val Val Val
            260                 265                 270

Asp Leu Asp Pro Glu Asp Pro Glu Val Gln Ile Ser Trp Phe Val Asp
        275                 280                 285

Gly Lys Gln Met Gln Thr Ala Lys Thr Gln Pro Arg Glu Glu Gln Phe
    290                 295                 300

Asn Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
        355                 360                 365

```
Asn Thr Val Ser Leu Thr Cys Leu Ile Lys Asp Phe Pro Pro Asp
    370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
                405                 410                 415

Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
        435                 440                 445

Glu Ser Leu Ser His Ser Pro Gly Lys
450                 455
```

<210> SEQ ID NO 24
<211> LENGTH: 457
<212> TYPE: PRT
<213> ORGANISM: Artificial Sequence
<220> FEATURE:
<223> OTHER INFORMATION: Synthetic: Chimeric variable heavy chain of Mab
    A v2 and canine IgG-B , HC-FR1 Q13A, HC-FR4 S11A, (Chimeric A HC
    v2 IgG-B),

<400> SEQUENCE: 24

```
Gln Val Gln Leu Lys Glu Ser Gly Pro Gly Leu Val Ala Pro Ser Gln
1               5                   10                  15

Thr Leu Ser Leu Thr Cys Thr Val Ser Gly Phe Ser Leu Ser Ser Tyr
            20                  25                  30

His Val His Trp Val Arg Gln Pro Pro Gly Lys Gly Leu Glu Trp Leu
        35                  40                  45

Gly Val Met Trp Asn Asp Gly Asp Thr Ser Tyr Asn Leu Ala Leu Asn
    50                  55                  60

Ser Arg Leu Ser Ile Ser Arg Asp Thr Ser Lys Ser Gln Val Phe Phe
65                  70                  75                  80

Lys Met Ser Ser Leu Gln Thr Glu Asp Thr Ala Thr Tyr Tyr Cys Ala
                85                  90                  95

Arg Pro Glu Leu Pro Gly Leu Thr Tyr Gly Val Trp Phe Pro Tyr Trp
            100                 105                 110

Gly Gln Gly Thr Leu Val Thr Val Ser Ala Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
    210                 215                 220

Asn Gly Arg Val Pro Arg Pro Pro Asp Cys Pro Lys Cys Pro Ala Pro
225                 230                 235                 240

Glu Met Leu Gly Gly Pro Ser Val Phe Ile Phe Pro Pro Lys Pro Lys
                245                 250                 255

Asp Thr Leu Leu Ile Ala Arg Thr Pro Glu Val Thr Cys Val Val Val
```

```
                   260                 265                 270
Asp Leu Asp Pro Glu Asp Pro Val Gln Ile Ser Trp Phe Val Asp
            275                 280                 285

Gly Lys Gln Met Gln Thr Ala Lys Thr Gln Pro Arg Glu Glu Gln Phe
        290                 295                 300

Asn Gly Thr Tyr Arg Val Ser Val Leu Pro Ile Gly His Gln Asp
            305                 310             315             320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
        355                 360                 365

Asn Thr Val Ser Leu Thr Cys Leu Ile Lys Asp Phe Phe Pro Pro Asp
            370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
                405                 410                 415

Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
                435                 440                 445

Glu Ser Leu Ser His Ser Pro Gly Lys
            450                 455

<210> SEQ ID NO 25
<211> LENGTH: 217
<212> TYPE: PRT
<213> ORGANISM: Artificial Sequence
<220> FEATURE:
<223> OTHER INFORMATION: Synthetic: Chimeric variable light chain of Mab
      A and canine kappa light constant region, (Chimeric A LC kappa)

<400> SEQUENCE: 25

Asp Ile Val Met Thr Gln Thr Pro Ala Ser Met Ser Ile Ser Val Gly
1               5                   10                  15

Asp Arg Val Thr Met Asn Cys Lys Ala Ser Gln Asn Val Asp Ser Asn
            20                  25                  30

Val Asp Trp Tyr Gln Gln Lys Thr Gly Gln Ser Pro Asn Leu Leu Ile
        35                  40                  45

Tyr Lys Ala Ser Asn Arg Asn Thr Gly Val Pro Asp Arg Phe Thr Gly
    50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Thr Ser Tyr Pro Leu
                85                  90                  95

Thr Phe Gly Ser Gly Thr Lys Leu Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160
```

```
Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215
```

<210> SEQ ID NO 26
<211> LENGTH: 19
<212> TYPE: PRT
<213> ORGANISM: Artificial Sequence
<220> FEATURE:
<223> OTHER INFORMATION: Synthetic: Heavy chain leader

<400> SEQUENCE: 26

```
Met Ala Val Leu Gly Leu Leu Leu Cys Leu Val Thr Phe Pro Ser Cys
1               5                   10                  15

Val Leu Ser
```

<210> SEQ ID NO 27
<211> LENGTH: 20
<212> TYPE: PRT
<213> ORGANISM: Artificial Sequence
<220> FEATURE:
<223> OTHER INFORMATION: Synthetic: Light chain leader

<400> SEQUENCE: 27

```
Met Glu Thr Asp Thr Leu Leu Leu Trp Val Leu Leu Leu Trp Val Pro
1               5                   10                  15

Gly Ser Thr Gly
            20
```

<210> SEQ ID NO 28
<211> LENGTH: 476
<212> TYPE: PRT
<213> ORGANISM: Artificial Sequence
<220> FEATURE:
<223> OTHER INFORMATION: Synthetic: Chimeric variable heavy chain of Mab
      A and canine IgG-B with leader sequence, (Chimeric A HC IgG-B with
      leader)

<400> SEQUENCE: 28

```
Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Ser Ser Tyr His Val His Trp Val Arg Gln Pro Pro Gly Lys Gly Leu
    50                  55                  60

Glu Trp Leu Gly Val Met Trp Asn Asp Gly Asp Thr Ser Tyr Asn Leu
65                  70                  75                  80

Ala Leu Asn Ser Arg Leu Ser Ile Ser Arg Asp Thr Ser Lys Ser Gln
                85                  90                  95

Val Phe Phe Lys Met Ser Ser Leu Gln Thr Glu Asp Thr Ala Thr Tyr
            100                 105                 110

Tyr Cys Ala Arg Pro Glu Leu Pro Gly Leu Thr Tyr Gly Val Trp Phe
        115                 120                 125
```

```
Pro Tyr Trp Gly Gln Gly Thr Leu Val Thr Val Ser Ser Ala Ser Thr
    130                 135                 140
Thr Ala Pro Ser Val Phe Pro Leu Ala Pro Ser Cys Gly Ser Thr Ser
145                 150                 155                 160
Gly Ser Thr Val Ala Leu Ala Cys Leu Val Ser Gly Tyr Phe Pro Glu
                165                 170                 175
Pro Val Thr Val Ser Trp Asn Ser Gly Ser Leu Thr Ser Gly Val His
            180                 185                 190
Thr Phe Pro Ser Val Leu Gln Ser Ser Gly Leu Tyr Ser Leu Ser Ser
        195                 200                 205
Met Val Thr Val Pro Ser Ser Arg Trp Pro Ser Glu Thr Phe Thr Cys
    210                 215                 220
Asn Val Ala His Pro Ala Ser Lys Thr Lys Val Asp Lys Pro Val Pro
225                 230                 235                 240
Lys Arg Glu Asn Gly Arg Val Pro Arg Pro Pro Asp Cys Pro Lys Cys
                245                 250                 255
Pro Ala Pro Glu Met Leu Gly Gly Pro Ser Val Phe Ile Phe Pro Pro
            260                 265                 270
Lys Pro Lys Asp Thr Leu Leu Ile Ala Arg Thr Pro Glu Val Thr Cys
        275                 280                 285
Val Val Val Asp Leu Asp Pro Glu Asp Pro Glu Val Gln Ile Ser Trp
    290                 295                 300
Phe Val Asp Gly Lys Gln Met Gln Thr Ala Lys Thr Gln Pro Arg Glu
305                 310                 315                 320
Glu Gln Phe Asn Gly Thr Tyr Arg Val Val Ser Val Leu Pro Ile Gly
                325                 330                 335
His Gln Asp Trp Leu Lys Gly Lys Gln Phe Thr Cys Lys Val Asn Asn
            340                 345                 350
Lys Ala Leu Pro Ser Pro Ile Glu Arg Thr Ile Ser Lys Ala Arg Gly
        355                 360                 365
Gln Ala His Gln Pro Ser Val Tyr Val Leu Pro Pro Ser Arg Glu Glu
    370                 375                 380
Leu Ser Lys Asn Thr Val Ser Leu Thr Cys Leu Ile Lys Asp Phe Phe
385                 390                 395                 400
Pro Pro Asp Ile Asp Val Glu Trp Gln Ser Asn Gly Gln Gln Glu Pro
                405                 410                 415
Glu Ser Lys Tyr Arg Thr Thr Pro Pro Gln Leu Asp Glu Asp Gly Ser
            420                 425                 430
Tyr Phe Leu Tyr Ser Lys Leu Ser Val Asp Lys Ser Arg Trp Gln Arg
        435                 440                 445
Gly Asp Thr Phe Ile Cys Ala Val Met His Glu Ala Leu His Asn His
    450                 455                 460
Tyr Thr Gln Glu Ser Leu Ser His Ser Pro Gly Lys
465                 470                 475
```

<210> SEQ ID NO 29
<211> LENGTH: 476
<212> TYPE: PRT
<213> ORGANISM: Artificial Sequence
<220> FEATURE:
<223> OTHER INFORMATION: Synthetic: Chimeric variable heavy chain of Mab
      A v2 and canine IgG-B with leader sequence, HC-FR1 Q13A, HC-FR4
      S11A, (Chimeric A HC v2 IgG-B with leader)

<400> SEQUENCE: 29

Met Ala Val Leu Gly Leu Leu Leu Cys Leu Val Thr Phe Pro Ser Cys

-continued

```
1               5              10              15
Val Leu Ser Gln Val Gln Leu Lys Glu Ser Gly Pro Gly Leu Val Ala
            20              25              30
Pro Ser Gln Thr Leu Ser Leu Thr Cys Thr Val Ser Gly Phe Ser Leu
            35              40              45
Ser Ser Tyr His Val His Trp Val Arg Gln Pro Pro Gly Lys Gly Leu
50              55              60
Glu Trp Leu Gly Val Met Trp Asn Asp Gly Asp Thr Ser Tyr Asn Leu
65              70              75              80
Ala Leu Asn Ser Arg Leu Ser Ile Ser Arg Asp Thr Ser Lys Ser Gln
            85              90              95
Val Phe Phe Lys Met Ser Ser Leu Gln Thr Glu Asp Thr Ala Thr Tyr
            100             105             110
Tyr Cys Ala Arg Pro Glu Leu Pro Gly Leu Thr Tyr Gly Val Trp Phe
            115             120             125
Pro Tyr Trp Gly Gln Gly Thr Leu Val Thr Val Ser Ala Ala Ser Thr
            130             135             140
Thr Ala Pro Ser Val Phe Pro Leu Ala Pro Ser Cys Gly Ser Thr Ser
145             150             155             160
Gly Ser Thr Val Ala Leu Ala Cys Leu Val Ser Gly Tyr Phe Pro Glu
            165             170             175
Pro Val Thr Val Ser Trp Asn Ser Gly Ser Leu Thr Ser Gly Val His
            180             185             190
Thr Phe Pro Ser Val Leu Gln Ser Ser Gly Leu Tyr Ser Leu Ser Ser
            195             200             205
Met Val Thr Val Pro Ser Ser Arg Trp Pro Ser Glu Thr Phe Thr Cys
            210             215             220
Asn Val Ala His Pro Ala Ser Lys Thr Lys Val Asp Lys Pro Val Pro
225             230             235             240
Lys Arg Glu Asn Gly Arg Val Pro Arg Pro Pro Asp Cys Pro Lys Cys
            245             250             255
Pro Ala Pro Glu Met Leu Gly Gly Pro Ser Val Phe Ile Phe Pro Pro
            260             265             270
Lys Pro Lys Asp Thr Leu Leu Ile Ala Arg Thr Pro Glu Val Thr Cys
            275             280             285
Val Val Val Asp Leu Asp Pro Glu Asp Pro Glu Val Gln Ile Ser Trp
            290             295             300
Phe Val Asp Gly Lys Gln Met Gln Thr Ala Lys Thr Gln Pro Arg Glu
305             310             315             320
Glu Gln Phe Asn Gly Thr Tyr Arg Val Val Ser Val Leu Pro Ile Gly
            325             330             335
His Gln Asp Trp Leu Lys Gly Lys Gln Phe Thr Cys Lys Val Asn Asn
            340             345             350
Lys Ala Leu Pro Ser Pro Ile Glu Arg Thr Ile Ser Lys Ala Arg Gly
            355             360             365
Gln Ala His Gln Pro Ser Val Tyr Val Leu Pro Pro Ser Arg Glu Glu
            370             375             380
Leu Ser Lys Asn Thr Val Ser Leu Thr Cys Leu Ile Lys Asp Phe Phe
385             390             395             400
Pro Pro Asp Ile Asp Val Glu Trp Gln Ser Asn Gly Gln Gln Glu Pro
            405             410             415
Glu Ser Lys Tyr Arg Thr Thr Pro Pro Gln Leu Asp Glu Asp Gly Ser
            420             425             430
```

```
Tyr Phe Leu Tyr Ser Lys Leu Ser Val Asp Lys Ser Arg Trp Gln Arg
        435                 440                 445

Gly Asp Thr Phe Ile Cys Ala Val Met His Glu Ala Leu His Asn His
    450                 455                 460

Tyr Thr Gln Glu Ser Leu Ser His Ser Pro Gly Lys
465                 470                 475

<210> SEQ ID NO 30
<211> LENGTH: 237
<212> TYPE: PRT
<213> ORGANISM: Artificial Sequence
<220> FEATURE:
<223> OTHER INFORMATION: Synthetic: Chimeric variable light chain of Mab
      A and canine kappa light constant region with leader sequence,
      (Chimeric A LC kappa with leader)

<400> SEQUENCE: 30

Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Ala Ser Met Ser
            20                  25                  30

Ile Ser Val Gly Asp Arg Val Thr Met Asn Cys Lys Ala Ser Gln Asn
        35                  40                  45

Val Asp Ser Asn Val Asp Trp Tyr Gln Gln Lys Thr Gly Gln Ser Pro
    50                  55                  60

Asn Leu Leu Ile Tyr Lys Ala Ser Asn Arg Asn Thr Gly Val Pro Asp
65                  70                  75                  80

Arg Phe Thr Gly Ser Gly Ser Gly Thr Asp Phe Thr Phe Thr Ile Ser
            85                  90                  95

Asn Met Gln Ala Glu Asp Leu Ala Val Tyr Tyr Cys Met Gln Ser Thr
        100                 105                 110

Ser Tyr Pro Leu Thr Phe Gly Ser Gly Thr Lys Leu Glu Ile Lys Arg
    115                 120                 125

Asn Asp Ala Gln Pro Ala Val Tyr Leu Phe Gln Pro Ser Pro Asp Gln
130                 135                 140

Leu His Thr Gly Ser Ala Ser Val Val Cys Leu Leu Asn Ser Phe Tyr
145                 150                 155                 160

Pro Lys Asp Ile Asn Val Lys Trp Lys Val Asp Gly Val Ile Gln Asp
            165                 170                 175

Thr Gly Ile Gln Glu Ser Val Thr Glu Gln Asp Lys Asp Ser Thr Tyr
        180                 185                 190

Ser Leu Ser Ser Thr Leu Thr Met Ser Ser Thr Glu Tyr Leu Ser His
    195                 200                 205

Glu Leu Tyr Ser Cys Glu Ile Thr His Lys Ser Leu Pro Ser Thr Leu
    210                 215                 220

Ile Lys Ser Phe Gln Arg Ser Glu Cys Gln Arg Val Asp
225                 230                 235

<210> SEQ ID NO 31
<211> LENGTH: 457
<212> TYPE: PRT
<213> ORGANISM: Artificial Sequence
<220> FEATURE:
<223> OTHER INFORMATION: Synthetic: Chimeric variable heavy chain of Mab
      A and feline IgG-1, (Chimeric A HC IgG-1)

<400> SEQUENCE: 31

Gln Val Gln Leu Lys Glu Ser Gly Pro Gly Leu Val Gln Pro Ser Gln
```

-continued

```
1               5                   10                  15
Thr Leu Ser Leu Thr Cys Thr Val Ser Gly Phe Ser Leu Ser Ser Tyr
            20                  25                  30

His Val His Trp Val Arg Gln Pro Gly Lys Gly Leu Glu Trp Leu
            35                  40                  45

Gly Val Met Trp Asn Asp Gly Asp Thr Ser Tyr Asn Leu Ala Leu Asn
            50                  55                  60

Ser Arg Leu Ser Ile Ser Arg Asp Thr Ser Lys Ser Gln Val Phe Phe
65                  70                  75                  80

Lys Met Ser Ser Leu Gln Thr Glu Asp Thr Ala Thr Tyr Tyr Cys Ala
            85                  90                  95

Arg Pro Glu Leu Pro Gly Leu Thr Tyr Gly Val Trp Phe Pro Tyr Trp
            100                 105                 110

Gly Gln Gly Thr Leu Val Thr Val Ser Ser Ala Ser Thr Thr Ala Pro
            115                 120                 125

Ser Val Phe Pro Leu Ala Pro Ser Cys Gly Thr Thr Ser Gly Ala Thr
            130                 135                 140

Val Ala Leu Ala Cys Leu Val Leu Gly Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ala Ser Gly Leu Tyr Ser Leu Ser Ser Met Val Thr
            180                 185                 190

Val Pro Ser Ser Arg Trp Leu Ser Asp Thr Phe Thr Cys Asn Val Ala
            195                 200                 205

His Pro Pro Ser Asn Thr Lys Val Asp Lys Thr Val Arg Lys Thr Asp
            210                 215                 220

His Pro Pro Gly Pro Lys Pro Cys Asp Cys Pro Lys Cys Pro Pro Pro
225                 230                 235                 240

Glu Met Leu Gly Gly Pro Ser Ile Phe Ile Phe Pro Pro Lys Pro Lys
            245                 250                 255

Asp Thr Leu Ser Ile Ser Arg Thr Pro Glu Val Thr Cys Leu Val Val
            260                 265                 270

Asp Leu Gly Pro Asp Asp Ser Asp Val Gln Ile Thr Trp Phe Val Asp
            275                 280                 285

Asn Thr Gln Val Tyr Thr Ala Lys Thr Ser Pro Arg Glu Glu Gln Phe
            290                 295                 300

Asn Ser Thr Tyr Arg Val Val Ser Val Leu Pro Ile Leu His Gln Asp
305                 310                 315                 320

Trp Leu Lys Gly Lys Glu Phe Lys Cys Lys Val Asn Ser Lys Ser Leu
            325                 330                 335

Pro Ser Pro Ile Glu Arg Thr Ile Ser Lys Ala Lys Gly Gln Pro His
            340                 345                 350

Glu Pro Gln Val Tyr Val Leu Pro Pro Ala Gln Glu Glu Leu Ser Arg
            355                 360                 365

Asn Lys Val Ser Val Thr Cys Leu Ile Lys Ser Phe His Pro Pro Asp
370                 375                 380

Ile Ala Val Glu Trp Glu Ile Thr Gly Gln Pro Glu Pro Glu Asn Asn
385                 390                 395                 400

Tyr Arg Thr Thr Pro Pro Gln Leu Asp Ser Asp Gly Thr Tyr Phe Val
            405                 410                 415

Tyr Ser Lys Leu Ser Val Asp Arg Ser His Trp Gln Arg Gly Asn Thr
            420                 425                 430
```

```
Tyr Thr Cys Ser Val Ser His Glu Ala Leu His Ser His His Thr Gln
        435                 440                 445

Lys Ser Leu Thr Gln Ser Pro Gly Lys
    450                 455

<210> SEQ ID NO 32
<211> LENGTH: 217
<212> TYPE: PRT
<213> ORGANISM: Artificial Sequence
<220> FEATURE:
<223> OTHER INFORMATION: Synthetic: Chimeric variable light chain of Mab
      A and feline kappa light constant region , (Chimeric A LC kappa)

<400> SEQUENCE: 32

Asp Ile Val Met Thr Gln Thr Pro Ala Ser Met Ser Ile Ser Val Gly
1               5                   10                  15

Asp Arg Val Thr Met Asn Cys Lys Ala Ser Gln Asn Val Asp Ser Asn
            20                  25                  30

Val Asp Trp Tyr Gln Gln Lys Thr Gly Gln Ser Pro Asn Leu Leu Ile
        35                  40                  45

Tyr Lys Ala Ser Asn Arg Asn Thr Gly Val Pro Asp Arg Phe Thr Gly
    50                  55                  60

Ser Gly Ser Gly Thr Asp Phe Thr Phe Thr Ile Ser Asn Met Gln Ala
65              70                  75                  80

Glu Asp Leu Ala Val Tyr Tyr Cys Met Gln Ser Thr Ser Tyr Pro Leu
                85                  90                  95

Thr Phe Gly Ser Gly Thr Lys Leu Glu Ile Lys Arg Ser Asp Ala Gln
            100                 105                 110

Pro Ser Val Phe Leu Phe Gln Pro Ser Leu Asp Glu Leu His Thr Gly
        115                 120                 125

Ser Ala Ser Ile Val Cys Ile Leu Asn Asp Phe Tyr Pro Lys Glu Val
130                 135                 140

Asn Val Lys Trp Lys Val Asp Gly Val Val Gln Asn Lys Gly Ile Gln
145                 150                 155                 160

Glu Ser Thr Thr Glu Gln Asn Ser Lys Asp Ser Thr Tyr Ser Leu Ser
                165                 170                 175

Ser Thr Leu Thr Met Ser Ser Thr Glu Tyr Gln Ser His Glu Lys Phe
            180                 185                 190

Ser Cys Glu Val Thr His Lys Ser Leu Ala Ser Thr Leu Val Lys Ser
        195                 200                 205

Phe Asn Arg Ser Glu Cys Gln Arg Glu
    210                 215

<210> SEQ ID NO 33
<211> LENGTH: 217
<212> TYPE: PRT
<213> ORGANISM: Artificial Sequence
<220> FEATURE:
<223> OTHER INFORMATION: Synthetic: Chimeric variable light chain of Mab
      A and feline kappa light constant region with no N-linked
      glycosylation site, (Chimeric A LC kappa aglycos)

<400> SEQUENCE: 33

Asp Ile Val Met Thr Gln Thr Pro Ala Ser Met Ser Ile Ser Val Gly
1               5                   10                  15

Asp Arg Val Thr Met Asn Cys Lys Ala Ser Gln Asn Val Asp Ser Asn
            20                  25                  30

Val Asp Trp Tyr Gln Gln Lys Thr Gly Gln Ser Pro Asn Leu Leu Ile
```

```
               35                  40                  45
Tyr Lys Ala Ser Asn Arg Asn Thr Gly Val Pro Asp Arg Phe Thr Gly
 50                  55                  60

Ser Gly Ser Gly Thr Asp Phe Thr Phe Thr Ile Ser Asn Met Gln Ala
 65                  70                  75                  80

Glu Asp Leu Ala Val Tyr Tyr Cys Met Gln Ser Thr Ser Tyr Pro Leu
                 85                  90                  95

Thr Phe Gly Ser Gly Thr Lys Leu Glu Ile Lys Arg Ser Asp Ala Gln
                100                 105                 110

Pro Ser Val Phe Leu Phe Gln Pro Ser Leu Asp Glu Leu His Thr Gly
                115                 120                 125

Ser Ala Ser Ile Val Cys Ile Leu Asn Asp Phe Tyr Pro Lys Glu Val
    130                 135                 140

Asn Val Lys Trp Lys Val Asp Gly Val Val Gln Asn Lys Gly Ile Gln
145                 150                 155                 160

Glu Ser Thr Thr Glu Gln Asn Ser Lys Asp Ser Thr Tyr Ser Leu Ser
                165                 170                 175

Ser Thr Leu Thr Met Ser Ser Thr Glu Tyr Gln Ser His Glu Lys Phe
                180                 185                 190

Ser Cys Glu Val Thr His Lys Ser Leu Ala Ser Thr Leu Val Lys Ser
            195                 200                 205

Phe Gln Arg Ser Glu Cys Gln Arg Glu
    210                 215

<210> SEQ ID NO 34
<211> LENGTH: 476
<212> TYPE: PRT
<213> ORGANISM: Artificial Sequence
<220> FEATURE:
<223> OTHER INFORMATION: Synthetic: Caninized variable heavy chain of
      Mab A v3 and canine IgG-B with leader sequence, (Chimeric A HC v3
      IgG-B with leader)

<400> SEQUENCE: 34

Met Ala Val Leu Gly Leu Leu Cys Leu Val Thr Phe Pro Ser Cys
1               5                  10                  15

Val Leu Ser Gln Val Gln Leu Val Glu Ser Gly Gly Asp Leu Val Lys
                20                  25                  30

Pro Gly Gly Thr Leu Arg Leu Ser Cys Thr Val Ser Gly Phe Ser Leu
            35                  40                  45

Ser Ser Tyr His Val His Trp Val Arg Gln Pro Pro Gly Lys Gly Leu
 50                  55                  60

Glu Trp Val Ala Val Met Trp Asn Asp Gly Asp Thr Ser Tyr Asn Leu
 65                  70                  75                  80

Ala Val Lys Gly Arg Phe Thr Ile Ser Arg Asp Asn Ala Lys Asn Thr
                 85                  90                  95

Leu Tyr Leu Gln Met Asn Ser Leu Arg Ala Glu Asp Thr Ala Val Tyr
                100                 105                 110

Tyr Cys Ala Arg Pro Glu Leu Pro Gly Leu Thr Tyr Gly Val Trp Phe
            115                 120                 125

Pro Tyr Trp Gly Gln Gly Thr Leu Val Thr Val Ser Ser Ala Ser Thr
    130                 135                 140

Thr Ala Pro Ser Val Phe Pro Leu Ala Pro Ser Cys Gly Ser Thr Ser
145                 150                 155                 160

Gly Ser Thr Val Ala Leu Ala Cys Leu Val Ser Gly Tyr Phe Pro Glu
                165                 170                 175
```

```
Pro Val Thr Val Ser Trp Asn Ser Gly Ser Leu Thr Ser Gly Val His
            180                 185                 190

Thr Phe Pro Ser Val Leu Gln Ser Ser Gly Leu Tyr Ser Leu Ser Ser
            195                 200                 205

Met Val Thr Val Pro Ser Ser Arg Trp Pro Ser Glu Thr Phe Thr Cys
            210                 215                 220

Asn Val Ala His Pro Ala Ser Lys Thr Lys Val Asp Lys Pro Val Pro
225                 230                 235                 240

Lys Arg Glu Asn Gly Arg Val Pro Arg Pro Asp Cys Pro Lys Cys
            245                 250                 255

Pro Ala Pro Glu Met Leu Gly Gly Pro Ser Val Phe Ile Phe Pro Pro
            260                 265                 270

Lys Pro Lys Asp Thr Leu Leu Ile Ala Arg Thr Pro Glu Val Thr Cys
            275                 280                 285

Val Val Val Asp Leu Asp Pro Glu Asp Pro Glu Val Gln Ile Ser Trp
            290                 295                 300

Phe Val Asp Gly Lys Gln Met Gln Thr Ala Lys Thr Gln Pro Arg Glu
305                 310                 315                 320

Glu Gln Phe Asn Gly Thr Tyr Arg Val Val Ser Val Leu Pro Ile Gly
            325                 330                 335

His Gln Asp Trp Leu Lys Gly Lys Gln Phe Thr Cys Lys Val Asn Asn
            340                 345                 350

Lys Ala Leu Pro Ser Pro Ile Glu Arg Thr Ile Ser Lys Ala Arg Gly
            355                 360                 365

Gln Ala His Gln Pro Ser Val Tyr Val Leu Pro Pro Ser Arg Glu Glu
            370                 375                 380

Leu Ser Lys Asn Thr Val Ser Leu Thr Cys Leu Ile Lys Asp Phe Phe
385                 390                 395                 400

Pro Pro Asp Ile Asp Val Glu Trp Gln Ser Asn Gly Gln Gln Glu Pro
            405                 410                 415

Glu Ser Lys Tyr Arg Thr Thr Pro Pro Gln Leu Asp Glu Asp Gly Ser
            420                 425                 430

Tyr Phe Leu Tyr Ser Lys Leu Ser Val Asp Lys Ser Arg Trp Gln Arg
            435                 440                 445

Gly Asp Thr Phe Ile Cys Ala Val Met His Glu Ala Leu His Asn His
450                 455                 460

Tyr Thr Gln Glu Ser Leu Ser His Ser Pro Gly Lys
465                 470                 475

<210> SEQ ID NO 35
<211> LENGTH: 476
<212> TYPE: PRT
<213> ORGANISM: Artificial Sequence
<220> FEATURE:
<223> OTHER INFORMATION: Synthetic: Caninized variable heavy chain of
      Mab A v4 and canine IgG-B with leader sequence, (Caninized A HC v4
      IgG-B with leader)

<400> SEQUENCE: 35

Met Ala Val Leu Gly Leu Leu Leu Cys Leu Val Thr Phe Pro Ser Cys
1               5                   10                  15

Val Leu Ser Glu Val Gln Leu Val Glu Ser Gly Gly Asp Leu Val Lys
            20                  25                  30

Pro Gly Gly Thr Leu Arg Leu Ser Cys Thr Val Ser Gly Phe Ser Leu
            35                  40                  45
```

-continued

Ser Ser Tyr His Val His Trp Val Arg Gln Pro Pro Gly Lys Gly Leu
        50              55                  60

Glu Trp Leu Gly Val Met Trp Asn Asp Gly Asp Thr Ser Tyr Asn Leu
65              70              75                  80

Ala Val Lys Gly Arg Phe Thr Ile Ser Arg Asp Asn Ala Lys Asn Thr
                85              90              95

Leu Tyr Phe Gln Met Asn Ser Leu Arg Ala Glu Asp Thr Ala Thr Tyr
            100             105             110

Tyr Cys Ala Arg Pro Glu Leu Pro Gly Leu Thr Tyr Gly Val Trp Phe
            115             120             125

Pro Tyr Trp Gly Gln Gly Thr Leu Val Thr Val Ser Ser Ala Ser Thr
        130             135             140

Thr Ala Pro Ser Val Phe Pro Leu Ala Pro Ser Cys Gly Ser Thr Ser
145             150             155             160

Gly Ser Thr Val Ala Leu Ala Cys Leu Val Ser Gly Tyr Phe Pro Glu
                165             170             175

Pro Val Thr Val Ser Trp Asn Ser Gly Ser Leu Thr Ser Gly Val His
            180             185             190

Thr Phe Pro Ser Val Leu Gln Ser Ser Gly Leu Tyr Ser Leu Ser Ser
        195             200             205

Met Val Thr Val Pro Ser Ser Arg Trp Pro Ser Glu Thr Phe Thr Cys
    210             215             220

Asn Val Ala His Pro Ala Ser Lys Thr Lys Val Asp Lys Pro Val Pro
225             230             235             240

Lys Arg Glu Asn Gly Arg Val Pro Arg Pro Asp Cys Pro Lys Cys
                245             250             255

Pro Ala Pro Glu Met Leu Gly Gly Pro Ser Val Phe Ile Phe Pro Pro
            260             265             270

Lys Pro Lys Asp Thr Leu Leu Ile Ala Arg Thr Pro Glu Val Thr Cys
            275             280             285

Val Val Val Asp Leu Asp Pro Glu Asp Pro Glu Val Gln Ile Ser Trp
        290             295             300

Phe Val Asp Gly Lys Gln Met Gln Thr Ala Lys Thr Gln Pro Arg Glu
305             310             315             320

Glu Gln Phe Asn Gly Thr Tyr Arg Val Val Ser Val Leu Pro Ile Gly
                325             330             335

His Gln Asp Trp Leu Lys Gly Lys Gln Phe Thr Cys Lys Val Asn Asn
            340             345             350

Lys Ala Leu Pro Ser Pro Ile Glu Arg Thr Ile Ser Lys Ala Arg Gly
            355             360             365

Gln Ala His Gln Pro Ser Val Tyr Val Leu Pro Pro Ser Arg Glu Glu
        370             375             380

Leu Ser Lys Asn Thr Val Ser Leu Thr Cys Leu Ile Lys Asp Phe Phe
385             390             395             400

Pro Pro Asp Ile Asp Val Glu Trp Gln Ser Asn Gly Gln Gln Glu Pro
                405             410             415

Glu Ser Lys Tyr Arg Thr Thr Pro Pro Gln Leu Asp Glu Asp Gly Ser
            420             425             430

Tyr Phe Leu Tyr Ser Lys Leu Ser Val Asp Lys Ser Arg Trp Gln Arg
            435             440             445

Gly Asp Thr Phe Ile Cys Ala Val Met His Glu Ala Leu His Asn His
450             455             460

Tyr Thr Gln Glu Ser Leu Ser His Ser Pro Gly Lys

<210> SEQ ID NO 36
<211> LENGTH: 237
<212> TYPE: PRT
<213> ORGANISM: Artificial Sequence
<220> FEATURE:
<223> OTHER INFORMATION: Synthetic: Caninized variable light chain of
      Mab A and canine kappa light constant region with leader sequence,
      (Caninized A LC kappa with leader)

<400> SEQUENCE: 36

Met Glu Thr Asp Thr Leu Leu Leu Trp Val Leu Leu Trp Val Pro
1               5                   10                  15

Gly Ser Thr Gly Glu Ile Val Met Thr Gln Ser Pro Ala Ser Leu Ser
            20                  25                  30

Leu Ser Gln Glu Glu Lys Val Thr Ile Thr Cys Lys Ala Ser Gln Asn
        35                  40                  45

Val Asp Ser Asn Val Asp Trp Tyr Gln Gln Lys Pro Gly Gln Ala Pro
50                  55                  60

Lys Leu Leu Ile Tyr Lys Ala Ser Asn Arg Asn Thr Gly Val Pro Ser
65                  70                  75                  80

Arg Phe Ser Gly Ser Gly Ser Gly Thr Asp Phe Ser Phe Thr Ile Ser
                85                  90                  95

Ser Leu Glu Pro Glu Asp Val Ala Val Tyr Tyr Cys Met Gln Ser Thr
            100                 105                 110

Ser Tyr Pro Leu Thr Phe Gly Gln Gly Thr Lys Leu Glu Ile Lys Arg
        115                 120                 125

Asn Asp Ala Gln Pro Ala Val Tyr Leu Phe Gln Pro Ser Pro Asp Gln
130                 135                 140

Leu His Thr Gly Ser Ala Ser Val Val Cys Leu Leu Asn Ser Phe Tyr
145                 150                 155                 160

Pro Lys Asp Ile Asn Val Lys Trp Lys Val Asp Gly Val Ile Gln Asp
                165                 170                 175

Thr Gly Ile Gln Glu Ser Val Thr Glu Gln Asp Lys Asp Ser Thr Tyr
            180                 185                 190

Ser Leu Ser Ser Thr Leu Thr Met Ser Ser Thr Glu Tyr Leu Ser His
        195                 200                 205

Glu Leu Tyr Ser Cys Glu Ile Thr His Lys Ser Leu Pro Ser Thr Leu
    210                 215                 220

Ile Lys Ser Phe Gln Arg Ser Glu Cys Gln Arg Val Asp
225                 230                 235

<210> SEQ ID NO 37
<211> LENGTH: 457
<212> TYPE: PRT
<213> ORGANISM: Artificial Sequence
<220> FEATURE:
<223> OTHER INFORMATION: Synthetic: Caninized variable heavy chain of
      Mab A v3 and canine IgG-B , (Caninized A HC v3 IgG-B)

<400> SEQUENCE: 37

Gln Val Gln Leu Val Glu Ser Gly Gly Asp Leu Val Lys Pro Gly Gly
1               5                   10                  15

Thr Leu Arg Leu Ser Cys Thr Val Ser Gly Phe Ser Leu Ser Ser Tyr
            20                  25                  30

His Val His Trp Val Arg Gln Pro Pro Gly Lys Gly Leu Glu Trp Val
        35                  40                  45

```
Ala Val Met Trp Asn Asp Gly Asp Thr Ser Tyr Asn Leu Ala Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Pro Glu Leu Pro Gly Leu Thr Tyr Gly Val Trp Phe Pro Tyr Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
210                 215                 220

Asn Gly Arg Val Pro Arg Pro Pro Asp Cys Pro Lys Cys Pro Ala Pro
225                 230                 235                 240

Glu Met Leu Gly Gly Pro Ser Val Phe Ile Phe Pro Pro Lys Pro Lys
                245                 250                 255

Asp Thr Leu Leu Ile Ala Arg Thr Pro Glu Val Thr Cys Val Val Val
            260                 265                 270

Asp Leu Asp Pro Glu Asp Pro Glu Val Gln Ile Ser Trp Phe Val Asp
        275                 280                 285

Gly Lys Gln Met Gln Thr Ala Lys Thr Gln Pro Arg Glu Glu Gln Phe
290                 295                 300

Asn Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
        355                 360                 365

Asn Thr Val Ser Leu Thr Cys Leu Ile Lys Asp Phe Phe Pro Pro Asp
370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
                405                 410                 415

Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
        435                 440                 445

Glu Ser Leu Ser His Ser Pro Gly Lys
450                 455
```

```
<210> SEQ ID NO 38
<211> LENGTH: 457
<212> TYPE: PRT
<213> ORGANISM: Artificial Sequence
<220> FEATURE:
<223> OTHER INFORMATION: Synthetic: Caninized variable heavy chain of
      Mab A v4 and canine IgG-B , (Caninized A HC v4 IgG-B)

<400> SEQUENCE: 38

Glu Val Gln Leu Val Glu Ser Gly Gly Asp Leu Val Lys Pro Gly Gly
1               5                   10                  15

Thr Leu Arg Leu Ser Cys Thr Val Ser Gly Phe Ser Leu Ser Ser Tyr
            20                  25                  30

His Val His Trp Val Arg Gln Pro Pro Gly Lys Gly Leu Glu Trp Leu
        35                  40                  45

Gly Val Met Trp Asn Asp Gly Asp Thr Ser Tyr Asn Leu Ala Val Lys
    50                  55                  60

Gly Arg Phe Thr Ile Ser Arg Asp Asn Ala Lys Asn Thr Leu Tyr Phe
65              70                  75                  80

Gln Met Asn Ser Leu Arg Ala Glu Asp Thr Ala Thr Tyr Tyr Cys Ala
                85                  90                  95

Arg Pro Glu Leu Pro Gly Leu Tyr Gly Val Trp Phe Pro Tyr Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
    210                 215                 220

Asn Gly Arg Val Pro Arg Pro Pro Asp Cys Pro Lys Cys Pro Ala Pro
225                 230                 235                 240

Glu Met Leu Gly Gly Pro Ser Val Phe Ile Phe Pro Pro Lys Pro Lys
                245                 250                 255

Asp Thr Leu Leu Ile Ala Arg Thr Pro Glu Val Thr Cys Val Val Val
            260                 265                 270

Asp Leu Asp Pro Glu Asp Pro Glu Val Gln Ile Ser Trp Phe Val Asp
        275                 280                 285

Gly Lys Gln Met Gln Thr Ala Lys Thr Gln Pro Arg Glu Glu Gln Phe
    290                 295                 300

Asn Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
        355                 360                 365
```

Asn Thr Val Ser Leu Thr Cys Leu Ile Lys Asp Phe Pro Pro Asp
            370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
                405                 410                 415

Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
            435                 440                 445

Glu Ser Leu Ser His Ser Pro Gly Lys
            450                 455

<210> SEQ ID NO 39
<211> LENGTH: 217
<212> TYPE: PRT
<213> ORGANISM: Artificial Sequence
<220> FEATURE:
<223> OTHER INFORMATION: Synthetic: Caninized variable light chain of
      Mab A and canine kappa light constant region , (Caninized A LC
      kappa)

<400> SEQUENCE: 39

Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Asn Val Asp Ser Asn
            20                  25                  30

Val Asp Trp Tyr Gln Gln Lys Pro Gly Gln Ala Pro Lys Leu Leu Ile
        35                  40                  45

Tyr Lys Ala Ser Asn Arg Asn Thr Gly Val Pro Ser Arg Phe Ser Gly
50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Met Gln Ser Thr Ser Tyr Pro Leu
            85                  90                  95

Thr Phe Gly Gln Gly Thr Lys Leu Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
            165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
        210                 215

<210> SEQ ID NO 40
<211> LENGTH: 119
<212> TYPE: PRT
<213> ORGANISM: Artificial Sequence
<220> FEATURE:
<223> OTHER INFORMATION: Synthetic: Felinized variable heavy chain of Mab A , (Felinized A HC)

<400> SEQUENCE: 40

Gln Leu Thr Leu Arg Glu Ser Gly Pro Gly Leu Val Lys Pro Ser Gln
1               5                   10                  15

Ser Leu Ser Leu Thr Cys Thr Val Ser Gly Phe Ser Leu Ser Ser Tyr
            20                  25                  30

His Val His Trp Ile Arg Gln Arg Pro Gly Arg Gly Leu Glu Trp Leu
        35                  40                  45

Gly Val Met Trp Asn Asp Gly Asp Thr Ser Tyr Ala Phe Gln Gly Arg
    50                  55                  60

Ile Ser Ile Thr Ala Asp Thr Ala Gln Asn Gln Phe Ser Leu Gln Leu
65                  70                  75                  80

Ser Ser Met Thr Thr Asp Asp Thr Ala Val Tyr Tyr Cys Ala Arg Pro
                85                  90                  95

Glu Leu Pro Gly Leu Thr Tyr Gly Val Trp Phe Pro Tyr Trp Gly Gln
            100                 105                 110

Gly Ala Leu Val Thr Val Ser
        115

<210> SEQ ID NO 41
<211> LENGTH: 107
<212> TYPE: PRT
<213> ORGANISM: Artificial Sequence
<220> FEATURE:
<223> OTHER INFORMATION: Synthetic: Felinized variable light chain of
      Mab A , (Felinized A LC)

<400> SEQUENCE: 41

Ala Ile Thr Met Thr Gln Ser Pro Gly Ser Leu Ala Gly Ser Pro Gly
1               5                   10                  15

Gln Gln Val Thr Met Asn Cys Lys Ala Ser Gln Asn Val Asp Ser Asn
            20                  25                  30

Val Asp Trp Tyr Gln Gln Lys Pro Gly Gln His Pro Lys Leu Leu Ile
        35                  40                  45

Tyr Lys Ala Ser Asn Arg Asn Thr Gly Val Pro Asp Arg Phe Ser Gly
    50                  55                  60

Ser Gly Ser Gly Thr Asp Phe Thr Leu Thr Ile Ser Asn Leu Gln Ala
65                  70                  75                  80

Glu Asp Val Ala Ser Tyr Tyr Cys Met Gln Ser Thr Ser Tyr Pro Leu
                85                  90                  95

Thr Phe Gly Gln Gly Thr Lys Leu Glu Ile Lys
            100                 105

<210> SEQ ID NO 42
<211> LENGTH: 10
<212> TYPE: PRT
<213> ORGANISM: Artificial Sequence
<220> FEATURE:
<223> OTHER INFORMATION: Synthetic: Variable heavy chain CDRH1 of Mab B

<400> SEQUENCE: 42

Gly Phe Ser Leu Thr Ser Tyr Gly Val Ser
1               5                   10

<210> SEQ ID NO 43
<211> LENGTH: 9
<212> TYPE: PRT
<213> ORGANISM: Artificial Sequence
<220> FEATURE:

-continued

```
<223> OTHER INFORMATION: Synthetic: Variable heavy chain CDRH2 of Mab B

<400> SEQUENCE: 43

Thr Met Trp Asn Asp Gly Asp Thr Asp
1               5

<210> SEQ ID NO 44
<211> LENGTH: 14
<212> TYPE: PRT
<213> ORGANISM: Artificial Sequence
<220> FEATURE:
<223> OTHER INFORMATION: Synthetic: Variable heavy chain CDRH3 of Mab B

<400> SEQUENCE: 44

Ser Gln Leu Pro Gly Tyr Asn Leu Arg Gly Trp Phe Val Tyr
1               5                   10

<210> SEQ ID NO 45
<211> LENGTH: 25
<212> TYPE: PRT
<213> ORGANISM: Artificial Sequence
<220> FEATURE:
<223> OTHER INFORMATION: Synthetic: Variable heavy chain framework
      region HC-FR1 of Mab B

<400> SEQUENCE: 45

Gln Val Gln Leu Lys Glu Ser Gly Pro Gly Leu Val Gln Pro Ser Gln
1               5                   10                  15

Thr Leu Ser Leu Thr Cys Thr Val Ser
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthetic: Variable heavy chain framework
      region HC-FR1 of Mab B variant 2 (v2), Q16E

<400> SEQUENCE: 46

Gln Val Gln Leu Lys Glu Ser Gly Pro Gly Leu Val Gln Pro Ser Glu
1               5                   10                  15

Thr Leu Ser Leu Thr Cys Thr Val Ser
            20                  25

<210> SEQ ID NO 47
<211> LENGTH: 14
<212> TYPE: PRT
<213> ORGANISM: Artificial Sequence
<220> FEATURE:
<223> OTHER INFORMATION: Synthetic: Variable region heavy chain
      framework region HC-FR2 of Mab B

<400> SEQUENCE: 47

Trp Val Arg Gln Pro Pro Gly Lys Gly Leu Glu Trp Ile Gly
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Synthetic: Variable region heavy chain
      framework region HC-FR2 of Mab B variant 2 (v2), I13M

<400> SEQUENCE: 48
```

```
Trp Val Arg Gln Pro Pro Gly Lys Gly Leu Glu Trp Met Gly
1               5                   10

<210> SEQ ID NO 49
<211> LENGTH: 39
<212> TYPE: PRT
<213> ORGANISM: Artificial Sequence
<220> FEATURE:
<223> OTHER INFORMATION: Synthetic: Variable heavy chain framework
      region HC-FR3 of Mab B

<400> SEQUENCE: 49

Tyr His Ser Ala Leu Arg Ser Arg Leu Ser Ile Ser Arg Asp Ser Ser
1               5                   10                  15

Lys Ser Gln Val Leu Leu Lys Met Asn Ser Leu Gln Thr Glu Asp Thr
            20                  25                  30

Ala Met Tyr Phe Cys Ala Arg
        35

<210> SEQ ID NO 50
<211> LENGTH: 39
<212> TYPE: PRT
<213> ORGANISM: Artificial Sequence
<220> FEATURE:
<223> OTHER INFORMATION: Synthetic: Variable region heavy chain
      framework region HC-FR3 of Mab B variant 2 (v2), H2N, R8K, S15T,
      L21F, M34I, F36Y

<400> SEQUENCE: 50

Tyr Asn Ser Ala Leu Arg Ser Lys Leu Ser Ile Ser Arg Asp Thr Ser
1               5                   10                  15

Lys Ser Gln Val Phe Leu Lys Met Asn Ser Leu Gln Thr Glu Asp Thr
            20                  25                  30

Ala Ile Tyr Tyr Cys Ala Arg
        35

<210> SEQ ID NO 51
<211> LENGTH: 10
<212> TYPE: PRT
<213> ORGANISM: Artificial Sequence
<220> FEATURE:
<223> OTHER INFORMATION: Synthetic: Variable heavy chain framework
      region HC-FR4 of Mab B

<400> SEQUENCE: 51

Trp Gly Gln Gly Thr Leu Val Ile Val Ser
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic: Variable light chain CDRL1 of Mab B

<400> SEQUENCE: 52

Lys Ala Ser His Asn Ile Asn Lys Asn Leu Glu
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic: Variable light chain CDRL2 of Mab B
```

```
<400> SEQUENCE: 53

Tyr Ala Asn Asn Leu Gln Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic: Variable light chain CDRL3 of Mab B

<400> SEQUENCE: 54

Tyr Gln Tyr Asn Ser Gly His Thr Phe
1               5

<210> SEQ ID NO 55
<211> LENGTH: 23
<212> TYPE: PRT
<213> ORGANISM: Artificial Sequence
<220> FEATURE:
<223> OTHER INFORMATION: Synthetic: Variable light chain framework
      region LC-FR1 of Mab B

<400> SEQUENCE: 55

Asp Ile Val Met Thr Gln Thr Pro Ser Leu Leu Ser Ala Ser Val Gly
1               5                   10                  15

Asp Arg Val Thr Leu Asn Cys
            20

<210> SEQ ID NO 56
<211> LENGTH: 23
<212> TYPE: PRT
<213> ORGANISM: Artificial Sequence
<220> FEATURE:
<223> OTHER INFORMATION: Synthetic: Variable light chain framework
      region LC-FR1 of Mab B variant 2 (v2), V3Q, T7S, S9P, L10V, N22S

<400> SEQUENCE: 56

Asp Ile Gln Met Thr Gln Ser Pro Pro Val Leu Ser Ala Ser Val Gly
1               5                   10                  15

Asp Arg Val Thr Leu Ser Cys
            20

<210> SEQ ID NO 57
<211> LENGTH: 15
<212> TYPE: PRT
<213> ORGANISM: Artificial Sequence
<220> FEATURE:
<223> OTHER INFORMATION: Synthetic: Variable light chain framework
      region LC-FR2 of Mab B

<400> SEQUENCE: 57

Trp Tyr Gln Gln Lys Leu Gly Glu Ala Pro Lys Leu Leu Ile Tyr
1               5                   10                  15

<210> SEQ ID NO 58
<211> LENGTH: 32
<212> TYPE: PRT
<213> ORGANISM: Artificial Sequence
<220> FEATURE:
<223> OTHER INFORMATION: Synthetic: Variable light chain framework
      region LC-FR3 of Mab B

<400> SEQUENCE: 58

Gly Ile Ser Ser Arg Phe Ser Gly Ser Gly Ser Gly Thr Asp Tyr Thr
1               5                   10                  15
```

```
Leu Thr Ile Ser Ser Leu Gln Pro Glu Asp Val Ala Thr Tyr Tyr Cys
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Synthetic: Variable light chain framework
      region LC-FR3 of Mab B variant 2 (v2), S3P

<400> SEQUENCE: 59

Gly Ile Pro Ser Arg Phe Ser Gly Ser Gly Ser Gly Thr Asp Tyr Thr
1               5                   10                  15

Leu Thr Ile Ser Ser Leu Gln Pro Glu Asp Val Ala Thr Tyr Tyr Cys
            20                  25                  30

<210> SEQ ID NO 60
<211> LENGTH: 9
<212> TYPE: PRT
<213> ORGANISM: Artificial Sequence
<220> FEATURE:
<223> OTHER INFORMATION: Synthetic: Variable light chain framework
      region LC-FR4 of Mab B

<400> SEQUENCE: 60

Gly Ala Gly Thr Lys Leu Glu Leu Lys
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic: Variable light chain framework
      region LC-FR4 of Mab B variant 2 (v2), L8I

<400> SEQUENCE: 61

Gly Ala Gly Thr Lys Leu Glu Ile Lys
1               5

<210> SEQ ID NO 62
<211> LENGTH: 121
<212> TYPE: PRT
<213> ORGANISM: Artificial Sequence
<220> FEATURE:
<223> OTHER INFORMATION: Synthetic: Variable heavy chain of Mab B, (Mab
      B HC)

<400> SEQUENCE: 62

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Ile
        35                  40                  45

Gly Thr Met Trp Asn Asp Gly Asp Thr Asp Tyr His Ser Ala Leu Arg
    50                  55                  60

Ser Arg Leu Ser Ile Ser Arg Asp Ser Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg Ser Gln Leu Pro Gly Tyr Asn Leu Arg Gly Trp Phe Val Tyr Trp
```

```
                   100                 105                 110
Gly Gln Gly Thr Leu Val Ile Val Ser
            115                 120

<210> SEQ ID NO 63
<211> LENGTH: 121
<212> TYPE: PRT
<213> ORGANISM: Artificial Sequence
<220> FEATURE:
<223> OTHER INFORMATION: Synthetic: Variable heavy chain of Mab B
      variant 2, HC-FR1 Q16E, HC-FR2 I13M, HC-FR3 H2N, HC-FR3 R8K,
      HC-FR3 S15T, HC-FR3 L21F, HC-FR3 M34I, HC-FR3 F36Y, (Mab B HC v2),

<400> SEQUENCE: 63

Gln Val Gln Leu Lys Glu Ser Gly Pro Gly Leu Val Gln Pro Ser Glu
1               5                   10                  15

Thr Leu Ser Leu Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Met
        35                  40                  45

Gly Thr Met Trp Asn Asp Gly Asp Thr Asp Tyr Asn Ser Ala Leu Arg
    50                  55                  60

Ser Lys Leu Ser Ile Ser Arg Asp Thr Ser Lys Ser Gln Val Phe Leu
65              70                  75                  80

Lys Met Asn Ser Leu Gln Thr Glu Asp Thr Ala Ile Tyr Tyr Cys Ala
                85                  90                  95

Arg Ser Gln Leu Pro Gly Tyr Asn Leu Arg Gly Trp Phe Val Tyr Trp
            100                 105                 110

Gly Gln Gly Thr Leu Val Ile Val Ser
            115                 120

<210> SEQ ID NO 64
<211> LENGTH: 106
<212> TYPE: PRT
<213> ORGANISM: Artificial Sequence
<220> FEATURE:
<223> OTHER INFORMATION: Synthetic: Variable light chain of Mab B, (Mab
      B LC)

<400> SEQUENCE: 64

Asp Ile Val Met Thr Gln Thr Pro Ser Leu Leu Ser Ala Ser Val Gly
1               5                   10                  15

Asp Arg Val Thr Leu Asn Cys Lys Ala Ser His Asn Ile Asn Lys Asn
            20                  25                  30

Leu Glu Trp Tyr Gln Gln Lys Leu Gly Glu Ala Pro Lys Leu Leu Ile
        35                  40                  45

Tyr Tyr Ala Asn Asn Leu Gln Thr Gly Ile Ser Ser Arg Phe Ser Gly
    50                  55                  60

Ser Gly Ser Gly Thr Asp Tyr Thr Leu Thr Ile Ser Ser Leu Gln Pro
65              70                  75                  80

Glu Asp Val Ala Thr Tyr Tyr Cys Tyr Gln Tyr Asn Ser Gly His Thr
                85                  90                  95

Phe Gly Ala Gly Thr Lys Leu Glu Leu Lys
            100                 105

<210> SEQ ID NO 65
<211> LENGTH: 106
<212> TYPE: PRT
<213> ORGANISM: Artificial Sequence
<220> FEATURE:
```

<223> OTHER INFORMATION: Synthetic: Variable light chain of Mab B
variant 2, LC-FR1 V3Q, LC-FR1 T7S, LC-FR1 S9P, LC-FR1 L10V, LC-FR1
N22S , LC-FR3 S3P, LC-FR4 L8I, (Mab B LC v2),

<400> SEQUENCE: 65

```
Asp Ile Gln Met Thr Gln Ser Pro Pro Val Leu Ser Ala Ser Val Gly
1               5                  10                  15

Asp Arg Val Thr Leu Ser Cys Lys Ala Ser His Asn Ile Asn Lys Asn
            20                  25                  30

Leu Glu Trp Tyr Gln Gln Lys Leu Gly Glu Ala Pro Lys Leu Leu Ile
        35                  40                  45

Tyr Tyr Ala Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Asn Ser Gly His Thr
                85                  90                  95

Phe Gly Ala Gly Thr Lys Leu Glu Ile Lys
            100                 105
```

<210> SEQ ID NO 66
<211> LENGTH: 456
<212> TYPE: PRT
<213> ORGANISM: Artificial Sequence
<220> FEATURE:
<223> OTHER INFORMATION: Synthetic: Chimeric variable heavy chain of Mab
B and canine IgG-B , (Chimeric B HC IgG-B)

<400> SEQUENCE: 66

```
Gln Val Gln Leu Lys Glu Ser Gly Pro Gly Leu Val Gln Pro Ser Gln
1               5                  10                  15

Thr Leu Ser Leu Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Ile
        35                  40                  45

Gly Thr Met Trp Asn Asp Gly Asp Thr Asp Tyr His Ser Ala Leu Arg
50                  55                  60

Ser Arg Leu Ser Ile Ser Arg Asp Ser Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg Ser Gln Leu Pro Gly Tyr Asn Leu Arg Gly Trp Phe Val Tyr Trp
            100                 105                 110

Gly Gln Gly Thr Leu Val Ile Val Ser Ala Ser Thr Thr Ala Pro Ser
        115                 120                 125

Val Phe Pro Leu Ala Pro Ser Cys Gly Ser Thr Ser Gly Ser Thr Val
130                 135                 140

Ala Leu Ala Cys Leu Val Ser Gly Tyr Phe Pro Glu Pro Val Thr Val
145                 150                 155                 160

Ser Trp Asn Ser Gly Ser Leu Thr Ser Gly Val His Thr Phe Pro Ser
                165                 170                 175

Val Leu Gln Ser Ser Gly Leu Tyr Ser Leu Ser Ser Met Val Thr Val
            180                 185                 190

Pro Ser Ser Arg Trp Pro Ser Glu Thr Phe Thr Cys Asn Val Ala His
        195                 200                 205

Pro Ala Ser Lys Thr Lys Val Asp Lys Pro Val Pro Lys Arg Glu Asn
210                 215                 220
```

```
Gly Arg Val Pro Arg Pro Asp Cys Pro Lys Cys Pro Ala Pro Glu
225                 230                 235                 240

Met Leu Gly Gly Pro Ser Val Phe Ile Phe Pro Pro Lys Pro Lys Asp
            245                 250                 255

Thr Leu Leu Ile Ala Arg Thr Pro Glu Val Thr Cys Val Val Val Asp
        260                 265                 270

Leu Asp Pro Glu Asp Pro Glu Val Gln Ile Ser Trp Phe Val Asp Gly
        275                 280                 285

Lys Gln Met Gln Thr Ala Lys Thr Gln Pro Arg Glu Glu Gln Phe Asn
290                 295                 300

Gly Thr Tyr Arg Val Val Ser Val Leu Pro Ile Gly His Gln Asp Trp
305                 310                 315                 320

Leu Lys Gly Lys Gln Phe Thr Cys Lys Val Asn Asn Lys Ala Leu Pro
            325                 330                 335

Ser Pro Ile Glu Arg Thr Ile Ser Lys Ala Arg Gly Gln Ala His Gln
            340                 345                 350

Pro Ser Val Tyr Val Leu Pro Pro Ser Arg Glu Glu Leu Ser Lys Asn
        355                 360                 365

Thr Val Ser Leu Thr Cys Leu Ile Lys Asp Phe Phe Pro Pro Asp Ile
        370                 375                 380

Asp Val Glu Trp Gln Ser Asn Gly Gln Gln Glu Pro Glu Ser Lys Tyr
385                 390                 395                 400

Arg Thr Thr Pro Pro Gln Leu Asp Glu Asp Gly Ser Tyr Phe Leu Tyr
                405                 410                 415

Ser Lys Leu Ser Val Asp Lys Ser Arg Trp Gln Arg Gly Asp Thr Phe
            420                 425                 430

Ile Cys Ala Val Met His Glu Ala Leu His Asn His Tyr Thr Gln Glu
        435                 440                 445

Ser Leu Ser His Ser Pro Gly Lys
    450                 455

<210> SEQ ID NO 67
<211> LENGTH: 457
<212> TYPE: PRT
<213> ORGANISM: Artificial Sequence
<220> FEATURE:
<223> OTHER INFORMATION: Synthetic: Chimeric variable heavy chain of Mab
      B v2 and canine IgG-B , HC-FR1 Q16E, HC-FR2 I13M, HC-FR3 H2N,
      HC-FR3 R8K, HC-FR3 S15T, HC-FR3 L21F, HC-FR3 M34I, HC-FR3 F36Y,
      (Chimeric B HC v2 IgG-B)

<400> SEQUENCE: 67

Gln Val Gln Leu Lys Glu Ser Gly Pro Gly Leu Val Gln Pro Ser Glu
1               5                   10                  15

Thr Leu Ser Leu Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Met
        35                  40                  45

Gly Thr Met Trp Asn Asp Gly Asp Thr Asp Tyr Asn Ser Ala Leu Arg
    50                  55                  60

Ser Lys Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Tyr Cys Ala
                85                  90                  95

Arg Ser Gln Leu Pro Gly Tyr Asn Leu Arg Gly Trp Phe Val Tyr Trp
            100                 105                 110
```

```
Gly Gln Gly Thr Leu Val Ile Val Ser Ala Ala Ser Thr Thr Ala Pro
            115                 120                 125

Ser Val Phe Pro Leu Ala Pro Ser Cys Gly Ser Thr Ser Gly Ser Thr
        130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
            165                 170                 175

Ser Val Leu Gln Ser Ser Gly Leu Tyr Ser Leu Ser Ser Met Val Thr
        180                 185                 190

Val Pro Ser Ser Arg Trp Pro Ser Glu Thr Phe Thr Cys Asn Val Ala
            195                 200                 205

His Pro Ala Ser Lys Thr Lys Val Asp Lys Pro Val Pro Lys Arg Glu
        210                 215                 220

Asn Gly Arg Val Pro Arg Pro Asp Cys Pro Lys Cys Pro Ala Pro
225                 230                 235                 240

Glu Met Leu Gly Gly Pro Ser Val Phe Ile Phe Pro Pro Lys Pro Lys
            245                 250                 255

Asp Thr Leu Leu Ile Ala Arg Thr Pro Glu Val Thr Cys Val Val Val
        260                 265                 270

Asp Leu Asp Pro Glu Asp Pro Glu Val Gln Ile Ser Trp Phe Val Asp
        275                 280                 285

Gly Lys Gln Met Gln Thr Ala Lys Thr Gln Pro Arg Glu Glu Gln Phe
        290                 295                 300

Asn Gly Thr Tyr Arg Val Ser Val Leu Pro Ile Gly His Gln Asp
305                 310                 315                 320

Trp Leu Lys Gly Lys Gln Phe Thr Cys Lys Val Asn Asn Lys Ala Leu
            325                 330                 335

Pro Ser Pro Ile Glu Arg Thr Ile Ser Lys Ala Arg Gly Gln Ala His
        340                 345                 350

Gln Pro Ser Val Tyr Val Leu Pro Pro Ser Arg Glu Glu Leu Ser Lys
        355                 360                 365

Asn Thr Val Ser Leu Thr Cys Leu Ile Lys Asp Phe Phe Pro Pro Asp
        370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
            405                 410                 415

Tyr Ser Lys Leu Ser Val Asp Lys Ser Arg Trp Gln Arg Gly Asp Thr
        420                 425                 430

Phe Ile Cys Ala Val Met His Glu Ala Leu His Asn His Tyr Thr Gln
        435                 440                 445

Glu Ser Leu Ser His Ser Pro Gly Lys
    450                 455

<210> SEQ ID NO 68
<211> LENGTH: 216
<212> TYPE: PRT
<213> ORGANISM: Artificial Sequence
<220> FEATURE:
<223> OTHER INFORMATION: Synthetic: Chimeric variable light chain of Mab
      B and canine kappa light constant region, (Chimeric B LC kappa)

<400> SEQUENCE: 68

Asp Ile Val Met Thr Gln Thr Pro Ser Leu Leu Ser Ala Ser Val Gly
```

```
           1               5                  10                 15
        Asp Arg Val Thr Leu Asn Cys Lys Ala Ser His Asn Ile Asn Lys Asn
                        20                 25                 30
        Leu Glu Trp Tyr Gln Gln Lys Leu Gly Glu Ala Pro Lys Leu Leu Ile
                        35                 40                 45
        Tyr Tyr Ala Asn Asn Leu Gln Thr Gly Ile Ser Ser Arg Phe Ser Gly
                        50                 55                 60
        Ser Gly Ser Gly Thr Asp Tyr Thr Leu Thr Ile Ser Ser Leu Gln Pro
         65                 70                 75                 80
        Glu Asp Val Ala Thr Tyr Tyr Cys Tyr Gln Tyr Asn Ser Gly His Thr
                             85                 90                 95
        Phe Gly Ala Gly Thr Lys Leu Glu Leu Lys Arg Asn Asp Ala Gln Pro
                           100                105                110
        Ala Val Tyr Leu Phe Gln Pro Ser Pro Asp Gln Leu His Thr Gly Ser
                       115                120                125
        Ala Ser Val Val Cys Leu Leu Asn Ser Phe Tyr Pro Lys Asp Ile Asn
         130                135                140
        Val Lys Trp Lys Val Asp Gly Val Ile Gln Asp Thr Gly Ile Gln Glu
         145                150                155                160
        Ser Val Thr Glu Gln Asp Lys Asp Ser Thr Tyr Ser Leu Ser Ser Thr
                           165                170                175
        Leu Thr Met Ser Ser Thr Glu Tyr Leu Ser His Glu Leu Tyr Ser Cys
                       180                185                190
        Glu Ile Thr His Lys Ser Leu Pro Ser Thr Leu Ile Lys Ser Phe Gln
                       195                200                205
        Arg Ser Glu Cys Gln Arg Val Asp
                       210                215
```

<210> SEQ ID NO 69
<211> LENGTH: 216
<212> TYPE: PRT
<213> ORGANISM: Artificial Sequence
<220> FEATURE:
<223> OTHER INFORMATION: Synthetic: Chimeric variable light chain of Mab
      B v2 and canine kappa light constant region, , LC-FR1 V3Q, LC-FR1
      T7S, LC-FR1 S9P, LC-FR1 L10V, LC-FR1 N22S , LC-FR3 S3P, LC-FR4
      L8I, (Chimeric B LC v2 kappa)

<400> SEQUENCE: 69

```
        Asp Ile Gln Met Thr Gln Ser Pro Pro Val Leu Ser Ala Ser Val Gly
         1               5                  10                 15
        Asp Arg Val Thr Leu Ser Cys Lys Ala Ser His Asn Ile Asn Lys Asn
                        20                 25                 30
        Leu Glu Trp Tyr Gln Gln Lys Leu Gly Glu Ala Pro Lys Leu Leu Ile
                        35                 40                 45
        Tyr Tyr Ala Asn Asn Leu Gln Thr Gly Ile Pro Ser Arg Phe Ser Gly
                        50                 55                 60
        Ser Gly Ser Gly Thr Asp Tyr Thr Leu Thr Ile Ser Ser Leu Gln Pro
         65                 70                 75                 80
        Glu Asp Val Ala Thr Tyr Tyr Cys Tyr Gln Tyr Asn Ser Gly His Thr
                             85                 90                 95
        Phe Gly Ala Gly Thr Lys Leu Glu Ile Lys Arg Asn Asp Ala Gln Pro
                           100                105                110
        Ala Val Tyr Leu Phe Gln Pro Ser Pro Asp Gln Leu His Thr Gly Ser
                       115                120                125
        Ala Ser Val Val Cys Leu Leu Asn Ser Phe Tyr Pro Lys Asp Ile Asn
```

```
                 130                 135                 140
Val Lys Trp Lys Val Asp Gly Val Ile Gln Asp Thr Gly Ile Gln Glu
145                 150                 155                 160

Ser Val Thr Glu Gln Asp Lys Asp Ser Thr Tyr Ser Leu Ser Ser Thr
                165                 170                 175

Leu Thr Met Ser Ser Thr Glu Tyr Leu Ser His Glu Leu Tyr Ser Cys
            180                 185                 190

Glu Ile Thr His Lys Ser Leu Pro Ser Thr Leu Ile Lys Ser Phe Gln
            195                 200                 205

Arg Ser Glu Cys Gln Arg Val Asp
            210                 215

<210> SEQ ID NO 70
<211> LENGTH: 475
<212> TYPE: PRT
<213> ORGANISM: Artificial Sequence
<220> FEATURE:
<223> OTHER INFORMATION: Synthetic: Chimeric variable heavy chain of Mab
      B and canine IgG-B with leader sequence, (Canine chimeric B HC
      with leader)

<400> SEQUENCE: 70

Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Gln
                20                  25                  30

Pro Ser Gln Thr Leu Ser Leu Thr Cys Thr Val Ser Gly Phe Ser Leu
            35                  40                  45

Thr Ser Tyr Gly Val Ser Trp Val Arg Gln Pro Pro Gly Lys Gly Leu
        50                  55                  60

Glu Trp Ile Gly Thr Met Trp Asn Asp Gly Asp Thr Asp Tyr His Ser
65                  70                  75                  80

Ala Leu Arg Ser Arg Leu Ser Ile Ser Arg Asp Ser Ser Lys Ser Gln
                85                  90                  95

Val Leu Leu Lys Met Asn Ser Leu Gln Thr Glu Asp Thr Ala Met Tyr
            100                 105                 110

Phe Cys Ala Arg Ser Gln Leu Pro Gly Tyr Asn Leu Arg Gly Trp Phe
        115                 120                 125

Val Tyr Trp Gly Gln Gly Thr Leu Val Ile Val Ser Ala Ser Thr Thr
    130                 135                 140

Ala Pro Ser Val Phe Pro Leu Ala Pro Ser Cys Gly Ser Thr Ser Gly
145                 150                 155                 160

Ser Thr Val Ala Leu Ala Cys Leu Val Ser Gly Tyr Phe Pro Glu Pro
                165                 170                 175

Val Thr Val Ser Trp Asn Ser Gly Ser Leu Thr Ser Gly Val His Thr
            180                 185                 190

Phe Pro Ser Val Leu Gln Ser Ser Gly Leu Tyr Ser Leu Ser Ser Met
        195                 200                 205

Val Thr Val Pro Ser Ser Arg Trp Pro Ser Glu Thr Phe Thr Cys Asn
    210                 215                 220

Val Ala His Pro Ala Ser Lys Thr Lys Val Asp Lys Pro Val Pro Lys
225                 230                 235                 240

Arg Glu Asn Gly Arg Val Pro Arg Pro Pro Asp Cys Pro Lys Cys Pro
                245                 250                 255

Ala Pro Glu Met Leu Gly Gly Pro Ser Val Phe Ile Phe Pro Pro Lys
            260                 265                 270
```

```
Pro Lys Asp Thr Leu Leu Ile Ala Arg Thr Pro Glu Val Thr Cys Val
        275                 280                 285

Val Val Asp Leu Asp Pro Glu Asp Pro Glu Val Gln Ile Ser Trp Phe
    290                 295                 300

Val Asp Gly Lys Gln Met Gln Thr Ala Lys Thr Gln Pro Arg Glu Glu
305                 310                 315                 320

Gln Phe Asn Gly Thr Tyr Arg Val Val Ser Val Leu Pro Ile Gly His
                325                 330                 335

Gln Asp Trp Leu Lys Gly Lys Gln Phe Thr Cys Lys Val Asn Asn Lys
            340                 345                 350

Ala Leu Pro Ser Pro Ile Glu Arg Thr Ile Ser Lys Ala Arg Gly Gln
        355                 360                 365

Ala His Gln Pro Ser Val Tyr Val Leu Pro Pro Ser Arg Glu Glu Leu
    370                 375                 380

Ser Lys Asn Thr Val Ser Leu Thr Cys Leu Ile Lys Asp Phe Phe Pro
385                 390                 395                 400

Pro Asp Ile Asp Val Glu Trp Gln Ser Asn Gly Gln Gln Glu Pro Glu
                405                 410                 415

Ser Lys Tyr Arg Thr Thr Pro Pro Gln Leu Asp Glu Asp Gly Ser Tyr
            420                 425                 430

Phe Leu Tyr Ser Lys Leu Ser Val Asp Lys Ser Arg Trp Gln Arg Gly
        435                 440                 445

Asp Thr Phe Ile Cys Ala Val Met His Glu Ala Leu His Asn His Tyr
    450                 455                 460

Thr Gln Glu Ser Leu Ser His Ser Pro Gly Lys
465                 470                 475
```

<210> SEQ ID NO 71
<211> LENGTH: 476
<212> TYPE: PRT
<213> ORGANISM: Artificial Sequence
<220> FEATURE:
<223> OTHER INFORMATION: Synthetic: Chimeric variable heavy chain of Mab
      B v2 and canine IgG-B with leader sequence, HC-FR1 Q16E, HC-FR2
      I13M, HC-FR3 H2N, HC-FR3 R8K, HC-FR3 S15T, HC-FR3 L21F, HC-FR3
      M34I, HC-FR3 F36Y, (Canine chimeric B HC v2 IgG-B with leader),

<400> SEQUENCE: 71

```
Met Ala Val Leu Gly Leu Leu Cys Leu Val Thr Phe Pro Ser Cys
1               5                   10                  15

Val Leu Ser Gln Val Gln Leu Lys Glu Ser Gly Pro Gly Leu Val Gln
            20                  25                  30

Pro Ser Glu Thr Leu Ser Leu Thr Cys Thr Val Ser Gly Phe Ser Leu
        35                  40                  45

Thr Ser Tyr Gly Val Ser Trp Val Arg Gln Pro Pro Gly Lys Gly Leu
    50                  55                  60

Glu Trp Met Gly Thr Met Trp Asn Asp Gly Asp Thr Asp Tyr Asn Ser
65                  70                  75                  80

Ala Leu Arg Ser Lys Leu Ser Ile Ser Arg Asp Thr Ser Lys Ser Gln
                85                  90                  95

Val Phe Leu Lys Met Asn Ser Leu Gln Thr Glu Asp Thr Ala Ile Tyr
            100                 105                 110

Tyr Cys Ala Arg Ser Gln Leu Pro Gly Tyr Asn Leu Arg Gly Trp Phe
        115                 120                 125

Val Tyr Trp Gly Gln Gly Thr Leu Val Ile Val Ser Ala Ala Ser Thr
    130                 135                 140
```

Thr Ala Pro Ser Val Phe Pro Leu Ala Pro Ser Cys Gly Ser Thr Ser
145                 150                 155                 160

Gly Ser Thr Val Ala Leu Ala Cys Leu Val Ser Gly Tyr Phe Pro Glu
                165                 170                 175

Pro Val Thr Val Ser Trp Asn Ser Gly Ser Leu Thr Ser Gly Val His
            180                 185                 190

Thr Phe Pro Ser Val Leu Gln Ser Ser Gly Leu Tyr Ser Leu Ser Ser
        195                 200                 205

Met Val Thr Val Pro Ser Ser Arg Trp Pro Ser Glu Thr Phe Thr Cys
210                 215                 220

Asn Val Ala His Pro Ala Ser Lys Thr Lys Val Asp Lys Pro Val Pro
225                 230                 235                 240

Lys Arg Glu Asn Gly Arg Val Pro Arg Pro Asp Cys Pro Lys Cys
                245                 250                 255

Pro Ala Pro Glu Met Leu Gly Gly Pro Ser Val Phe Ile Phe Pro Pro
                260                 265                 270

Lys Pro Lys Asp Thr Leu Leu Ile Ala Arg Thr Pro Glu Val Thr Cys
            275                 280                 285

Val Val Val Asp Leu Asp Pro Glu Asp Pro Glu Val Gln Ile Ser Trp
        290                 295                 300

Phe Val Asp Gly Lys Gln Met Gln Thr Ala Lys Thr Gln Pro Arg Glu
305                 310                 315                 320

Glu Gln Phe Asn Gly Thr Tyr Arg Val Val Ser Val Leu Pro Ile Gly
                325                 330                 335

His Gln Asp Trp Leu Lys Gly Lys Gln Phe Thr Cys Lys Val Asn Asn
                340                 345                 350

Lys Ala Leu Pro Ser Pro Ile Glu Arg Thr Ile Ser Lys Ala Arg Gly
            355                 360                 365

Gln Ala His Gln Pro Ser Val Tyr Val Leu Pro Pro Ser Arg Glu Glu
        370                 375                 380

Leu Ser Lys Asn Thr Val Ser Leu Thr Cys Leu Ile Lys Asp Phe Phe
385                 390                 395                 400

Pro Pro Asp Ile Asp Val Glu Trp Gln Ser Asn Gly Gln Gln Glu Pro
                405                 410                 415

Glu Ser Lys Tyr Arg Thr Thr Pro Pro Gln Leu Asp Glu Asp Gly Ser
                420                 425                 430

Tyr Phe Leu Tyr Ser Lys Leu Ser Val Asp Lys Ser Arg Trp Gln Arg
            435                 440                 445

Gly Asp Thr Phe Ile Cys Ala Val Met His Glu Ala Leu His Asn His
        450                 455                 460

Tyr Thr Gln Glu Ser Leu Ser His Ser Pro Gly Lys
465                 470                 475

<210> SEQ ID NO 72
<211> LENGTH: 236
<212> TYPE: PRT
<213> ORGANISM: Artificial Sequence
<220> FEATURE:
<223> OTHER INFORMATION: Synthetic: Chimeric variable light chain of Mab
      B and canine kappa light constant region with leader sequence,
      (Canine chimeric B LC kappa with leader)

<400> SEQUENCE: 72

Met Glu Thr Asp Thr Leu Leu Leu Trp Val Leu Leu Leu Trp Val Pro
1               5                   10                  15

```
Gly Ser Thr Gly Asp Ile Val Met Thr Gln Thr Pro Ser Leu Leu Ser
            20                  25                  30

Ala Ser Val Gly Asp Arg Val Thr Leu Asn Cys Lys Ala Ser His Asn
        35                  40                  45

Ile Asn Lys Asn Leu Glu Trp Tyr Gln Gln Lys Leu Gly Glu Ala Pro
 50                  55                  60

Lys Leu Leu Ile Tyr Tyr Ala Asn Asn Leu Gln Thr Gly Ile Ser Ser
 65              70                  75                  80

Arg Phe Ser Gly Ser Gly Ser Gly Thr Asp Tyr Thr Leu Thr Ile Ser
                85                  90                  95

Ser Leu Gln Pro Glu Asp Val Ala Thr Tyr Tyr Cys Tyr Gln Tyr Asn
                100                 105                 110

Ser Gly His Thr Phe Gly Ala Gly Thr Lys Leu Glu Leu Lys Arg Asn
            115                 120                 125

Asp Ala Gln Pro Ala Val Tyr Leu Phe Gln Pro Ser Pro Asp Gln Leu
            130                 135             140

His Thr Gly Ser Ala Ser Val Val Cys Leu Leu Asn Ser Phe Tyr Pro
145                 150                 155                 160

Lys Asp Ile Asn Val Lys Trp Lys Val Asp Gly Val Ile Gln Asp Thr
                165                 170                 175

Gly Ile Gln Glu Ser Val Thr Glu Gln Asp Lys Asp Ser Thr Tyr Ser
            180                 185                 190

Leu Ser Ser Thr Leu Thr Met Ser Ser Thr Glu Tyr Leu Ser His Glu
        195                 200                 205

Leu Tyr Ser Cys Glu Ile Thr His Lys Ser Leu Pro Ser Thr Leu Ile
    210                 215                 220

Lys Ser Phe Gln Arg Ser Glu Cys Gln Arg Val Asp
225                 230                 235

<210> SEQ ID NO 73
<211> LENGTH: 236
<212> TYPE: PRT
<213> ORGANISM: Artificial Sequence
<220> FEATURE:
<223> OTHER INFORMATION: Synthetic: Chimeric variable light chain of Mab
      B v2 and canine kappa light constant region with leader sequence,
      , LC-FR1 V3Q, LC-FR1 T7S, LC-FR1 S9P, LC-FR1 L10V, LC-FR1 N22S ,
      LC-FR3 S3P, LC-FR4 L8I, (Canine chimeric B LC v2 kappa with
      leader)

<400> SEQUENCE: 73

Met Glu Thr Asp Thr Leu Leu Leu Trp Val Leu Leu Leu Trp Val Pro
 1               5                  10                  15

Gly Ser Thr Gly Asp Ile Gln Met Thr Gln Ser Pro Pro Val Leu Ser
            20                  25                  30

Ala Ser Val Gly Asp Arg Val Thr Leu Ser Cys Lys Ala Ser His Asn
        35                  40                  45

Ile Asn Lys Asn Leu Glu Trp Tyr Gln Gln Lys Leu Gly Glu Ala Pro
 50                  55                  60

Lys Leu Leu Ile Tyr Tyr Ala Asn Asn Leu Gln Thr Gly Ile Pro Ser
 65              70                  75                  80

Arg Phe Ser Gly Ser Gly Ser Gly Thr Asp Tyr Thr Leu Thr Ile Ser
                85                  90                  95

Ser Leu Gln Pro Glu Asp Val Ala Thr Tyr Tyr Cys Tyr Gln Tyr Asn
                100                 105                 110

Ser Gly His Thr Phe Gly Ala Gly Thr Lys Leu Glu Ile Lys Arg Asn
            115                 120                 125
```

```
Asp Ala Gln Pro Ala Val Tyr Leu Phe Gln Pro Ser Pro Asp Gln Leu
            130                 135                 140

His Thr Gly Ser Ala Ser Val Val Cys Leu Leu Asn Ser Phe Tyr Pro
145                 150                 155                 160

Lys Asp Ile Asn Val Lys Trp Lys Val Asp Gly Val Ile Gln Asp Thr
                165                 170                 175

Gly Ile Gln Glu Ser Val Thr Glu Gln Asp Lys Asp Ser Thr Tyr Ser
                180                 185                 190

Leu Ser Ser Thr Leu Thr Met Ser Ser Thr Glu Tyr Leu Ser His Glu
            195                 200                 205

Leu Tyr Ser Cys Glu Ile Thr His Lys Ser Leu Pro Ser Thr Leu Ile
        210                 215                 220

Lys Ser Phe Gln Arg Ser Glu Cys Gln Arg Val Asp
225                 230                 235

<210> SEQ ID NO 74
<211> LENGTH: 456
<212> TYPE: PRT
<213> ORGANISM: Artificial Sequence
<220> FEATURE:
<223> OTHER INFORMATION: Synthetic: Chimeric variable heavy chain of Mab
      B and feline IgG-1, (Feline chimeric B HC IgG-1)

<400> SEQUENCE: 74

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Ile
        35                  40                  45

Gly Thr Met Trp Asn Asp Gly Asp Thr Asp Tyr His Ser Ala Leu Arg
    50                  55                  60

Ser Arg Leu Ser Ile Ser Arg Asp Ser Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg Ser Gln Leu Pro Gly Tyr Asn Leu Arg Gly Trp Phe Val Tyr Trp
            100                 105                 110

Gly Gln Gly Thr Leu Val Ile Val Ser Ala Ser Thr Thr Ala Pro Ser
        115                 120                 125

Val Phe Pro Leu Ala Pro Ser Cys Gly Thr Thr Ser Gly Ala Thr Val
    130                 135                 140

Ala Leu Ala Cys Leu Val Leu Gly Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ala Ser Gly Leu Tyr Ser Leu Ser Ser Met Val Thr Val
            180                 185                 190

Pro Ser Ser Arg Trp Leu Ser Asp Thr Phe Thr Cys Asn Val Ala His
        195                 200                 205

Pro Pro Ser Asn Thr Lys Val Asp Lys Thr Val Arg Lys Thr Asp His
    210                 215                 220

Pro Pro Gly Pro Lys Pro Cys Asp Cys Pro Lys Cys Pro Pro Pro Glu
225                 230                 235                 240

Met Leu Gly Gly Pro Ser Ile Phe Ile Phe Pro Pro Lys Pro Lys Asp
```

```
                    245                 250                 255

Thr Leu Ser Ile Ser Arg Thr Pro Glu Val Thr Cys Leu Val Val Asp
            260                 265                 270

Leu Gly Pro Asp Asp Ser Asp Val Gln Ile Thr Trp Phe Val Asp Asn
        275                 280                 285

Thr Gln Val Tyr Thr Ala Lys Thr Ser Pro Arg Glu Glu Gln Phe Asn
    290                 295                 300

Ser Thr Tyr Arg Val Val Ser Val Leu Pro Ile Leu His Gln Asp Trp
305                 310                 315                 320

Leu Lys Gly Lys Glu Phe Lys Cys Lys Val Asn Ser Lys Ser Leu Pro
            325                 330                 335

Ser Pro Ile Glu Arg Thr Ile Ser Lys Ala Lys Gly Gln Pro His Glu
        340                 345                 350

Pro Gln Val Tyr Val Leu Pro Pro Ala Gln Glu Glu Leu Ser Arg Asn
    355                 360                 365

Lys Val Ser Val Thr Cys Leu Ile Lys Ser Phe His Pro Pro Asp Ile
370                 375                 380

Ala Val Glu Trp Glu Ile Thr Gly Gln Pro Glu Pro Glu Asn Asn Tyr
385                 390                 395                 400

Arg Thr Thr Pro Pro Gln Leu Asp Ser Asp Gly Thr Tyr Phe Val Tyr
                405                 410                 415

Ser Lys Leu Ser Val Asp Arg Ser His Trp Gln Arg Gly Asn Thr Tyr
            420                 425                 430

Thr Cys Ser Val Ser His Glu Ala Leu His Ser His His Thr Gln Lys
        435                 440                 445

Ser Leu Thr Gln Ser Pro Gly Lys
    450                 455

<210> SEQ ID NO 75
<211> LENGTH: 216
<212> TYPE: PRT
<213> ORGANISM: Artificial Sequence
<220> FEATURE:
<223> OTHER INFORMATION: Synthetic: Chimeric variable light chain of Mab
      B and feline kappa light constant region , (Feline chimeric B LC
      kappa)

<400> SEQUENCE: 75

Asp Ile Val Met Thr Gln Thr Pro Ser Leu Leu Ser Ala Ser Val Gly
1               5                   10                  15

Asp Arg Val Thr Leu Asn Cys Lys Ala Ser His Asn Ile Asn Lys Asn
            20                  25                  30

Leu Glu Trp Tyr Gln Gln Lys Leu Gly Glu Ala Pro Lys Leu Leu Ile
        35                  40                  45

Tyr Tyr Ala Asn Asn Leu Gln Thr Gly Ile Ser Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Asn Ser Gly His Thr
                85                  90                  95

Phe Gly Ala Gly Thr Lys Leu Glu Leu Lys Arg Ser Asp Ala Gln Pro
            100                 105                 110

Ser Val Phe Leu Phe Gln Pro Ser Leu Asp Glu Leu His Thr Gly Ser
        115                 120                 125

Ala Ser Ile Val Cys Ile Leu Asn Asp Phe Tyr Pro Lys Glu Val Asn
    130                 135                 140
```

```
Val Lys Trp Lys Val Asp Gly Val Val Gln Asn Lys Gly Ile Gln Glu
145                 150                 155                 160

Ser Thr Thr Glu Gln Asn Ser Lys Asp Ser Thr Tyr Ser Leu Ser Ser
                165                 170                 175

Thr Leu Thr Met Ser Ser Thr Glu Tyr Gln Ser His Glu Lys Phe Ser
            180                 185                 190

Cys Glu Val Thr His Lys Ser Leu Ala Ser Thr Leu Val Lys Ser Phe
        195                 200                 205

Asn Arg Ser Glu Cys Gln Arg Glu
    210                 215
```

<210> SEQ ID NO 76
<211> LENGTH: 216
<212> TYPE: PRT
<213> ORGANISM: Artificial Sequence
<220> FEATURE:
<223> OTHER INFORMATION: Synthetic: Chimeric variable light chain of Mab
      B and feline kappa light constant region with no N-linked
      glycosylation site, (Feline chimeric B LC kappa aglycos)

<400> SEQUENCE: 76

```
Asp Ile Val Met Thr Gln Thr Pro Ser Leu Leu Ser Ala Ser Val Gly
1               5                   10                  15

Asp Arg Val Thr Leu Asn Cys Lys Ala Ser His Asn Ile Asn Lys Asn
                20                  25                  30

Leu Glu Trp Tyr Gln Gln Lys Leu Gly Glu Ala Pro Lys Leu Leu Ile
            35                  40                  45

Tyr Tyr Ala Asn Asn Leu Gln Thr Gly Ile Ser Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Asn Ser Gly His Thr
                85                  90                  95

Phe Gly Ala Gly Thr Lys Leu Glu Leu Lys Arg Ser Asp Ala Gln Pro
            100                 105                 110

Ser Val Phe Leu Phe Gln Pro Ser Leu Asp Glu Leu His Thr Gly Ser
        115                 120                 125

Ala Ser Ile Val Cys Ile Leu Asn Asp Phe Tyr Pro Lys Glu Val Asn
130                 135                 140

Val Lys Trp Lys Val Asp Gly Val Val Gln Asn Lys Gly Ile Gln Glu
145                 150                 155                 160

Ser Thr Thr Glu Gln Asn Ser Lys Asp Ser Thr Tyr Ser Leu Ser Ser
                165                 170                 175

Thr Leu Thr Met Ser Ser Thr Glu Tyr Gln Ser His Glu Lys Phe Ser
            180                 185                 190

Cys Glu Val Thr His Lys Ser Leu Ala Ser Thr Leu Val Lys Ser Phe
        195                 200                 205

Gln Arg Ser Glu Cys Gln Arg Glu
    210                 215
```

<210> SEQ ID NO 77
<211> LENGTH: 476
<212> TYPE: PRT
<213> ORGANISM: Artificial Sequence
<220> FEATURE:
<223> OTHER INFORMATION: Synthetic: Caninized variable heavy chain of
      Mab B v3 and canine IgG-B with leader sequence, (Caninized B HC v3
      IgG-B with leader)

<400> SEQUENCE: 77

```
Met Ala Val Leu Gly Leu Leu Cys Leu Val Thr Phe Pro Ser Cys
1               5                   10                  15

Val Leu Ser Glu Val Gln Leu Val Glu Ser Gly Gly Asp Leu Val Lys
            20                  25                  30

Pro Gly Gly Thr Leu Arg Leu Ser Cys Thr Val Ser Gly Phe Ser Leu
            35                  40                  45

Thr Ser Tyr Gly Val Ser Trp Val Arg Gln Ser Pro Gly Lys Gly Leu
50                  55                  60

Glu Trp Ile Gly Thr Met Trp Asn Asp Gly Asp Thr Asp Tyr His Ser
65                  70                  75                  80

Ala Val Lys Gly Gln Leu Ser Ile Ser Arg Asp Thr Ser Lys Ser Gln
                85                  90                  95

Val Phe Leu Gln Met Asn Ser Leu Arg Ala Glu Asp Thr Ala Met Tyr
            100                 105                 110

Tyr Cys Ala Arg Ser Gln Leu Pro Gly Tyr Asn Leu Arg Gly Trp Phe
            115                 120                 125

Val Tyr Trp Gly Gln Gly Thr Leu Val Thr Val Ser Ser Ala Ser Thr
130                 135                 140

Thr Ala Pro Ser Val Phe Pro Leu Ala Pro Ser Cys Gly Ser Thr Ser
145                 150                 155                 160

Gly Ser Thr Val Ala Leu Ala Cys Leu Val Ser Gly Tyr Phe Pro Glu
                165                 170                 175

Pro Val Thr Val Ser Trp Asn Ser Gly Ser Leu Thr Ser Gly Val His
            180                 185                 190

Thr Phe Pro Ser Val Leu Gln Ser Ser Gly Leu Tyr Ser Leu Ser Ser
            195                 200                 205

Met Val Thr Val Pro Ser Ser Arg Trp Pro Ser Glu Thr Phe Thr Cys
210                 215                 220

Asn Val Ala His Pro Ala Ser Lys Thr Lys Val Asp Lys Pro Val Pro
225                 230                 235                 240

Lys Arg Glu Asn Gly Arg Val Pro Arg Pro Pro Asp Cys Pro Lys Cys
                245                 250                 255

Pro Ala Pro Glu Met Leu Gly Gly Pro Ser Val Phe Ile Phe Pro Pro
            260                 265                 270

Lys Pro Lys Asp Thr Leu Leu Ile Ala Arg Thr Pro Glu Val Thr Cys
            275                 280                 285

Val Val Val Asp Leu Asp Pro Glu Asp Pro Glu Val Gln Ile Ser Trp
290                 295                 300

Phe Val Asp Gly Lys Gln Met Gln Thr Ala Lys Thr Gln Pro Arg Glu
305                 310                 315                 320

Glu Gln Phe Asn Gly Thr Tyr Arg Val Val Ser Val Leu Pro Ile Gly
                325                 330                 335

His Gln Asp Trp Leu Lys Gly Lys Gln Phe Thr Cys Lys Val Asn Asn
            340                 345                 350

Lys Ala Leu Pro Ser Pro Ile Glu Arg Thr Ile Ser Lys Ala Arg Gly
            355                 360                 365

Gln Ala His Gln Pro Ser Val Tyr Val Leu Pro Pro Ser Arg Glu Glu
370                 375                 380

Leu Ser Lys Asn Thr Val Ser Leu Thr Cys Leu Ile Lys Asp Phe Phe
385                 390                 395                 400

Pro Pro Asp Ile Asp Val Glu Trp Gln Ser Asn Gly Gln Gln Glu Pro
```

```
                    405                 410                 415
Glu Ser Lys Tyr Arg Thr Thr Pro Gln Leu Asp Glu Asp Gly Ser
            420                 425                 430

Tyr Phe Leu Tyr Ser Lys Leu Ser Val Asp Lys Ser Arg Trp Gln Arg
        435                 440                 445

Gly Asp Thr Phe Ile Cys Ala Val Met His Glu Ala Leu His Asn His
    450                 455                 460

Tyr Thr Gln Glu Ser Leu Ser His Ser Pro Gly Lys
465                 470                 475

<210> SEQ ID NO 78
<211> LENGTH: 236
<212> TYPE: PRT
<213> ORGANISM: Artificial Sequence
<220> FEATURE:
<223> OTHER INFORMATION: Synthetic: Caninized variable light chain of
      Mab B v3 and canine kappa light constant region with leader
      sequence, (Caninized B LC kappa with leader)

<400> SEQUENCE: 78

Met Glu Thr Asp Thr Leu Leu Leu Trp Val Leu Leu Leu Trp Val Pro
1               5                   10                  15

Gly Ser Thr Gly Glu Ile Val Leu Thr Gln Ser Pro Ala Ser Leu Ala
            20                  25                  30

Val Ser Leu Gly Gln Arg Ala Thr Ile Ser Cys Lys Ala Ser His Asn
        35                  40                  45

Ile Asn Lys Asn Leu Glu Trp Tyr Gln Gln Lys Pro Gly Gln Pro Pro
    50                  55                  60

Lys Leu Leu Ile Tyr Tyr Ala Asn Asn Leu Gln Thr Gly Val Pro Ala
65                  70                  75                  80

Arg Phe Ser Gly Ser Gly Ser Gly Thr Asp Tyr Ser Leu Asn Ile His
                85                  90                  95

Pro Met Glu Glu Asp Asp Thr Ala Met Tyr Tyr Cys Tyr Gln Tyr Asn
            100                 105                 110

Ser Gly His Thr Phe Gly Gly Gly Thr Lys Leu Glu Ile Lys Arg Asn
        115                 120                 125

Asp Ala Gln Pro Ala Val Tyr Leu Phe Gln Pro Ser Pro Asp Gln Leu
    130                 135                 140

His Thr Gly Ser Ala Ser Val Val Cys Leu Leu Asn Ser Phe Tyr Pro
145                 150                 155                 160

Lys Asp Ile Asn Val Lys Trp Lys Val Asp Gly Val Ile Gln Asp Thr
                165                 170                 175

Gly Ile Gln Glu Ser Val Thr Glu Gln Asp Lys Asp Ser Thr Tyr Ser
            180                 185                 190

Leu Ser Ser Thr Leu Thr Met Ser Ser Thr Glu Tyr Leu Ser His Glu
        195                 200                 205

Leu Tyr Ser Cys Glu Ile Thr His Lys Ser Leu Pro Ser Thr Leu Ile
    210                 215                 220

Lys Ser Phe Gln Arg Ser Glu Cys Gln Arg Val Asp
225                 230                 235

<210> SEQ ID NO 79
<211> LENGTH: 457
<212> TYPE: PRT
<213> ORGANISM: Artificial Sequence
<220> FEATURE:
<223> OTHER INFORMATION: Synthetic: Caninized variable heavy chain of
      Mab B v3 and canine IgG-B , (Caninized B HC v3 IgG-B)
```

<400> SEQUENCE: 79

```
Glu Val Gln Leu Val Glu Ser Gly Gly Asp Leu Val Lys Pro Gly Gly
1               5                   10                  15

Thr Leu Arg Leu Ser Cys Thr Val Ser Gly Phe Ser Leu Thr Ser Tyr
            20                  25                  30

Gly Val Ser Trp Val Arg Gln Ser Pro Gly Lys Gly Leu Glu Trp Ile
        35                  40                  45

Gly Thr Met Trp Asn Asp Gly Asp Thr Asp Tyr His Ser Ala Val Lys
    50                  55                  60

Gly Gln Leu Ser Ile Ser Arg Asp Thr Ser Lys Ser Gln Val Phe Leu
65                  70                  75                  80

Gln Met Asn Ser Leu Arg Ala Glu Asp Thr Ala Met Tyr Tyr Cys Ala
                85                  90                  95

Arg Ser Gln Leu Pro Gly Tyr Asn Leu Arg Gly Trp Phe Val Tyr Trp
            100                 105                 110

Gly Gln Gly Thr Leu Val Thr Val Ser Ser Ala Ser Thr Ala Pro
        115                 120                 125

Ser Val Phe Pro Leu Ala Pro Ser Cys Gly Ser Thr Ser Gly Ser Thr
130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
    210                 215                 220

Asn Gly Arg Val Pro Arg Pro Asp Cys Pro Lys Cys Pro Ala Pro
225                 230                 235                 240

Glu Met Leu Gly Gly Pro Ser Val Phe Ile Phe Pro Pro Lys Pro Lys
                245                 250                 255

Asp Thr Leu Leu Ile Ala Arg Thr Pro Glu Val Thr Cys Val Val Val
            260                 265                 270

Asp Leu Asp Pro Glu Asp Pro Glu Val Gln Ile Ser Trp Phe Val Asp
        275                 280                 285

Gly Lys Gln Met Gln Thr Ala Lys Thr Gln Pro Arg Glu Glu Gln Phe
    290                 295                 300

Asn Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
        355                 360                 365

Asn Thr Val Ser Leu Thr Cys Leu Ile Lys Asp Phe Phe Pro Pro Asp
    370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
```

```
                    405                 410                 415
Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
            435                 440                 445

Glu Ser Leu Ser His Ser Pro Gly Lys
            450                 455

<210> SEQ ID NO 80
<211> LENGTH: 216
<212> TYPE: PRT
<213> ORGANISM: Artificial Sequence
<220> FEATURE:
<223> OTHER INFORMATION: Synthetic: Caninized variable light chain of
      Mab B v3 and canine kappa light constant region, (Caninized B LC
      v3 kappa)

<400> SEQUENCE: 80

Glu Ile Val Leu Thr Gln Ser Pro Ala Ser Leu Ala Val Ser Leu Gly
1               5                   10                  15

Gln Arg Ala Thr Ile Ser Cys Lys Ala Ser His Asn Ile Asn Lys Asn
            20                  25                  30

Leu Glu Trp Tyr Gln Gln Lys Pro Gly Gln Pro Pro Lys Leu Leu Ile
        35                  40                  45

Tyr Tyr Ala Asn Asn Leu Gln Thr Gly Val Pro Ala Arg Phe Ser Gly
    50                  55                  60

Ser Gly Ser Gly Thr Asp Tyr Ser Leu Asn Ile His Pro Met Glu Glu
65                  70                  75                  80

Asp Asp Thr Ala Met Tyr Tyr Cys Tyr Gln Tyr Asn Ser Gly His Thr
                85                  90                  95

Phe Gly Gly Gly Thr Lys Leu Glu Ile Lys Arg Asn Asp Ala Gln Pro
            100                 105                 110

Ala Val Tyr Leu Phe Gln Pro Ser Pro Asp Gln Leu His Thr Gly Ser
        115                 120                 125

Ala Ser Val Val Cys Leu Leu Asn Ser Phe Tyr Pro Lys Asp Ile Asn
    130                 135                 140

Val Lys Trp Lys Val Asp Gly Val Ile Gln Asp Thr Gly Ile Gln Glu
145                 150                 155                 160

Ser Val Thr Glu Gln Asp Lys Asp Ser Thr Tyr Ser Leu Ser Ser Thr
                165                 170                 175

Leu Thr Met Ser Ser Thr Glu Tyr Leu Ser His Glu Leu Tyr Ser Cys
            180                 185                 190

Glu Ile Thr His Lys Ser Leu Pro Ser Thr Leu Ile Lys Ser Phe Gln
        195                 200                 205

Arg Ser Glu Cys Gln Arg Val Asp
    210                 215

<210> SEQ ID NO 81
<211> LENGTH: 114
<212> TYPE: PRT
<213> ORGANISM: Artificial Sequence
<220> FEATURE:
<223> OTHER INFORMATION: Synthetic: Mab E variable HC

<400> SEQUENCE: 81

Gly Pro Gly Leu Val Gln Pro Ser Gln Thr Leu Ser Leu Thr Cys Thr
1               5                   10                  15

Val Ser Gly Phe Ser Leu Ser Ser Tyr His Val His Trp Val Arg Gln
```

```
                20                  25                  30
Pro Pro Gly Lys Gly Leu Glu Trp Leu Gly Val Met Trp Asn Asp Gly
            35                  40                  45

Asp Thr Ser Tyr Asn Leu Ala Leu Asn Ser Arg Leu Ser Ile Ser Arg
50                  55                  60

Asp Thr Ser Lys Ser Gln Val Phe Phe Lys Met Ser Ser Leu Gln Thr
65                  70                  75                  80

Glu Asp Thr Ala Thr Tyr Tyr Cys Ala Arg Pro Glu Leu Pro Gly Leu
                85                  90                  95

Thr Tyr Gly Val Trp Phe Pro Tyr Trp Gly Gln Gly Thr Leu Val Thr
            100                 105                 110

Val Ser

<210> SEQ ID NO 82
<211> LENGTH: 101
<212> TYPE: PRT
<213> ORGANISM: Artificial Sequence
<220> FEATURE:
<223> OTHER INFORMATION: Synthetic: Mab E variable LC

<400> SEQUENCE: 82

Ala Ser Met Ser Ile Ser Val Gly Asp Arg Val Thr Met Asn Cys Lys
1               5                   10                  15

Ala Ser Gln Asn Val Asp Ser Asn Val Asp Trp Tyr Gln Gln Lys Thr
            20                  25                  30

Gly Gln Ser Pro Asn Leu Leu Ile Tyr Lys Ala Ser Asn Arg Asn Thr
        35                  40                  45

Gly Val Pro Asp Arg Phe Thr Gly Ser Gly Ser Gly Thr Asp Phe Thr
50                  55                  60

Phe Thr Ile Ser Asn Met Gln Ala Glu Asp Leu Ala Val Tyr Tyr Cys
65                  70                  75                  80

Met Gln Ser Thr Ser Tyr Pro Leu Thr Phe Gly Ser Gly Thr Lys Leu
                85                  90                  95

Glu Ile Lys Arg Ala
            100

<210> SEQ ID NO 83
<211> LENGTH: 114
<212> TYPE: PRT
<213> ORGANISM: Artificial Sequence
<220> FEATURE:
<223> OTHER INFORMATION: Synthetic: Mab F variable HC

<400> SEQUENCE: 83

Gly Pro Gly Leu Val Gln Pro Ser Gln Thr Leu Ser Leu Thr Cys Thr
1               5                   10                  15

Val Ser Gly Phe Ser Leu Thr Ser Tyr Gly Val Ser Trp Val Arg Gln
            20                  25                  30

Pro Pro Gly Lys Gly Leu Glu Trp Ile Gly Thr Met Trp Asn Asp Gly
            35                  40                  45

Asp Thr Asp Tyr His Ser Ala Leu Arg Ser Arg Leu Ser Ile Ser Arg
50                  55                  60

Asp Ser Ser Lys Ser Gln Val Leu Leu Lys Met Asn Ser Leu Gln Thr
65                  70                  75                  80

Glu Asp Thr Ala Met Tyr Phe Cys Ala Arg Ser Gln Leu Pro Gly Tyr
                85                  90                  95

Asn Leu Arg Gly Trp Phe Val Tyr Trp Gly Gln Gly Thr Leu Val Ile
```

-continued

```
                     100                 105                 110

Val Ser

<210> SEQ ID NO 84
<211> LENGTH: 100
<212> TYPE: PRT
<213> ORGANISM: Artificial Sequence
<220> FEATURE:
<223> OTHER INFORMATION: Synthetic: Mab F variable LC

<400> SEQUENCE: 84

Ser Leu Leu Ser Ala Ser Val Gly Asp Arg Val Thr Leu Asn Cys Lys
1               5                   10                  15

Ala Ser His Asn Ile Asn Lys Asn Leu Glu Trp Tyr Gln Gln Lys Leu
            20                  25                  30

Gly Glu Ala Pro Lys Leu Leu Ile Tyr Tyr Ala Asn Asn Leu Gln Thr
        35                  40                  45

Gly Ile Ser Ser Arg Phe Ser Gly Ser Gly Ser Gly Thr Asp Tyr Thr
    50                  55                  60

Leu Thr Ile Ser Ser Leu Gln Pro Glu Asp Val Ala Thr Tyr Tyr Cys
65                  70                  75                  80

Tyr Gln Tyr Asn Ser Gly His Thr Phe Gly Ala Gly Thr Lys Leu Glu
                85                  90                  95

Leu Lys Arg Ala
            100

<210> SEQ ID NO 85
<211> LENGTH: 122
<212> TYPE: PRT
<213> ORGANISM: Artificial Sequence
<220> FEATURE:
<223> OTHER INFORMATION: Synthetic: Caninized variable heavy chain of
      Mab A v3

<400> SEQUENCE: 85

Gln Val Gln Leu Val Glu Ser Gly Gly Asp Leu Val Lys Pro Gly Gly
1               5                   10                  15

Thr Leu Arg Leu Ser Cys Thr Val Ser Gly Phe Ser Leu Ser Ser Tyr
            20                  25                  30

His Val His Trp Val Arg Gln Pro Pro Gly Lys Gly Leu Glu Trp Val
        35                  40                  45

Ala Val Met Trp Asn Asp Gly Asp Thr Ser Tyr Asn Leu Ala Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Pro Glu Leu Pro Gly Leu Thr Tyr Gly Val Trp Phe Pro Tyr Trp
            100                 105                 110

Gly Gln Gly Thr Leu Val Thr Val Ser Ser
        115                 120

<210> SEQ ID NO 86
<211> LENGTH: 122
<212> TYPE: PRT
<213> ORGANISM: Artificial Sequence
<220> FEATURE:
<223> OTHER INFORMATION: Synthetic: Caninized variable heavy chain of
      Mab A v4
```

```
<400> SEQUENCE: 86

Glu Val Gln Leu Val Glu Ser Gly Gly Asp Leu Val Lys Pro Gly Gly
1               5                   10                  15

Thr Leu Arg Leu Ser Cys Thr Val Ser Gly Phe Ser Leu Ser Ser Tyr
            20                  25                  30

His Val His Trp Val Arg Gln Pro Pro Gly Lys Gly Leu Glu Trp Leu
        35                  40                  45

Gly Val Met Trp Asn Asp Gly Asp Thr Ser Tyr Asn Leu Ala Val Lys
    50                  55                  60

Gly Arg Phe Thr Ile Ser Arg Asp Asn Ala Lys Asn Thr Leu Tyr Phe
65                  70                  75                  80

Gln Met Asn Ser Leu Arg Ala Glu Asp Thr Ala Thr Tyr Tyr Cys Ala
                85                  90                  95

Arg Pro Glu Leu Pro Gly Leu Thr Tyr Gly Val Trp Phe Pro Tyr Trp
            100                 105                 110

Gly Gln Gly Thr Leu Val Thr Val Ser Ser
        115                 120

<210> SEQ ID NO 87
<211> LENGTH: 107
<212> TYPE: PRT
<213> ORGANISM: Artificial Sequence
<220> FEATURE:
<223> OTHER INFORMATION: Synthetic: Caninized variable light chain of
      Mab A

<400> SEQUENCE: 87

Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Asn Val Asp Ser Asn
            20                  25                  30

Val Asp Trp Tyr Gln Gln Lys Pro Gly Gln Ala Pro Lys Leu Leu Ile
        35                  40                  45

Tyr Lys Ala Ser Asn Arg Asn Thr Gly Val Pro Ser Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys Met Gln Ser Thr Ser Tyr Pro Leu
                85                  90                  95

Thr Phe Gly Gln Gly Thr Lys Leu Glu Ile Lys
            100                 105

<210> SEQ ID NO 88
<211> LENGTH: 122
<212> TYPE: PRT
<213> ORGANISM: Artificial Sequence
<220> FEATURE:
<223> OTHER INFORMATION: Synthetic: Caninized variable heavy chain of
      Mab B v3

<400> SEQUENCE: 88

Glu Val Gln Leu Val Glu Ser Gly Gly Asp Leu Val Lys Pro Gly Gly
1               5                   10                  15

Thr Leu Arg Leu Ser Cys Thr Val Ser Gly Phe Ser Leu Thr Ser Tyr
            20                  25                  30

Gly Val Ser Trp Val Arg Gln Ser Pro Gly Lys Gly Leu Glu Trp Ile
        35                  40                  45

Gly Thr Met Trp Asn Asp Gly Asp Thr Asp Tyr His Ser Ala Val Lys
```

-continued

```
                50                  55                  60
Gly Gln Leu Ser Ile Ser Arg Asp Thr Ser Lys Ser Gln Val Phe Leu
 65                  70                  75                  80

Gln Met Asn Ser Leu Arg Ala Glu Asp Thr Ala Met Tyr Tyr Cys Ala
                 85                  90                  95

Arg Ser Gln Leu Pro Gly Tyr Asn Leu Arg Gly Trp Phe Val Tyr Trp
                100                 105                 110

Gly Gln Gly Thr Leu Val Thr Val Ser Ser
                115                 120

<210> SEQ ID NO 89
<211> LENGTH: 106
<212> TYPE: PRT
<213> ORGANISM: Artificial Sequence
<220> FEATURE:
<223> OTHER INFORMATION: Synthetic: Caninized variable light chain of
      Mab B v3

<400> SEQUENCE: 89

Glu Ile Val Leu Thr Gln Ser Pro Ala Ser Leu Ala Val Ser Leu Gly
 1               5                  10                  15

Gln Arg Ala Thr Ile Ser Cys Lys Ala Ser His Asn Ile Asn Lys Asn
                 20                  25                  30

Leu Glu Trp Tyr Gln Gln Lys Pro Gly Gln Pro Pro Lys Leu Leu Ile
             35                  40                  45

Tyr Tyr Ala Asn Asn Leu Gln Thr Gly Val Pro Ala Arg Phe Ser Gly
 50                  55                  60

Ser Gly Ser Gly Thr Asp Tyr Ser Leu Asn Ile His Pro Met Glu Glu
 65                  70                  75                  80

Asp Asp Thr Ala Met Tyr Tyr Cys Tyr Gln Tyr Asn Ser Gly His Thr
                 85                  90                  95

Phe Gly Gly Gly Thr Lys Leu Glu Ile Lys
                100                 105

<210> SEQ ID NO 90
<211> LENGTH: 216
<212> TYPE: PRT
<213> ORGANISM: Artificial Sequence
<220> FEATURE:
<223> OTHER INFORMATION: Synthetic: Exemplary canine CD16 with linker,
      and poly-His

<400> SEQUENCE: 90

Met Trp Gln Leu Val Ser Ser Thr Ala Leu Leu Leu Val Ser Ala
 1               5                  10                  15

Gly Thr Gln Ala Ala Asp Val Pro Lys Ala Val Val Leu Glu Pro
                 20                  25                  30

Lys Trp Asn Arg Val Leu Thr Met Asp Ser Val Thr Leu Lys Cys Gln
             35                  40                  45

Gly Asp His Leu Leu Arg Asp Asn Tyr Thr Trp Leu His Asn Gly Arg
 50                  55                  60

Pro Ile Ser Asn Gln Ile Ser Thr Tyr Ile Ile Lys Asn Ala Ser Ile
 65                  70                  75                  80

Lys Asn Ser Gly Glu Tyr Arg Cys Gln Thr Asp Gln Ser Lys Leu Ser
                 85                  90                  95

Asp Pro Val Gln Leu Glu Val His Thr Gly Trp Leu Leu Leu Gln Val
                100                 105                 110

Pro Arg Leu Val Phe Gln Glu Gly Glu Leu Ile Gln Leu Lys Cys His
```

```
            115                 120                 125
Ser Trp Lys Asn Thr Pro Val Arg Asn Val Gln Tyr Phe Gln Asn Gly
    130                 135                 140

Arg Gly Lys Lys Phe Phe Tyr Asn Asn Ser Glu Tyr His Ile Pro Ala
145                 150                 155                 160

Ala Thr Ser Glu His Asn Gly Ser Tyr Phe Cys Arg Gly Ile Ile Gly
                165                 170                 175

Lys Lys Asn Glu Ser Ser Glu Ala Val Asn Ile Ile Ile Gln Gly Ser
            180                 185                 190

Ser Leu Pro Ser Thr Ser Leu Leu Leu Ser His Trp Pro Gln Gly Ser
                195                 200                 205

Gly Ser His His His His His His
            210                 215

<210> SEQ ID NO 91
<211> LENGTH: 220
<212> TYPE: PRT
<213> ORGANISM: Artificial Sequence
<220> FEATURE:
<223> OTHER INFORMATION: Synthetic: Exemplary wild-type canine IgG-B Fc

<400> SEQUENCE: 91

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 92
<211> LENGTH: 220
<212> TYPE: PRT
<213> ORGANISM: Artificial Sequence
<220> FEATURE:
<223> OTHER INFORMATION: Synthetic: Exemplary variant canine IgG-B Fc,
```

CD16 enhancing binding mutant, S10D

<400> SEQUENCE: 92

```
Pro Ala Pro Glu Met Leu Gly Gly Pro Asp Val Phe Ile Ph

```
            115                 120                 125
Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
                195                 200                 205

Tyr Thr Gln Glu Ser Leu Ser His Ser Pro Gly Lys
            210                 215                 220
```

<210> SEQ ID NO 94
<211> LENGTH: 220
<212> TYPE: PRT
<213> ORGANISM: Artificial Sequence
<220> FEATURE:
<223> OTHER INFORMATION: Synthetic: Exemplary variant canine IgG-B Fc, CD16 enhancing binding mutant, I103D

<400> SEQUENCE: 94

```
Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
            35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Asp Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
                195                 200                 205

Tyr Thr Gln Glu Ser Leu Ser His Ser Pro Gly Lys
            210                 215                 220
```

<210> SEQ ID NO 95
<211> LENGTH: 220
<212> TYPE: PRT
<213> ORGANISM: Artificial Sequence
<220> FEATURE:

<223> OTHER INFORMATION: Synthetic: Exemplary variant canine IgG-B Fc,
      CD16 enhancing binding mutant, I103E

<400> SEQUENCE: 95

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Glu Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 96
<211> LENGTH: 220
<212> TYPE: PRT
<213> ORGANISM: Artificial Sequence
<220> FEATURE:
<223> OTHER INFORMATION: Synthetic: Exemplary variant canine IgG-B Fc,
      CD16 enhancing binding mutant, S10D, I103D

<400> SEQUENCE: 96

Pro Ala Pro Glu Met Leu Gly Gly Pro Asp Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Asp Arg Thr Ile Ser Lys Ala Arg Gly
            100                 105                 110

```
Gln Ala His Gln Pro Ser Val Tyr Val Leu Pro Pro Ser Arg Glu Glu
            115                 120                 125

Leu Ser Lys Asn Thr Val Ser Leu Thr Cys Leu Ile Lys Asp Phe Phe
        130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
            195                 200                 205

Tyr Thr Gln Glu Ser Leu Ser His Ser Pro Gly Lys
    210                 215                 220

<210> SEQ ID NO 97
<211> LENGTH: 220
<212> TYPE: PRT
<213> ORGANISM: Artificial Sequence
<220> FEATURE:
<223> OTHER INFORMATION: Synthetic: Exemplary variant canine IgG-B Fc,
      CD16 enhancing binding mutant, S10D, I103E

<400> SEQUENCE: 97

Pro Ala Pro Glu Met Leu Gly Gly Pro Asp Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Glu Arg Thr Ile Ser Lys Ala Arg Gly
            100                 105                 110

Gln Ala His Gln Pro Ser Val Tyr Val Leu Pro Pro Ser Arg Glu Glu
            115                 120                 125

Leu Ser Lys Asn Thr Val Ser Leu Thr Cys Leu Ile Lys Asp Phe Phe
        130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
            195                 200                 205

Tyr Thr Gln Glu Ser Leu Ser His Ser Pro Gly Lys
    210                 215                 220

<210> SEQ ID NO 98
<211> LENGTH: 220
<212> TYPE: PRT
<213> ORGANISM: Artificial Sequence
```

<220> FEATURE:
<223> OTHER INFORMATION: Synthetic: Exemplary variant canine IgG-B Fc,
      CD16 enhancing binding mutant, S10E, I103D

<400> SEQUENCE: 98

Pro Ala Pro Glu Met Leu Gly Gly Pro Glu Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Asp Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 99
<211> LENGTH: 220
<212> TYPE: PRT
<213> ORGANISM: Artificial Sequence
<220> FEATURE:
<223> OTHER INFORMATION: Synthetic: Exemplary variant canine IgG-B Fc,
      CD16 enhancing binding mutant, S10E, I103E

<400> SEQUENCE: 99

Pro Ala Pro Glu Met Leu Gly Gly Pro Glu Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Glu Glu Arg Thr Ile Ser Lys Ala Arg Gly
            100                 105                 110

```
Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
        130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
        210                 215                 220
```

PARVOVIRUS ANTIBODIES FOR VETERINARY USE

CROSS-REFERENCE TO RELATED APPLICATIONS

This application is a national stage entry of International Patent Application No. PCT/US2020/044302, filed Jul. 30, 2020, which claims the benefit of priority of U.S. Provisional Application No. 62/880,650, filed Jul. 30, 2019, U.S. Provisional Application No. 62/968,970 filed Jan. 31, 2020, and U.S. Provisional Application No. 63/030,123 filed May 26, 2020, each of which is incorporated by reference herein in its entirety for any purpose.

FIELD OF THE INVENTION

This invention relates to isolated canine parvovirus antibodies, for example, with improved recombinant production and neutralizing binding to canine parvovirus and/or feline parvovirus, and methods of using the same, for example, for providing passive immunity against infection with a canine or feline parvovirus and/or treating parvoviral infection in companion animals, such as dogs and cats.

BACKGROUND

Canine Parvovirus (CPV) is the most important enteric virus infecting dogs worldwide[1]. The CPV virion is a non-enveloped, DNA virus. There are multiple variants of the original CPV, including CPV-2a, CPV-2b, and CPV-2c. The variants of CPV-2 differ from one another by only a few amino acids[2]. Quite persistent in the environment, CPV may remain infective for months. CPV spreads via direct and indirect contact[3]. Upon contact with the oral mucosa, CPV begins to replicate in local lymphatics and spreads systemically. With a 4 to 14 day incubation period, CPV targets rapidly dividing cells of the body including bone marrow, lymphocytes and intestinal crypt epithelial cells.

Clinical disease manifests as fever and depression followed by vomiting, diarrhea (profuse and bloody), lymphopenia, dehydration and quite often secondary septicemia and death. Mortality may exceed 70% in puppies[3]. Infection is most common in puppies after weaning as the maternal antibodies begin to wane. Vaccines are readily available and effectively protect against all variants of CPV-2.

Although properly timed vaccinations are protective, parvovirus infection remains a problem. The primary population of susceptible canines includes puppies in the vulnerable window where maternally derived antibody has waned to non-protective levels and before vaccination has been given (see FIG. 1). Puppies under 24 weeks of age are at highest risk of CPV disease. Additionally, puppies with failure of passive transfer of maternally derived antibodies is another vulnerable population. Outbreaks continue to occur in naïve kennel and shelter populations as well.

Treatment for CPV infection up to this point has been largely supportive. Treatment typically involves intravenous fluids, antiemetics, and broad-spectrum antibiotics to protect against septicemia. Various other treatments have been tried unsuccessfully including anti-virals and hyperimmune plasma[4]. Hospitalization is typically recommended which can be cost-prohibitive for many owners and can lead to the decision to euthanize. Hospitalizing dogs with CPV infection requires strict isolation protocols. This can prove to be a logistics hardship for veterinary facilities and staff[5]. Thus, there is an unmet medical need for prevention and therapeutic treatment.

There are currently no USDA or FDA approved therapies specifically for CPV. A parvovirus monoclonal antibody described herein would be given as a therapeutic intervention to dogs with an active CPV infection to decrease the severity of or eliminate morbidity and mortality associated with CPV. Additionally, a parvovirus monoclonal antibody described herein would be utilized as a prophylactic treatment for dogs exposed to CPV infected dogs to prevent development of CPV infection.

SUMMARY OF THE INVENTION

Embodiment 1. An isolated antibody that binds to canine parvovirus and/or feline parvovirus, wherein the antibody comprises: (a) (i) a CDR-H1 comprising the amino acid sequence of SEQ ID NO: 4, (ii) a CDR-H2 comprising the amino acid sequence of SEQ ID NO: 5, (iii) a CDR-H3 comprising the amino acid sequence of SEQ ID NO: 6, and (iv) an HC-FR1 sequence of SEQ ID NO: 7 or SEQ ID NO: 8; or (b) (i) a CDR-H1 comprising the amino acid sequence of SEQ ID NO: 42, (ii) a CDR-H2 comprising the amino acid sequence of SEQ ID NO: 43, (iii) a CDR-H3 comprising the amino acid sequence of SEQ ID NO: 44, and (iv) an HC-FR1 sequence of SEQ ID NO: 45 or SEQ ID NO: 46.

Embodiment 2. An isolated antibody that binds to canine parvovirus and/or feline parvovirus, wherein the antibody comprises: (a) (i) a CDR-L1 comprising the amino acid sequence of SEQ ID NO: 13, (ii) a CDR-L2 comprising the amino acid sequence of SEQ ID NO: 14, (iii) a CDR-L3 comprising the amino acid sequence of SEQ ID NO: 15, and (iv) an LC-FR1 sequence of SEQ ID NO: 16; or (b) (i) a CDR-L1 comprising the amino acid sequence of SEQ ID NO: 52, (ii) a CDR-L2 comprising the amino acid sequence of SEQ ID NO: 53, (iii) a CDR-L3 comprising the amino acid sequence of SEQ ID NO: 54, and (iv) an LC-FR1 sequence of SEQ ID NO: 55 or SEQ ID NO: 56.

Embodiment 3. The isolated antibody of embodiment 1, wherein the antibody of (a) comprises an HC-FR4 sequence of SEQ ID NO: 12.

Embodiment 4. The isolated antibody of embodiment 1, wherein the antibody of (b) comprises an HC-FR2 sequence of SEQ ID NO: 48.

Embodiment 5. The isolated antibody of embodiment 1 or embodiment 4, wherein the antibody of (b) comprises an HC-FR3 sequence of SEQ ID NO: 50.

Embodiment 6. The isolated antibody of embodiment 2, wherein the antibody of (b) comprises an HC-FR3 sequence of SEQ ID NO: 59.

Embodiment 7. The isolated antibody of embodiment 2 or embodiment 6, wherein the antibody of (b) comprises an HC-F4 sequence of SEQ ID NO: 61.

Embodiment 8. An isolated antibody that binds to canine parvovirus and/or feline parvovirus, wherein the antibody is a caninized or a felinized antibody comprising: a) a heavy chain comprising (i) a CDR-H1 comprising the amino acid sequence of SEQ ID NO: 4; (ii) a CDR-H2 comprising the amino acid sequence of SEQ ID NO: 5; and (iii) a CDR-H3 comprising the amino acid sequence of SEQ ID NO: 6, or b) a heavy chain comprising (i) a CDR-H1 comprising the amino acid sequence of SEQ ID NO: 42; (ii) a CDR-H2 comprising the amino acid sequence of SEQ ID NO: 43; and (iii) a CDR-H3 comprising the amino acid sequence of SEQ ID NO: 44.

Embodiment 9. An isolated antibody that binds to canine parvovirus and/or feline parvovirus, wherein the antibody is a caninized or a felinized antibody comprising: a) a light chain comprising (i) a CDR-L1 comprising the amino acid sequence of SEQ ID NO: 13; (ii) a CDR-L2 comprising the amino acid sequence of SEQ ID NO: 14; and (iii) a CDR-L3 comprising the amino acid sequence of SEQ ID NO: 15, or b) a light chain comprising (i) a CDR-L1 comprising the amino acid sequence of SEQ ID NO: 52; (ii) a CDR-L2 comprising the amino acid sequence of SEQ ID NO: 53; and (iii) a CDR-L3 comprising the amino acid sequence of SEQ ID NO: 54.

Embodiment 10. An isolated antibody that binds to canine parvovirus and/or feline parvovirus, wherein the antibody is a caninized or a felinized antibody comprising: a) a heavy chain comprising (i) a CDR-H1 comprising the amino acid sequence of SEQ ID NO: 4; (ii) a CDR-H2 comprising the amino acid sequence of SEQ ID NO: 5; and (iii) a CDR-H3 comprising the amino acid sequence of SEQ ID NO: 6, and b) a light chain comprising (i) a CDR-L1 comprising the amino acid sequence of SEQ ID NO: 13; (ii) a CDR-L2 comprising the amino acid sequence of SEQ ID NO: 14; and (iii) a CDR-L3 comprising the amino acid sequence of SEQ ID NO: 15.

Embodiment 11. An isolated antibody that binds to canine parvovirus and/or feline parvovirus, wherein the antibody is a caninized or a felinized antibody comprising: a) a heavy chain comprising (i) a CDR-H1 comprising the amino acid sequence of SEQ ID NO: 42; (ii) a CDR-H2 comprising the amino acid sequence of SEQ ID NO: 43; and (iii) a CDR-H3 comprising the amino acid sequence of SEQ ID NO: 44, and b) a light chain comprising (i) a CDR-L1 comprising the amino acid sequence of SEQ ID NO: 52; (ii) a CDR-L2 comprising the amino acid sequence of SEQ ID NO: 53; and (iii) a CDR-L3 comprising the amino acid sequence of SEQ ID NO: 54.

Embodiment 12. The antibody of any one of the preceding embodiments, wherein the antibody is a chimeric antibody.

Embodiment 13. The antibody of any one of the preceding embodiments, wherein the antibody comprises a canine or feline constant heavy chain region or a canine or feline constant light chain region.

Embodiment 14. The antibody of any one of the preceding embodiments, wherein the antibody comprises:
(a) a canine heavy chain constant region selected from an IgG-A, IgG-B, IgG-C, and IgG-D constant region; or
(b) a feline heavy chain constant region selected from an IgG1, IgG2a, and IgG2b constant region.

Embodiment 15. The antibody of any one of the preceding embodiments, wherein the antibody comprises a wild-type or variant IgG Fc having complement fixation activity.

Embodiment 16. The antibody of any one of the preceding embodiments, wherein the antibody comprises a wild-type or variant IgG Fc having antibody-dependent cellular cytotoxicity (ADCC) activity.

Embodiment 17. The antibody of any one of the preceding embodiments, wherein the antibody comprises a wild-type or variant IgG Fc having antibody-dependent cellular phagocytosis (ADCP) activity.

Embodiment 18. The antibody of any one of the preceding embodiments, wherein the antibody comprises: a) an aspartic acid or a glutamic acid at a position corresponding to position 10 of SEQ ID NO: 91; b) an aspartic acid or a glutamic acid at position 10 of SEQ ID NO: 91; c) an aspartic acid or a glutamic acid at a position corresponding to position 103 of SEQ ID NO: 91; d) an aspartic acid or a glutamic acid at position 103 of SEQ ID NO: 91; e) an aspartic acid or a glutamic acid at a position corresponding to position 10 and/or position 103 of SEQ ID NO: 91; f) an aspartic acid or a glutamic acid at position 10 and/or position 103 of SEQ ID NO: 91; or g) the amino acid sequence of SEQ ID NO: 92, SEQ ID NO: 93, SEQ ID NO: 94, SEQ ID NO: 95, SEQ ID NO: 96, SEQ ID NO: 97, SEQ ID NO: 98, or SEQ ID NO: 99.

Embodiment 19. The antibody of any one of the preceding embodiments, wherein the antibody comprises a canine κ light constant region or a feline κ light constant region.

Embodiment 20. The antibody of any one of the preceding embodiments, wherein the antibody comprises a feline κ light constant region without one or more N-glycosylation sites.

Embodiment 21. The antibody of any one of the preceding embodiments, wherein the antibody binds to an epitope comprising the amino acid sequence of SEQ ID NO: 1, SEQ ID NO: 2, and/or SEQ ID NO: 3.

Embodiment 22. The antibody of any one of the preceding embodiments, wherein the antibody binds to canine parvovirus or feline parvovirus with a dissociation constant (Kd) of less than $5\times10^{-6}$ M, less than $1\times10^{-6}$ M, less than $5\times10^{-7}$ M, less than $1\times10^{-7}$ M, less than $5\times10^{-8}$ M, less than $1\times10^{-8}$ M, less than $5\times10^{-9}$ M, less than $1\times10^{-9}$ M, less than $5\times10^{-10}$ M, less than $1\times10^{-10}$ M, less than $5\times10^{-11}$ M, less than $1\times10^{-11}$ M, less than $5\times10^{-12}$ M, less than $1\times10^{-12}$ M, less than $5\times10^{-13}$ M, or less than $1\times10^{-13}$ M as measured by biolayer interferometry.

Embodiment 23. The antibody of any one of the preceding embodiments, wherein the antibody binds to canine parvovirus or feline parvovirus as determined by immunoblot analysis and/or biolayer interferometry.

Embodiment 24. The antibody of any one of the preceding embodiments, wherein the antibody at a concentration of 200 m/mL has an hemagglutination inhibition value of at least 8000, of at least 16000, of at least 32000.

Embodiment 25. The antibody of any one of the preceding embodiments, wherein the antibody is a monoclonal antibody.

Embodiment 26. The antibody of any one of the preceding embodiments comprising one or more of (a) an (HC-FR1) sequence of SEQ ID NO: 7, 8, 45, or 46; (b) a HC-FR2 sequence of SEQ ID NO: 9, 47, or 48; (c) a HC-FR3 sequence of SEQ ID NO: 10, 49, or 50; (d) a HC-FR4 sequence of SEQ ID NO: 11, 12, or 51; (e) a variable region light chain framework 1 (LC-FR1) sequence of SEQ ID NO: 16, 55, or 56; (f) an LC-FR2 sequence of SEQ ID NO: 17 or 57; (g) an LC-FR3 sequence of SEQ ID NO: 18, 58, or 59; or (h) an LC-FR4 sequence of SEQ ID NO: 19, 60, or 61.

Embodiment 27. The antibody of any one of the preceding embodiments, wherein the antibody comprises: (a) a variable heavy chain sequence of SEQ ID NO: 20, SEQ ID NO: 21, SEQ ID NO: 85, SEQ ID NO: 86, SEQ ID NO: 40, SEQ ID NO: 62, SEQ ID NO: 63, or SEQ ID NO: 88; and/or (b) a variable light chain sequence of SEQ ID NO: 22, SEQ ID NO: 87, SEQ ID NO: 41, SEQ ID NO: 64, SEQ ID NO: 65, or SEQ ID NO: 89.

Embodiment 28. The antibody of any one of the preceding embodiments, wherein the antibody comprises: (a) a variable heavy chain sequence of SEQ ID NO: 20 and a variable light chain sequence of SEQ ID NO: 22; (b) a variable heavy chain sequence of SEQ ID NO: 21 and a variable light chain sequence of SEQ ID NO: 22; (c) a variable heavy chain sequence of SEQ ID NO: 85 and a variable light chain sequence of SEQ ID NO: 87; (d) a variable heavy chain sequence of SEQ ID NO: 86 and a variable light chain sequence of SEQ ID NO: 87; (e) a variable heavy chain sequence of SEQ ID NO: 40 and a variable light chain sequence of SEQ ID NO: 41; (f) a variable heavy chain sequence of SEQ ID NO: 62 and a variable light chain sequence of SEQ ID NO: 64 or SEQ ID NO: 65; (g) a variable heavy chain sequence of SEQ ID NO: 63 and a variable light chain sequence of SEQ ID NO: 64 or SEQ ID NO: 65; or (h) a variable heavy chain sequence of SEQ ID NO: 88 and a variable light chain sequence of SEQ ID NO: 89.

Embodiment 29. The antibody of any one of the preceding embodiments, wherein the antibody comprises: (a) (i) a heavy chain sequence of SEQ ID NO: 23, SEQ ID NO: 24, SEQ ID NO: 37, SEQ ID NO: 38, SEQ ID NO: 66, SEQ ID NO: 67, or SEQ ID NO: 79; and/or (ii) a light chain sequence of SEQ ID NO: 25, SEQ ID NO: 39, SEQ ID NO: 68, SEQ ID NO: 69, or SEQ ID NO: 80; or (b) (i) a heavy chain sequence of SEQ ID NO: 31, SEQ ID NO: 40, or SEQ ID NO: 74; and/or (ii) a light chain sequence of SEQ ID NO: 32, SEQ ID NO: 33, SEQ ID NO: 41, SEQ ID NO: 75, or SEQ ID NO: 76.

Embodiment 30. The antibody of any one of the preceding embodiments, wherein the antibody comprises: (a) a heavy chain sequence of SEQ ID NO: 23 or SEQ ID NO: 24, and a light chain sequence of SEQ ID NO: 25; (b) a heavy chain sequence of SEQ ID NO: 31 and a light chain sequence of SEQ ID NO: 32 or SEQ ID NO: 33; (c) a heavy chain sequence of SEQ ID NO: 37 or SEQ ID NO: 38, and a light chain sequence of SEQ ID NO: 39; (d) a heavy chain sequence of SEQ ID NO: 66 or SEQ ID NO: 67, and a light chain sequence of SEQ ID NO: 68 or SEQ ID NO: 69; (e) a heavy chain sequence of SEQ ID NO: 66 and a light chain sequence of SEQ ID NO: 68; (f) a heavy chain sequence of SEQ ID NO: 67 and a light chain sequence of SEQ ID NO: 69; (g) a heavy chain sequence of SEQ ID NO: 74 and a light chain sequence of SEQ ID NO: 75 or SEQ ID NO: 76; or (h) a heavy chain sequence of SEQ ID NO: 79 and a light chain sequence of SEQ ID NO: 80.

Embodiment 31. The antibody of any one of the preceding embodiments, wherein the antibody comprises a heavy chain sequence of SEQ ID NO: 24 and a light chain sequence of SEQ ID NO: 25.

Embodiment 32. An isolated nucleic acid encoding the antibody of any one of the preceding embodiments.

Embodiment 33. A host cell comprising the nucleic acid of embodiment 31.

Embodiment 34. A method of producing an antibody comprising culturing the host cell of embodiment 32 and isolating the antibody.

Embodiment 35. A pharmaceutical composition comprising the antibody of any one or more of embodiments 1 to 31 and a pharmaceutically acceptable carrier.

Embodiment 36. The pharmaceutical composition of embodiment 35, wherein the pharmaceutically acceptable carrier is phosphate buffered saline.

Embodiment 37. A method of providing passive immunity in a subject against infection with a canine or feline parvovirus comprising administering to the subject a therapeutically effective amount of a monoclonal antibody that binds to the canine or feline parvovirus.

Embodiment 38. The method of embodiments 37, wherein the monoclonal antibody is administered before exposure to the canine or feline parvovirus.

Embodiment 39. The method of embodiment 37 or embodiment 38, wherein the monoclonal antibody is administered after exposure to the canine or feline parvovirus.

Embodiment 40. The method of any one of embodiments 37 to 39, wherein the monoclonal antibody is administered after infection with the canine or feline parvovirus.

Embodiment 41. The method of any one of embodiments 37 to 40, wherein the monoclonal antibody is administered after the subject has exhibited at least one symptoms selected from fever, vomiting, diarrhea, lymphopenia, and septicemia.

Embodiment 42. The method of any one of embodiments 37 to 41, wherein the monoclonal antibody is administered after canine or feline parvovirus has been detected in feces, such as determined by a positive cage-side SNAP test.

Embodiment 43. The method of any one of embodiments 37 to 42, wherein the subject has previously been administered a parvovirus vaccine.

Embodiment 44. The method of any one of embodiments 37 to 42, wherein the subject has not previously been administered a parvovirus vaccine.

Embodiment 45. The method of any one of embodiments 37 to 44, wherein the subject is unprotected at birth due to lack of maternally-derived antibodies to a canine or feline parvovirus or failure of passive transfer of antibodies to a canine or feline parvovirus.

Embodiment 46. The method of any one of embodiments 37 to 45, wherein the subject is hand-reared, the subject's mother does not produce milk, or the subject is unable to produce antibodies against parvovirus.

Embodiment 47. The method of any one of embodiments 37 to 46, wherein the subject is living in an environment contaminated with the canine or feline parvovirus.

Embodiment 48. A method of treating a canine or feline parvoviral infection in a subject comprising administering to the subject a therapeutically effective amount of a monoclonal antibody that binds to the canine or feline parvovirus.

Embodiment 49. The method of embodiment 48, wherein the monoclonal antibody is administered after the subject has exhibited at least one symptoms selected from fever, vomiting, diarrhea, lymphopenia, and septicemia.

Embodiment 50. The method of embodiment 48 or embodiment 49, wherein the monoclonal antibody is administered after canine or feline parvovirus has been detected in feces, such as determined by a positive cage-side SNAP test.

Embodiment 51. The method of any one of embodiments 48 to 50, wherein the subject has previously been administered a parvovirus vaccine.

Embodiment 52. The method of any one of embodiments 48 to 50, wherein the subject has not previously been administered a parvovirus vaccine.

Embodiment 53. The method of any one of embodiments 48 to 52, wherein the subject is living in an environment contaminated with the canine or feline parvovirus.

Embodiment 54. The method of any one of embodiments 48 to 53, wherein the subject is a canine or feline.

Embodiment 55. The method of any one of embodiments 48 to 53, wherein the subject is a human.

Embodiment 56. The method of any one of embodiments 37 to 55, wherein the method comprises administering to the subject a therapeutically effective amount of an monoclonal antibody that binds to an epitope comprising the amino acid sequence of SEQ ID NO: 1, SEQ ID NO: 2, and/or SEQ ID NO: 3.

Embodiment 57. The method of any one of embodiments 37 to 56, wherein the method comprises administering to the subject a therapeutically effective amount of a monoclonal antibody comprising: (a) a heavy chain comprising (i) a CDR-H1 comprising the amino acid sequence of SEQ ID NO: 42; (ii) a CDR-H2 comprising the amino acid sequence of SEQ ID NO: 43; and (iii) a CDR-H3 comprising the amino acid sequence of SEQ ID NO: 44, and (b) a light chain comprising (i) a CDR-L1 comprising the amino acid sequence of SEQ ID NO: 52; (ii) a CDR-L2 comprising the amino acid sequence of SEQ ID NO: 53; and (iii) a CDR-L3 comprising the amino acid sequence of SEQ ID NO: 54.

Embodiment 58. The method of any one of embodiments 37 to 57, wherein the method comprises administering to the subject a therapeutically effective amount of the antibody of any one of embodiments 1 to 31 or the pharmaceutical composition of embodiment 35 or embodiment 36.

Embodiment 59. The method of any one of embodiments 37 to 58, wherein the antibody or the pharmaceutical composition is administered parenterally.

Embodiment 60. The method of any one of embodiments 37 to 59, wherein the antibody or the pharmaceutical composition is administered by an intramuscular route, an intraperitoneal route, an intracerebrospinal route, a subcutaneous route, an intra-arterial route, an intrasynovial route, an intrathecal route, an intravenous, or an inhalation route.

Embodiment 61. The method of any one of embodiments 37 to 60, wherein the antibody or the pharmaceutical composition is administered intravenously.

Embodiment 62. The method of any one of embodiments 37 to 60, wherein the antibody or the pharmaceutical composition is administered subcutaneously.

Embodiment 63. The method of any one of embodiments 37 to 62, wherein the subject is less than 1 week of age, less than 2 weeks of age, less than 3 weeks of age, less than 4 weeks of age, less than 5 weeks of age, less than 6 weeks of age, less than 6 weeks of age, less than 7 weeks of age, less than 8 weeks of age, less than 9 weeks of age, less than 10 weeks of age, less than 11 weeks of age, less than 12 weeks of age, less than 6 months of age, between 0 and 12 weeks of age, between 0 and 10 weeks of age, between 0 and 8 weeks of age, between 0 and 6 weeks of age, between 0 and 4 weeks of age, between 0 and 2 weeks of age, between 4 and 12 weeks of age, between 6 and 12 weeks of age, between 10 and 12 weeks of age, between 4 weeks and 6 months of age, between 2 months and 6 months of age, between 4 months and 6 months of age, between 6 months and 1 year of age, greater than 13 weeks of age, or greater than 1 year of age.

Embodiment 64. The method of any one of embodiments 37 to 63, wherein the subject is 13 weeks of age or older.

Embodiment 65. The method of any one of embodiments 37 to 64, wherein the antibody is administered at an amount in the range of 0.01 mg/kg body weight to 100 mg/kg body weight per dose.

Embodiment 66. The method of any one of embodiments 37 to 65, wherein the antibody is administered at an amount of 5 mg/kg body weight per dose.

Embodiment 67. The method of any one of embodiments 37 to 66, wherein the antibody or the pharmaceutical composition is administered as a single dose.

Embodiment 68. The method of any one of embodiments 37 to 67, wherein the antibody or the pharmaceutical composition is administered repeatedly, such as once per week for at least two or three consecutive weeks.

Embodiment 69. The method of any one of embodiments 37 to 68, the method comprises administering to the subject a therapeutically effective amount of two or more different antibodies of any one of embodiments 1 to 31, wherein the two or more different antibodies are administered simultaneously or sequentially, optionally wherein administration of the two or more different antibodies is separated by one or more days.

Embodiment 70. The method of any one of embodiments 37 to 69, wherein the subject has a hemagglutination inhibition titer of less than 20 as determined by hemagglutination inhibition assay prior to administration of the antibody or the pharmaceutical composition.

Embodiment 71. The method of any one of embodiments 37 to 70, wherein the subject is parvovirus titer negative as determined by hemagglutination inhibition assay prior to administration of the antibody or the pharmaceutical composition.

Embodiment 72. The method of any one of embodiments 37 to 71, wherein the subject survives infection with a canine or feline parvovirus following administration of the antibody or the pharmaceutical composition.

Embodiment 73. The method of reducing parvoviral infection of a cell, the method comprising exposing to the cell the antibody of any one of embodiments 1 to 31 or the pharmaceutical composition of embodiment 35 or embodiment 36 under conditions permissive for binding of the antibody to a parvovirus.

Embodiment 74. The method of embodiment 73, wherein the cell is exposed to the antibody or the pharmaceutical composition in vitro.

Embodiment 75. The method of embodiment 73 or embodiment 74, wherein the cell is a mammalian cell, a human cell, a canine cell, or a feline cell.

Embodiment 76. A method for detecting a parvoviral infection in a sample from a subject comprising contacting the sample with the antibody of any one of embodiments 1 to 31 or the pharmaceutical composition of embodiment 35 or embodiment 36 under conditions permissive for the binding of the antibody to a parvovirus, and detecting whether a complex is formed between the antibody and the parvovirus in the sample.

Embodiment 77. The method of embodiment 76, wherein the sample is a biological sample obtained from a canine, a feline, or a human.

Embodiment 78. A variant IgG Fc polypeptide comprising: a) an aspartic acid or a glutamic acid at a position corresponding to position 10 of SEQ ID NO: 91; b) an aspartic acid or a glutamic acid at position 10 of SEQ ID NO: 91; c) an aspartic acid or a glutamic acid at a position corresponding to position 103 of SEQ ID NO: 91; d) an aspartic acid or a glutamic acid at position 103 of SEQ ID NO: 91; e) an aspartic acid or a glutamic acid at a position corresponding to position 10 and/or position 103 of SEQ ID NO: 91; or f) an aspartic acid or a glutamic acid at position 10 and/or position 103 of SEQ ID NO: 91.

Embodiment 79. A polypeptide comprising the variant IgG Fc polypeptide of embodiment 78.

Embodiment 80. A polypeptide comprising the amino acid sequence of SEQ ID NO: 92, SEQ ID NO: 93, SEQ ID NO: 94, SEQ ID NO: 95, SEQ ID NO: 96, SEQ ID NO: 97, SEQ ID NO: 98, or SEQ ID NO: 99.

Embodiment 81. An isolated nucleic acid encoding the polypeptide of any one of embodiments 78 to 80.

Embodiment 82. A host cell comprising the nucleic acid of embodiment 81.

BRIEF DESCRIPTION OF THE DRAWINGS

FIG. 3C shows the HI assay titers for both Mab A and Mab B groups.

DESCRIPTION OF CERTAIN SEQUENCES

Figure 1:
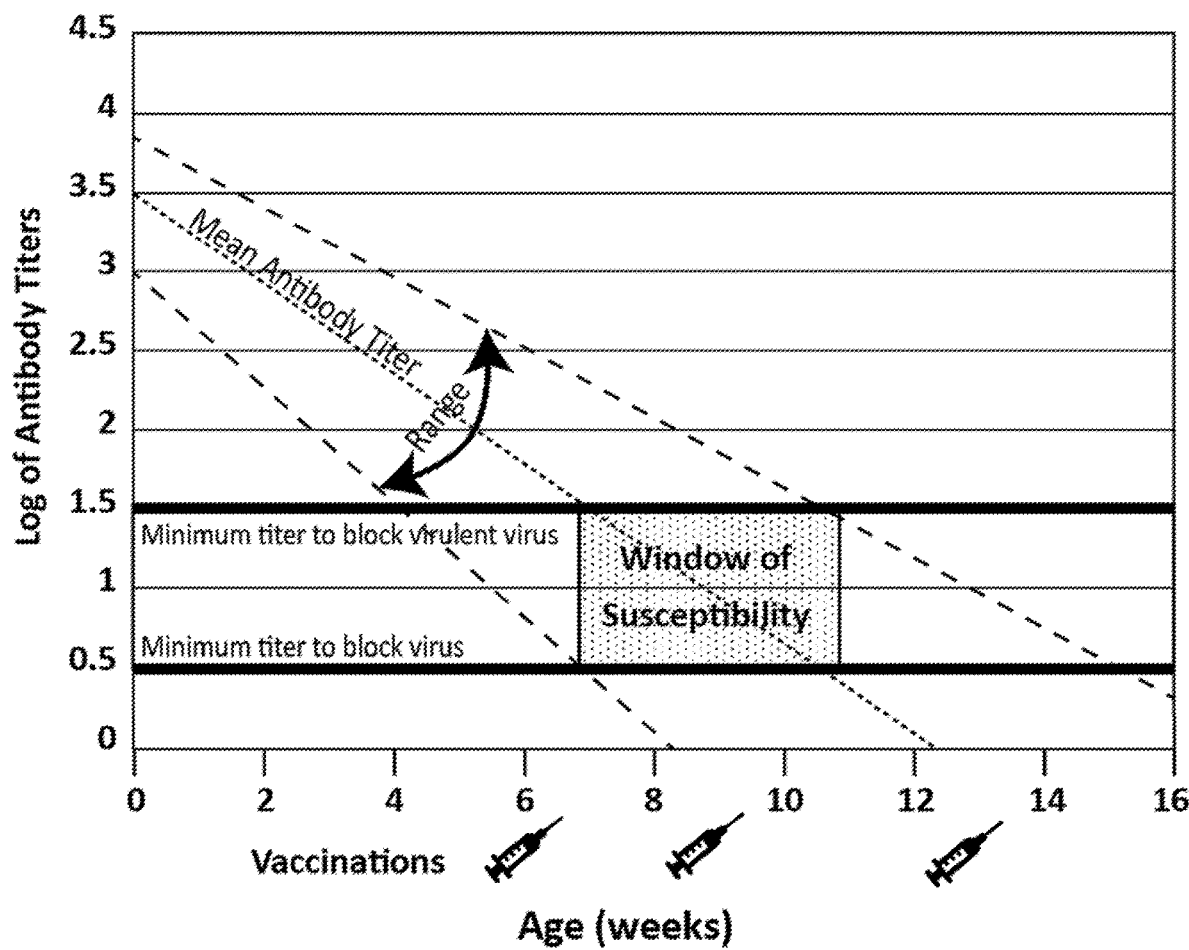
FIG. 1 is a diagram of the window of susceptibility for CPV.
Figure 2:
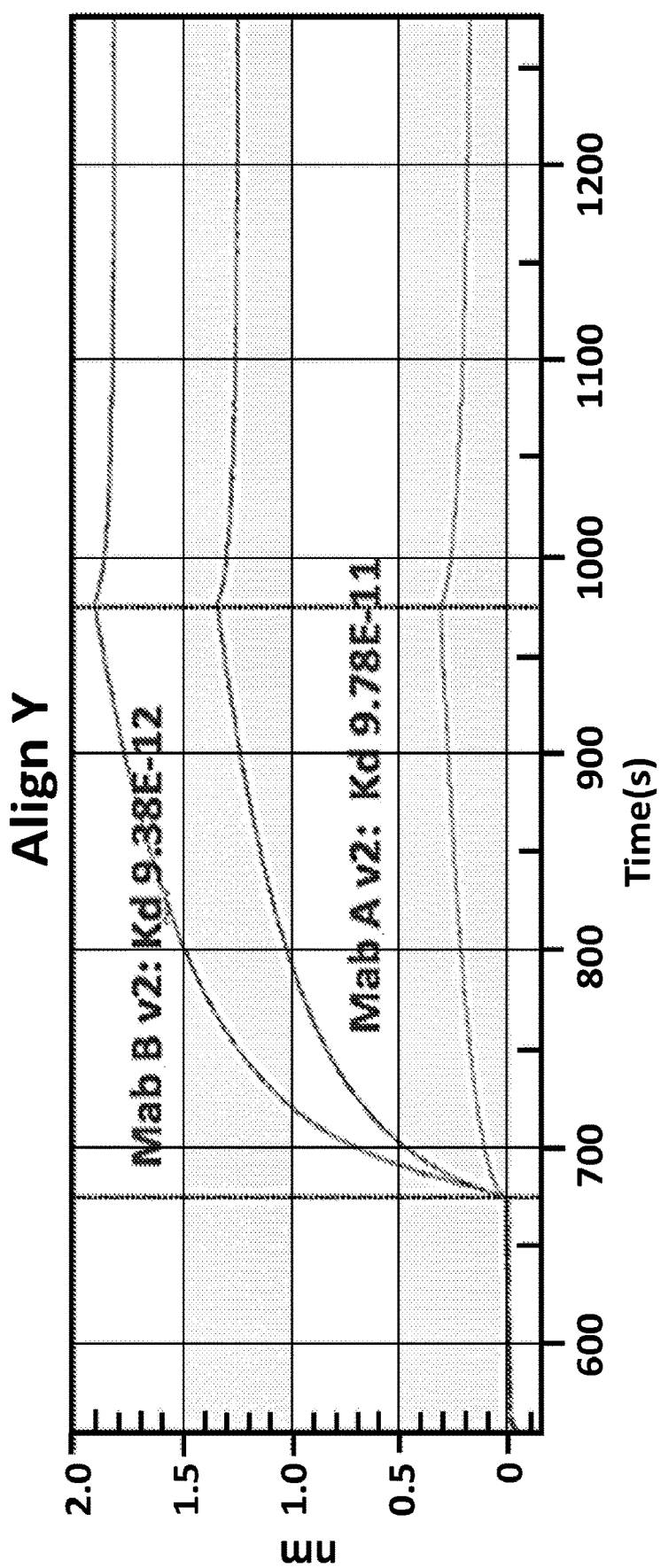
FIG. 2 shows Mab A v2 and Mab B v2 binding to VP2.

Table 1 provides a listing of certain sequences referenced herein.

TABLE 1

Description of Certain Sequences

| SEQ ID NO: | SEQUENCE | DESCRIPTION |
|---|---|---|
| 1 | ESENYRRVVVNNMDKTAVNGNMALDDIHAEIVTPWSLV | Epitope 1 |
| 2 | TPWRYYFQWDRTLIPSHTGTSGTPTNIYHGTDPDDVQFYTIENS | Epitope 2 |
| 3 | TPWRYYFQWDRTLIPSHTGTSGTP | Minimal epitope 2 |
| 4 | GFSLSSYHVH | Variable heavy chain CDR-H1 of Mab A |
| 5 | VMWNDGDTS | Variable heavy chain CDR-H2 of Mab A |
| 6 | PELPGLTYGVWFPY | Variable heavy chain CDR-H3 of Mab A |
| 7 | *QVQLKES*GPGLVQPSQTLSLTCTVS | Variable heavy chain framework region HC-FR1 of Mab A |
| 8 | *QVQLKES*GPGLVAPSQTLSLTCTVS | Variable heavy chain framework region HC-FR1 of Mab A variant 2 (v2) Q13A |
| 9 | WVRQPPGKGLEWLG | Variable region heavy chain framework region HC-FR2 of Mab A |
| 10 | YNLALNSRLSISRDTSKSQVFFKMSSLQTEDTATYYCAR | Variable heavy chain framework region HC-FR3 of Mab A |
| 11 | WGQGTLVTVSS | Variable heavy chain framework region HC-FR4 of Mab A |
| 12 | WGQGTLVTVSA | Variable heavy chain framework region HC-FR4 of Mab A variant 2 (v2) S11A |
| 13 | KASQNVDSNVD | Variable light chain CDR-L1 of Mab A |
| 14 | KASNRNT | Variable light chain CDR-L2 of Mab A |
| 15 | MQSTSYPLTF | Variable light chain CDR-L3 of Mab A |
| 16 | *DIVMTQTPA*SMSISVGDRVTMNC | Variable light chain framework region LC-FR1 of Mab A |
| 17 | WYQQKTGQSPNLLIY | Variable light chain framework region LC-FR2 of Mab A |
| 18 | GVPDRFTGSGSGTDFTFTISNMQAEDLAVYYC | Variable light chain framework region LC-FR3 of Mab A |
| 19 | GSGTKLEIK | Variable light chain framework region LC-FR4 of Mab A |

TABLE 1-continued

Description of Certain Sequences

| SEQ ID NO: | SEQUENCE | DESCRIPTION |
|---|---|---|
| 20 | *QVQLKES*GPGLVQPSQTLSLTCTVSGFSLSSYHVHWV RQPPGKGLEWLGVMWNDGDTSYNLALNSRLSISRDTS KSQVFFKMSSLQTEDTATYYCARPELPGLTYGVWFPY WGQGTLVTVSS | Variable heavy chain of Mab A (Mab A HC) |
| 21 | *QVQLKES*GPGLVAPSQTLSLTCTVSGFSLSSYHVHWV RQPPGKGLEWLGVMWNDGDTSYNLALNSRLSISRDTS KSQVFFKMSSLQTEDTATYYCARPELPGLTYGVWFPY WGQGTLVTVSA | Variable heavy chain of Mab A variant 2 HC-FR1 Q13A HC-FR4 S11A (Mab A HC v2) |
| 22 | *DIVMTQT*PASMSISVGDRVTMNCKASQNVDSNVDWYQ QKTGQSPNLLIYKASNRNTGVPDRFTGSGSGTDFTFT ISNMQAEDLAVYYCMQSTSYPLTFGSGTKLEIK | Variable light chain of Mab A (Mab A LC) |
| 23 | *QVQLKES*GPGLVQPSQTLSLTCTVSGFSLSSYHVHWV RQPPGKGLEWLGVMWNDGDTSYNLALNSRLSISRDTS KSQVFFKMSSLQTEDTATYYCARPELPGLTYGVWFPY WGQGTLVTVSSASTTAPSVFPLAPSCGSTSGSTVALA CLVSGYFPEPVTVSWNSGSLTSGVHTFPSVLQSSGLY SLSSMVTVPSSRWPSETFTCNVAHPASKTKVDKPVPK RENGRVPRPPDCPKCPAPEMLGGPSVFIFPPKPKDTL LIARTPEVTCVVVDLDPEDPEVQISWFVDGKQMQTAK TQPREEQFNGTYRVVSVLPIGHQDWLKGKQFTCKVNN KALPSPIERTISKARGQAHQPSVYVLPPSREELSKNT VSLTCLIKDFFPPDIDVEWQSNGQQEPESKYRTTPPQ LDEDGSYFLYSKLSVDKSRWQRGDTFICAVMHEALHN HYTQESLSHSPGK | Chimeric variable heavy chain of Mab A and canine IgG-B (Chimeric A HC IgG-B) |
| 24 | *QVQLKES*GPGLVAPSQTLSLTCTVSGFSLSSYHVHWV RQPPGKGLEWLGVMWNDGDTSYNLALNSRLSISRDTS KSQVFFKMSSLQTEDTATYYCARPELPGLTYGVWFPY WGQGTLVTVSAASTTAPSVFPLAPSCGSTSGSTVALA CLVSGYFPEPVTVSWNSGSLTSGVHTFPSVLQSSGLY SLSSMVTVPSSRWPSETFTCNVAHPASKTKVDKPVPK RENGRVPRPPDCPKCPAPEMLGGPSVFIFPPKPKDTL LIARTPEVTCVVVDLDPEDPEVQISWFVDGKQMQTAK TQPREEQFNGTYRVVSVLPIGHQDWLKGKQFTCKVNN KALPSPIERTISKARGQAHQPSVYVLPPSREELSKNT VSLTCLIKDFFPPDIDVEWQSNGQQEPESKYRTTPPQ LDEDGSYFLYSKLSVDKSRWQRGDTFICAVMHEALHN HYTQESLSHSPGK | Chimeric variable heavy chain of Mab A v2 and canine IgG-B HC-FR1 Q13A HC-FR4 S11A (Chimeric A HC v2 IgG-B) |
| 25 | *DIVMTQT*PASMSISVGDRVTMNCKASQNVDSNVDWYQ QKTGQSPNLLIYKASNRNTGVPDRFTGSGSGTDFTFT ISNMQAEDLAVYYCMQSTSYPLTFGSGTKLEIKRNDA QPAVYLFQPSPDQLHTGSASVVCLLNSFYPKDINVKW KVDGVIQDTGIQESVTEQDKDSTYSLSSTLTMSSTEY LSHELYSCEITHKSLPSTLIKSFQRSECQRVD | Chimeric variable light chain of Mab A and canine κ light constant region (Chimeric A LC κ) |
| 26 | MAVLGLLLCLVTFPSCVLS | Heavy chain leader |
| 27 | METDTLLLWVLLLWVPGSTG | Light chain leader |
| 28 | MAVLGLLLCLVTFPSCVLS*QVQLKES*GPGLVQPSQTL SLTCTVSGFSLSSYHVHWVRQPPGKGLEWLGVMWNDG DTSYNLALNSRLSISRDTSKSQVFFKMSSLQTEDTAT YYCARPELPGLTYGVWFPYWGQGTLVTVSSASTTAPS VFPLAPSCGSTSGSTVALACLVSGYFPEPVTVSWNSG SLTSGVHTFPSVLQSSGLYSLSSMVTVPSSRWPSETF TCNVAHPASKTKVDKPVPKRENGRVPRPPDCPKCPAP EMLGGPSVFIFPPKPKDILLIARTPEVICVVVDLDPE DPEVQISWFVDGKQMQTAKTQPREEQFNGTYRVVSVL PIGHQDWLKGKQFTCKVNNKALPSPIERTISKARGQA HQPSVYVLPPSREELSKNIVSLICLIKDFFPPDIDVE WQSNGQQEPESKYRTTPPQLDEDGSYFLYSKLSVDKS RWQRGDTFICAVMHEALHNHYTQESLSHSPGK | Chimeric variable heavy chain of Mab A and canine IgG-B with leader sequence (Chimeric A HC IgG-B with leader) |
| 29 | MAVLGLLLCLVTFPSCVLS*QVQLKES*GPGLVAPSQTL SLTCTVSGFSLSSYHVHWVRQPPGKGLEWLGVMWNDG DTSYNLALNSRLSISRDTSKSQVFFKMSSLQTEDTAT YYCARPELPGLTYGVWFPYWGQGTLVTVSAASTTAPS VFPLAPSCGSTSGSTVALACLVSGYFPEPVTVSWNSG SLTSGVHTFPSVLQSSGLYSLSSMVTVPSSRWPSETF | Chimeric variable heavy chain of Mab A v2 and canine IgG-B with leader sequence HC-FR1 Q13A HC-FR4 S11A |

TABLE 1-continued

Description of Certain Sequences

| SEQ ID NO: | SEQUENCE | DESCRIPTION |
|---|---|---|
| | TCNVAHPASKTKVDKPVPKRENGRVPRPPDCPKCPAP EMLGGPSVFIFPPKPKDILLIARTPEVICVVVDLDPE DPEVQISWFVDGKQMTAKTQPREEQFNGTYRVVSVL PIGHQDWLKGKQFTCKVNNKALPSPIERTISKARGQA HQPSVYVLPPSREELSKNIVSLICLIKDFFPPDIDVE WQSNGQQEPESKYRTTPPQLDEDGSYFLYSKLSVDKS RWQRGDTFICAVMHEALHNHYTQESLSHSPGK | (Chimeric A HC v2 IgG-B with leader) |
| 30 | METDTLLLWVLLLWVPGSTG*DIVMTQTPASMSISVGD RVTMNCKASQNVDSNVDWYQQKTGQSPNLLIYKASNR NTGVPDRFTGSGSGTDFTFTISNMQAEDLAVYYCMQS TSYPLTFGSGTKLEIKRNDAQPAVYLFQPSPDQLHTG SASVVCLLNSFYPKDINVKWKVDGVIQDTGIQESVTE QDKDSTYSLSSTLTMSSTEYLSHELYSCEITHKSLPS TLIKSFQRSECQRVD* | Chimeric variable light chain of Mab A and canine κ light constant region with leader sequence (Chimeric A LC κ with leader) |
| 31 | *QVQLKES*GPGLVQPSQTLSLTCTVSGFSLSSYHVHWV RQPPGKGLEWLGVMWNDGDTSYNLALNSRLSISRDTS KSQVFFKMSSLQTEDTATYYCARPELPGLTYGVWFPY WGQGTLVTVSSASTTAPSVFPLAPSCGTTSGATVALA CLVLGYFPEPVTVSWNSGALTSGVHTFPAVLQASGLY SLSSSMVTVPSSRWLSDTFTCNVAHPPSNTKVDKTVRK TDHPPGPKPCDCPKCPPPEMLGGPSIFIFPPKPKDTL SISRIPEVTCLVVDLGPDDSDVQITWFVDNTQVYTAK TSPREEQFNSTYRVVSVLPILHQDWLKGKEFKCKVNS KSLPSPIERTISKAKGQPHEPQVYVLPPAQEELSRNK VSVTCLIKSFHPPDIAVEWEITGQPEPENNYRTTPPQ LDSDGTYFVYSKLSVDRSHWQRGNTYTCSVSHEALHS HHTQKSLTQSPGK | Chimeric variable heavy chain of Mab A and feline IgG-1 (Chimeric A HC IgG-1) |
| 32 | *DIVMTQTPASMSISVGDRVTMNCKASQNVDSNVDWYQ QKTGQSPNLLIYKASNRNTGVPDRFTGSGSGTDFTFT ISNMQAEDLAVYYCMQSTSYPLTFGSGTKLEIKRSDA QPSVFLFQPSLDELHTGSASIVCILNDFYPKEVNVKW KVDGVVQNKGIQESTTEQNSKDSTYSLSSTLTMSSTE YQSHEKFSCEVTHKSLASTLVKSF*NRSECQRE | Chimeric variable light chain of Mab A and feline κ light constant region (Chimeric A LC κ) |
| 33 | *DIVMTQTPASMSISVGDRVTMNCKASQNVDSNVDWYQ QKTGQSPNLLIYKASNRNTGVPDRFTGSGSGTDFTFT ISNMQAEDLAVYYCMQSTSYPLTFGSGTKLEIKRSDA QPSVFLFQPSLDELHTGSASIVCILNDFYPKEVNVKW KVDGVVQNKGIQESTTEQNSKDSTYSLSSTLTMSSTE YQSHEKFSCEVTHKSLASTLVKSF*QRSECQRE | Chimeric variable light chain of Mab A and feline κ light constant region with no N-linked glycosylation site (Chimeric A LC κ aglycos) |
| 34 | MAVLGLLLCLVTFPSCVLSQVQLVESGGDLVKPGGTL RLSCTVSGFSLSSYHVHWVRQPPGKGLEWVAVMWNDG DTSYNLAVKGRFTISRDNAKNTLYLQMNSLRAEDTAV YYCARPELPGLTYGVWFPYWGQGTLVTVSSASTTAPS VFPLAPSCGSTSGSTVALACLVSGYFPEPVTVSWNSG SLTSGVHTFPSVLQSSGLYSLSSMVTVPSSRWPSETF TCNVAHPASKTKVDKPVPKRENGRVPRPPDCPKCPAP EMLGGPSVFIFPPKPKDILLIARTPEVICVVVDLDPE DPEVQISWFVDGKQMTAKTQPREEQFNGTYRVVSVL PIGHQDWLKGKQFTCKVNNKALPSPIERTISKARGQA HQPSVYVLPPSREELSKNIVSLICLIKDFFPPDIDVE WQSNGQQEPESKYRTTPPQLDEDGSYFLYSKLSVDKS RWQRGDTFICAVMHEALHNHYTQESLSHSPGK | Caninized variable heavy chain of Mab A v3 and canine IgG-B with leader sequence (Chimeric A HC v3 IgG-B with leader) |
| 85 | QVQLVESGGDLVKPGGTLRLSCTVSGFSLSSYHVHWV RQPPGKGLEWVAVMWNDGDTSYNLAVKGRFTISRDNA KNTLYLQMNSLRAEDTAVYYCARPELPGLTYGVWFPY WGQGTLVTVSS | Caninized variable heavy chain of Mab A v3 |
| 35 | MAVLGLLLCLVTFPSCVLSEVQLVESGGDLVKPGGTL RLSCTVSGFSLSSYHVHWVRQPPGKGLEWLGVMWNDG DTSYNLAVKGRFTISRDNAKNTLYFQMNSLRAEDTAT YYCARPELPGLTYGVWFPYWGQGTLVTVSSASTTAPS VFPLAPSCGSTSGSTVALACLVSGYFPEPVTVSWNSG SLTSGVHTFPSVLQSSGLYSLSSMVTVPSSRWPSETF TCNVAHPASKTKVDKPVPKRENGRVPRPPDCPKCPAP EMLGGPSVFIFPPKPKDILLIARTPEVICVVVDLDPE DPEVQISWFVDGKQMTAKTQPREEQFNGTYRVVSVL PIGHQDWLKGKQFTCKVNNKALPSPIERTISKARGQA | Caninized variable heavy chain of Mab A v4 and canine IgG-B with leader sequence (Caninized A HC v4 IgG-B with leader) |

TABLE 1-continued

Description of Certain Sequences

| SEQ ID NO: | SEQUENCE | DESCRIPTION |
|---|---|---|
|  | HQPSVYVLPPSREELSKNIVSLICLIKDFFPPDIDVE WQSNGQQEPESKYRTTPPQLDEDGSYFLYSKLSVDKS RWQRGDTFICAVMHEALHNHYTQESLSHSPGK |  |
| 86 | EVQLVESGGDLVKPGGTLRLSCTVSGFSLSSYHVHWV RQPPGKGLEWLGVMWNDGDTSYNLAVKGRFTISRDNA KNTLYFQMNSLRAEDTATYYCARPELPGLTYGVWFPY WGQGTLVTVSS | Caninized variable heavy chain of Mab A v4 |
| 36 | METDTLLLWVLLLWVPGSTGEIVMTQSPASLSLSQEE KVTITCKASQNVDSNVDWYQQKPGQAPKLLIYKASNR NTGVPSRFSGSGSGTDFSFTISSLEPEDVAVYYCMQS TSYPLTFGQGTKLEIKRNDAQPAVYLFQPSPDQLHTG SASVVCLLNSFYPKDINVKWKVDGVIQDTGIQESVTE QDKDSTYSLSSTLTMSSTEYLSHELYSCEITHKSLPS TLIKSFQRSECQRVD | Caninized variable light chain of Mab A and canine κ light constant region with leader sequence (Caninized A LC κ with leader) |
| 87 | EIVMTQSPASLSLSQEEKVTITCKASQNVDSNVDWYQ QKPGQAPKLLIYKASNRNTGVPSRFSGSGSGTDFSFT ISSLEPEDVAVYYCMQSTSYPLTFGQGTKLEIK | Caninized variable light chain of Mab A |
| 37 | QVQLVESGGDLVKPGGTLRLSCTVSGFSLSSYHVHWV RQPPGKGLEWVAVMWNDGDTSYNLAVKGRFTISRDNA KNTLYLQMNSLRAEDTAVYYCARPELPGLTYGVWFPY WGQGTLVTVSSASTTAPSVFPLAPSCGSTSGSTVALA CLVSGYFPEPVTVSWNSGSLTSGVHTFPSVLQSSGLY SLSSMVTVPSSRWPSETFTCNVAHPASKTKVDKPVPK RENGRVPRPPDCPKCPAPEMLGGPSVFIFPPKPKDTL LIARTPEVTCVVVDLDPEDPEVQISWFVDGKQMQTAK TQPREEQFNGTYRVVSVLPIGHQDWLKGKQFTCKVNN KALPSPIERTISKARGQAHQPSVYVLPPSREELSKNT VSLTCLIKDFFPPDIDVEWQSNGQQEPESKYRTTPPQ LDEDGSYFLYSKLSVDKSRWQRGDTFICAVMHEALHN HYTQESLSHSPGK | Caninized variable heavy chain of Mab A v3 and canine IgG-B (Caninized A HC v3 IgG-B) |
| 38 | EVQLVESGGDLVKPGGTLRLSCTVSGFSLSSYHVHWV RQPPGKGLEWLGVMWNDGDTSYNLAVKGRFTISRDNA KNTLYFQMNSLRAEDTATYYCARPELPGLTYGVWFPY WGQGTLVTVSSASTTAPSVFPLAPSCGSTSGSTVALA CLVSGYFPEPVTVSWNSGSLTSGVHTFPSVLQSSGLY SLSSMVTVPSSRWPSETFTCNVAHPASKTKVDKPVPK RENGRVPRPPDCPKCPAPEMLGGPSVFIFPPKPKDTL LIARTPEVTCVVVDLDPEDPEVQISWFVDGKQMQTAK TQPREEQFNGTYRVVSVLPIGHQDWLKGKQFTCKVNN KALPSPIERTISKARGQAHQPSVYVLPPSREELSKNT VSLTCLIKDFFPPDIDVEWQSNGQQEPESKYRTTPPQ LDEDGSYFLYSKLSVDKSRWQRGDTFICAVMHEALHN HYTQESLSHSPGK | Caninized variable heavy chain of Mab A v4 and canine IgG-B (Caninized A HC v4 IgG-B) |
| 39 | EIVMTQSPASLSLSQEEKVTITCKASQNVDSNVDWYQ QKPGQAPKLLIYKASNRNTGVPSRFSGSGSGTDFSFT ISSLEPEDVAVYYCMQSTSYPLTFGQGTKLEIKRNDA QPAVYLFQPSPDQLHTGSASVVCLLNSFYPKDINVKW KVDGVIQDTGIQESVTEQDKDSTYSLSSTLTMSSTEY LSHELYSCEITHKSLPSTLIKSFQRSECQRVD | Caninized variable light chain of Mab A and canine κ light constant region (Caninized A LC κ) |
| 40 | QLTLRESGPGLVKPSQSLSLTCTVSGFSLSSYHVHWI RQRPGRGLEWLGVMWNDGDTSYAFQGRISITADTAQN QFSLQLSSMTTDDTAVYYCARPELPGLTYGVWFPYWG QGALVTVS | Felinized variable heavy chain of Mab A (Felinized A HC) |
| 41 | AITMTQSPGSLAGSPGQQVTMNCKASQNVDSNVD WYQQKPGQHPKLLIYKASNRNTGVPDRFSGSGSG TDFTLTISNLQAEDVASYYCMQSTSYPLTFGQGT KLEIK | Felinized variable light chain of Mab A (Felinized A LC) |
| 42 | GFSLTSYGVS | Variable heavy chain CDR-H1 of Mab B |
| 43 | TMWNDGDTD | Variable heavy chain CDR-H2 of Mab B |
| 44 | SQLPGYNLRGWFVY | Variable heavy chain CDR-H3 of Mab B |

TABLE 1-continued

Description of Certain Sequences

| SEQ ID NO: | SEQUENCE | DESCRIPTION |
|---|---|---|
| 45 | QVQLKESGPGLVQPSQTLSLTCTVS | Variable heavy chain framework region HC-FR1 of Mab B |
| 46 | QVQLKESGPGLVQPSETLSLTCTVS | Variable heavy chain framework region HC-FR1 of Mab B variant 2 (v2) Q16E |
| 47 | WVRQPPGKGLEWIG | Variable region heavy chain framework region HC-FR2 of Mab B |
| 48 | WVRQPPGKGLEWMG | Variable region heavy chain framework region HC-FR2 of Mab B variant 2 (v2) I13M |
| 49 | YHSALRSRLSISRDSSKSQVLLKMNSLQTEDTAMYFCAR | Variable heavy chain framework region HC-FR3 of Mab B |
| 50 | YNSALRSKLSISRDTSKSQVFLKMNSLQTEDTAIYYCAR | Variable region heavy chain framework region HC-FR3 of Mab B variant 2 (v2) H2N R8K S15T L21F M34I F36Y |
| 51 | WGQGTLVIVS | Variable heavy chain framework region HC-FR4 of Mab B |
| 52 | KASHNINKNLE | Variable light chain CDR-L1 of Mab B |
| 53 | YANNLQT | Variable light chain CDR-L2 of Mab B |
| 54 | YQYNSGHTF | Variable light chain CDR-L3 of Mab B |
| 55 | DIVMTQTPSLLSASVGDRVTLNC | Variable light chain framework region LC-FR1 of Mab B |
| 56 | DIQMTQSPPVLSASVGDRVTLSC | Variable light chain framework region LC-FR1 of Mab B variant 2 (v2) V3Q T7S S9P L10V N22S |
| 57 | WYQQKLGEAPKLLIY | Variable light chain framework region LC-FR2 of Mab B |
| 58 | GISSRFSGSGSGTDYTLTISSLQPEDVATYYC | Variable light chain framework region LC-FR3 of Mab B |
| 59 | GIPSRFSGSGSGTDYTLTISSLQPEDVATYYC | Variable light chain framework region LC-FR3 of Mab B variant 2 (v2) S3P |
| 60 | GAGTKLELK | Variable light chain framework region LC-FR4 of Mab B |

TABLE 1-continued

Description of Certain Sequences

| SEQ ID NO: | SEQUENCE | DESCRIPTION |
|---|---|---|
| 61 | GAGTKLEIK | Variable light chain framework region LC-FR4 of Mab B variant 2 (v2) L8I |
| 62 | QVQLKESGPGLVQPSQTLSLTCTVSGFSLTSYGVSWV RQPPGKGLEWIGTMWNDGDTDYHSALRSRLSISRDSS KSQVLLKMNSLQTEDTAMYFCARSQLPGYNLRGWFVY WGQGTLVIVS | Variable heavy chain of Mab B (Mab B HC) |
| 63 | QVQLKESGPGLVQPSETLSLTCTVSGFSLTSYGVSWV RQPPGKGLEWMGTMWNDGDTDYNSALRSKLSISRDTS KSQVFLKMNSLQTEDTAIYYCARSQLPGYNLRGWFVY WGQGTLVIVS | Variable heavy chain of Mab B variant 2 HC-FR1 Q16E HC-FR2 I13M HC-FR3 H2N HC-FR3 R8K HC-FR3 S15T HC-FR3 L21F HC-FR3 M34I HC-FR3 F36Y (Mab B HC v2) |
| 64 | DIVMTQTPSLLSASVGDRVILNCKASHNINKNLEWYQ QKLGEAPKLLIYYANNLQTGISSRFSGSGSGTDYTLT ISSLQPEDVATYYCYQYNSGHTFGAGTKLELK | Variable light chain of Mab B (Mab B LC) |
| 65 | DIQMTQSPPVLSASVGDRVTLSCKASHNINKNLEWYQ QKLGEAPKLLIYYANNLQTGIPSRFSGSGSGTDYTLT ISSLQPEDVATYYCYQYNSGHTFGAGTKLEIK | Variable light chain of Mab B variant 2 LC-FR1 V3Q LC-FR1 T7S LC-FR1 S9P LC-FR1 L10V LC-FR1 N22S LC-FR3 S3P LC-FR4 L8I (Mab B LC v2) |
| 66 | QVQLKESGPGLVQPSQTLSLTCTVSGFSLTSYGVSWV RQPPGKGLEWIGTMWNDGDTDYHSALRSRLSISRDSS KSQVLLKMNSLQTEDTAMYFCARSQLPGYNLRGWFVY WGQGTLVIVSASTTAPSVFPLAPSCGSTSGSTVALAC LVSGYFPEPVTVSWNSGSLTSGVHTFPSVLQSSGLYS LSSMVTVPSSRWPSETFTCNVAHPASKTKVDKPVPKR ENGRVPRPPDCPKCPAPEMLGGPSVFIFPPKPKDTLL IARTPEVTCVVVDLDPEDPEVQISWFVDGKQMQTAKT QPREEQFNGTYRVVSVLPIGHQDWLKGKQFTCKVNNK ALPSPIERTISKARGQAHQPSVYVLPPSREELSKNTV SLTCLIKDFFPPDIDVEWQSNGQQEPESKYRTTPPQL DEDGSYFLYSKLSVDKSRWQRGDTFICAVMHEALHNH YTQESLSHSPGK | Chimeric variable heavy chain of Mab B and canine IgG-B (Chimeric B HC IgG-B) |
| 67 | QVQLKESGPGLVQPSETLSLTCTVSGFSLTSYGVSWV RQPPGKGLEWMGTMWNDGDTDYNSALRSKLSISRDTS KSQVFLKMNSLQTEDTAIYYCARSQLPGYNLRGWFVY WGQGTLVIVSASTTAPSVFPLAPSCGSTSGSTVALA CLVSGYFPEPVTVSWNSGSLTSGVHTFPSVLQSSGLY SLSSMVTVPSSRWPSETFTCNVAHPASKTKVDKPVPK RENGRVPRPPDCPKCPAPEMLGGPSVFIFPPKPKDTL LIARTPEVTCVVVDLDPEDPEVQISWFVDGKQMQTAK TQPREEQFNGTYRVVSVLPIGHQDWLKGKQFTCKVNN KALPSPIERTISKARGQAHQPSVYVLPPSREELSKNT VSLTCLIKDFFPPDIDVEWQSNGQQEPESKYRTTPPQ LDEDGSYFLYSKLSVDKSRWQRGDTFICAVMHEALHN HYTQESLSHSPGK | Chimeric variable heavy chain of Mab B v2 and canine IgG-B HC-FR1 Q16E HC-FR2 I13M HC-FR3 H2N HC-FR3 R8K HC-FR3 S15T HC-FR3 L21F HC-FR3 M34I HC-FR3 F36Y (Chimeric B HC v2 IgG-B) |
| 68 | DIVMTQTPSLLSASVGDRVILNCKASHNINKNLEWYQ QKLGEAPKLLIYYANNLQTGISSRFSGSGSGTDYTLT ISSLQPEDVATYYCYQYNSGHTFGAGTKLELKRNDAQ PAVYLFQPSPDQLHTGSASVVCLLNSFYPKDINVKWK VDGVIQDTGIQESVTEQDKDSTYSLSSTLTMSSTEYL SHELYSCEITHKSLPSTLIKSFQRSECQRVD | Chimeric variable light chain of Mab B and canine κ light constant region (Chimeric B LC κ) |
| 69 | DIQMTQSPPVLSASVGDRVTLSCKASHNINKNLEWYQ QKLGEAPKLLIYYANNLQTGIPSRFSGSGSGTDYTLT ISSLQPEDVATYYCYQYNSGHTFGAGTKLEIKRNDAQ | Chimeric variable light chain of Mab B v2 and canine κ light constant |

TABLE 1-continued

Description of Certain Sequences

| SEQ ID NO: | SEQUENCE | DESCRIPTION |
|---|---|---|
|  | PAVYLFQPSPDQLHTGSASVVCLLNSFYPKDINVKWK VDGVIQDTGIQESVTEQDKDSTYSLSSTLTMSSTEYL SHELYSCEITHKSLPSTLIKSFQRSECQRVD | region<br>LC-FR1 V3Q<br>LC-FR1 T7S<br>LC-FR1 S9P<br>LC-FR1 L10V<br>LC-FR1 N22S<br>LC-FR3 S3P<br>LC-FR4 L8I<br>(Chimeric B LC v2 κ) |
| 70 | MAVLGLLLCLVTFPSCVLS*QVQLKES*GPGLVQPSQTL SLTCTVSGFSLTSYGVSWVRQPPGKGLEWIGTMWNDG DTDYHSALRSRLSISRDSSKSQVLLKMNSLQTEDTAM YFCARSQLPGYNLRGWFVYWGQGTLVIVSASTTAPSV FPLAPSCGSTSGSTVALACLVSGYFPEPVTVSWNSGS LTSGVHTFPSVLQSSGLYSLSSMVTVPSSRWPSETFT CNVAHPASKTKVDKPVPKRENGRVPRPPDCPKCPAPE MLGGPSVFIFPPKPKDTLLIARTPEVTCVVVDLDPED PEVQISWFVDGKQMQTAKTQPREEQFNGTYRVVSVLP IGHQDWLKGKQFTCKVNNKALPSPIERTISKARGQAH QPSVYVLPPSREELSKNIVSLICLIKDFPPPDIDVEW QSNGQQEPESKYRTTPPQLDEDGSYFLYSKLSVDKSR WQRGDTFICAVMHEALHNHYTQESLSHSPGK | Chimeric variable heavy chain of Mab B and canine IgG-B with leader sequence (Canine chimeric B HC with leader) |
| 71 | MAVLGLLLCLVTFPSCVLS*QVQLKES*GPGLVQPSETL SLTCTVSGFSLTSYGVSWVRQPPGKGLEWMGTMWNDG DTDYNSALRSKLSISRDTSKSQVFLKMNSLQTEDTAI YYCARSQLPGYNLRGWFVYWGQGTLVIVSASTTAPS VFPLAPSCGSTSGSTVALACLVSGYFPEPVTVSWNSG SLTSGVHTFPSVLQSSGLYSLSSMVTVPSSRWPSETF TCNVAHPASKTKVDKPVPKRENGRVPRPPDCPKCPAP EMLGGPSVFIFPPKPKDTLLIARTPEVTCVVVDLDPE DPEVQISWFVDGKQMQTAKTQPREEQFNGTYRVVSVL PIGHQDWLKGKQFTCKVNNKALPSPIERTISKARGQA HQPSVYVLPPSREELSKNIVSLICLIKDFPPPDIDVE WQSNGQQEPESKYRTTPPQLDEDGSYFLYSKLSVDKS RWQRGDTFICAVMHEALHNHYTQESLSHSPGK | Chimeric variable heavy chain of Mab B v2 and canine IgG-B with leader sequence<br>HC-FR1 Q16E<br>HC-FR2 I13M<br>HC-FR3 H2N<br>HC-FR3 R8K<br>HC-FR3 S15T<br>HC-FR3 L21F<br>HC-FR3 M34I<br>HC-FR3 F36Y<br>(Canine chimeric B HC v2 IgG-B with leader) |
| 72 | METDTLLLWVLLLWVPGSTG*DIVMTQTPS*LLSASVGD RVTLNCKASHNINKNLEWYQQKLGEAPKLLIYYANNL QTGISSRFSGSGSGTDYTLTISSLQPEDVATYYCYQY NSGHTFGAGTKLELKRNDAQPAVYLFQPSPDQLHIGS ASVVCLLNSFYPKDINVKWKVDGVIQDTGIQESVTEQ DKDSTYSLSSTLTMSSTEYLSHELYSCEITHKSLPST LIKSFQRSECQRVD | Chimeric variable light chain of Mab B and canine κ light constant region with leader sequence (Canine chimeric B LC κ with leader) |
| 73 | METDTLLLWVLLLWVPGSTGDIQMTQSPPVLSASVGD RVTLSCKASHNINKNLEWYQQKLGEAPKLLIYYANNL QTGIPSRFSGSGSGTDYTLTISSLQPEDVATYYCYQY NSGHTFGAGTKLEIKRNDAQPAVYLFQPSPDQLHIGS ASVVCLLNSFYPKDINVKWKVDGVIQDTGIQESVTEQ DKDSTYSLSSTLTMSSTEYLSHELYSCEITHKSLPST LIKSFQRSECQRVD | Chimeric variable light chain of Mab B v2 and canine κ light constant region with leader sequence<br>LC-FR1 V3Q<br>LC-FR1 T7S<br>LC-FR1 S9P<br>LC-FR1 L10V<br>LC-FR1 N22S<br>LC-FR3 S3P<br>LC-FR4 L8I<br>(Canine chimeric B LC v2 κ with leader) |
| 74 | *QVQLKES*GPGLVQPSQTLSLTCTVSGFSLTSYGVSWV RQPPGKGLEWIGTMWNDGDTDYHSALRSRLSISRDSS KSQVLLKMNSLQTEDTAMYFCARSQLPGYNLRGWFVY WGQGTLVIVSASTTAPSVFPLAPSCGTTSGSTVALAC LVLGYFPEPVTVSWNSGALTSGVHTFPAVLQASGLYS LSSMVTVPSSRWLSDTFTCNVAHPPSNTKVDKTVRKT DHPPGPKPCDCPKCPPPEMLGGPSIFIFPPKPKDTLS ISRTPEVTCLVVDLGPDDSDVQITWFVDNTQVYTAKT SPREEQFNSTYRVVSVLPILHQDWLKGKEFKCKVNSK SLPSPIERTISKAKGQPHEPQVYVLPPAQEELSRNKV SVTCLIKSFHPPDIAVEWEITGQPEPENNYRTTPPQL DSDGTYFVYSKLSVDRSHWQRGNTYTCSVSHEALHSH HTQKSLIQSPGK | Chimeric variable heavy chain of Mab B and feline IgG-1 (Feline chimeric B HC IgG-1) |

TABLE 1-continued

Description of Certain Sequences

| SEQ ID NO: | SEQUENCE | DESCRIPTION |
|---|---|---|
| 75 | DIVMTQTPSLLSASVGDRVILNCKASHNINKNLEWYQ QKLGEAPKLLIYYANNLQTGISSRFSGSGSGTDYTLT ISSLQPEDVATYYCYQYNSGHTFGAGTKLELKRSDAQ PSVFLFQPSLDELHTGSASIVCILNDFYPKEVNVKWK VDGVVQNKGIQESTTEQNSKDSTYSLSSTLTMSSTEY QSHEKFSCEVTHKSLASTLVKSFNRSECQRE | Chimeric variable light chain of Mab B and feline κ light constant region (Feline chimeric B LC K) |
| 76 | DIVMTQTPSLLSASVGDRVILNCKASHNINKNLEWYQ QKLGEAPKLLIYYANNLQTGISSRFSGSGSGTDYTLT ISSLQPEDVATYYCYQYNSGHTFGAGTKLELKRSDAQ PSVFLFQPSLDELHTGSASIVCILNDFYPKEVNVKWK VDGVVQNKGIQESTTEQNSKDSTYSLSSTLTMSSTEY QSHEKFSCEVTHKSLASTLVKSFQRSECQRE | Chimeric variable light chain of Mab B and feline κ light constant region with no N-linked glycosylation site (Feline chimeric B LC κ aglycos) |
| 88 | EVQLVESGGDLVKPGGTLRLSCTVSGFSLTSYGVSWV RQSPGKGLEWIGTMWNDGDTDYHSAVKGQLSISRDTS KSQVFLQMNSLRAEDTAMYYCARSQLPGYNLRGWFVY WGQGTLVTVSS | Caninized variable heavy chain of Mab B v3 |
| 77 | MAVLGLLLCLVTFPSCVLSEVQLVESGGDLVKPGGTL RLSCTVSGFSLTSYGVSWVRQSPGKGLEWIGTMWNDG DTDYHSAVKGQLSISRDTSKSQVFLQMNSLRAEDTAM YYCARSQLPGYNLRGWFVYWGQGTLVTVSSASTTAPS VFPLAPSCGSTSGSTVALACLVSGYFPEPVTVSWNSG SLTSGVHTFPSVLQSSGLYSLSSMVTVPSSRWPSETF TCNVAHPASKTKVDKPVPKRENGRVPRPPDCPKCPAP EMLGGPSVFIFPPKPKDILLIARTPEVICVVVDLDPE DPEVQISWFVDGKQMTAKTQPREEQFNGTYRVVSVL PIGHQDWLKGKQFTCKVNNKALPSPIERTISKARGQA HQPSVYVLPPSREELSKNIVSLICLIKDFFPPDIDVE WQSNGQQEPESKYRTTPPQLDEDGSYFLYSKLSVDKS RWQRGDTFICAVMHEALHNHYTQESLSHSPGK | Caninized variable heavy chain of Mab B v3 and canine IgG-B with leader sequence (Caninized B HC v3 IgG-B with leader) |
| 78 | METDTLLLWVLLLWVPGSTGEIVLTQSPASLAVSLGQ RATISCKASHNINKNLEWYQQKPGQPPKLLIYYANNL QTGVPARFSGSGSGTDYSLNIHPMEEDDTAMYYCYQY NSGHTFGGGTKLEIKRNDAQPAVYLFQPSPDQLHTGS ASVVCLLNSFYPKDINVKWKVDGVIQDTGIQESVTEQ DKDSTYSLSSTLTMSSTEYLSHELYSCEITHKSLPST LIKSFQRSECQRVD | Caninized variable light chain of Mab B v3 and canine κ light constant region with leader sequence (Caninized B LC κ with leader) |
| 79 | EVQLVESGGDLVKPGGTLRLSCTVSGFSLTSYGVSWV RQSPGKGLEWIGTMWNDGDTDYHSAVKGQLSISRDTS KSQVFLQMNSLRAEDTAMYYCARSQLPGYNLRGWFVY WGQGTLVTVSSASTTAPSVFPLAPSCGSTSGSTVALA CLVSGYFPEPVTVSWNSGSLTSGVHTFPSVLQSSGLY SLSSMVTVPSSRWPSETFTCNVAHPASKTKVDKPVPK RENGRVPRPPDCPKCPAPEMLGGPSVFIFPPKPKDTL LIARTPEVTCVVVDLDPEDPEVQISWFVDGKQMTAK TQPREEQFNGTYRVVSVLPIGHQDWLKGKQFTCKVNN KALPSPIERTISKARGQAHQPSVYVLPPSREELSKNT VSLTCLIKDFFPPDIDVEWQSNGQQEPESKYRTTPPQ LDEDGSYFLYSKLSVDKSRWQRGDTFICAVMHEALHN HYTQESLSHSPGK | Caninized variable heavy chain of Mab B v3 and canine IgG-B (Caninized B HC v3 IgG-B) |
| 89 | EIVLTQSPASLAVSLGQRATISCKASHNINKNLEWYQ QKPGQPPKLLIYYANNLQTGVPARFSGSGSGTDYSLN IHPMEEDDTAMYYCYQYNSGHTFGGGTKLEIK | Caninized variable light chain of Mab B v3 |
| 80 | EIVLTQSPASLAVSLGQRATISCKASHNINKNLEWYQ QKPGQPPKLLIYYANNLQTGVPARFSGSGSGTDYSLN IHPMEEDDTAMYYCYQYNSGHTFGGGTKLEIKRNDAQ PAVYLFQPSPDQLHTGSASVVCLLNSFYPKDINVKWK VDGVIQDTGIQESVTEQDKDSTYSLSSTLTMSSTEYL SHELYSCEITHKSLPSTLIKSFQRSECQRVD | Caninized variable light chain of Mab B v3 and canine κ light constant region (Caninized B LC v3 κ) |
| 81 | GPGLVQPSQTLSLTCTVSGFSLSSYHVHWVRQPPGKG LEWLGVMWNDGDTSYNLALNSRLSISRDTSKSQVFFK MSSLQTEDTATYYCARPELPGLTYGVWFPYWGQGTLV TVS | Mab E variable HC |
| 82 | ASMSISVGDRVTMNCKASQNVDSNVDWYQQKTGQSPN LLIYKASNRNTGVPDRFTGSGSGTDFTFTISNMQAED LAVYYCMQSTSYPLIFGSGTKLEIKRA | Mab E variable LC |

TABLE 1-continued

Description of Certain Sequences

| SEQ ID NO: | SEQUENCE | DESCRIPTION |
|---|---|---|
| 83 | GPGLVQPSQTLSLTCTVSGFSLTSYGVSWVRQPPGKG LEWIGTMWNDGDTDYHSALRSRLSISRDSSKSQVLLK MNSLQTEDTAMYFCARSQLPGYNLRGWFVYWGQGTLV IVS | Mab F variable HC |
| 84 | SLLSASVGDRVTLNCKASHNINKNLEWYQQKLGEAPK LLIYYANNLQTGISSRFSGSGSGTDYTLTISSLQPED VATYYCYQYNSGHTFGAGTKLELKRA | Mab F variable LC |
| 90 | MWQLVSSTALLLLVSAGTQAADVPKAVVVLEPKW NRVLTMDSVTLKCQGDHLLRDNYTWLHNGRPISN QISTYIIKNASIKNSGEYRCQTDQSKLSDPVQLE VHTGWLLLQVPRLVFQEGELIQLKCHSWKNTPVR NVQYFQNGRGKKFFYNNSEYHIPAATSEHNGSYF CRGIIGKKNESSEAVNIIIQGSSLPSTSLLLSHW PQGSGSHHHHHH | Exemplary canine CD16 with linker, and poly-His |
| 91 | PAPEMLGGPSVFIFPPKPKDTLLIARTPEVTCVV VDLDPEDPEVQISWFVDGKQMQTAKTQPREEQFN GTYRVVSVLPIGHQDWLKGKQFTCKVNNKALPSP IERTISKARGQAHQPSVYVLPPSREELSKNTVSL TCLIKDFFPPDIDVEWQSNGQQEPESKYRTTPPQ LDEDGSYFLYSKLSVDKSRWQRGDTFICAVMHEA LHNHYTQESLSHSPGK | Exemplary wild-type canine IgG-B Fc |
| 92 | PAPEMLGGPDVFIFPPKPKDTLLIARTPEVTCVV VDLDPEDPEVQISWFVDGKQMQTAKTQPREEQFN GTYRVVSVLPIGHQDWLKGKQFTCKVNNKALPSP IERTISKARGQAHQPSVYVLPPSREELSKNTVSL TCLIKDFFPPDIDVEWQSNGQQEPESKYRTTPPQ LDEDGSYFLYSKLSVDKSRWQRGDTFICAVMHEA LHNHYTQESLSHSPGK | Exemplary variant canine IgG-B Fc CD16 enhancing binding mutant S10D |
| 93 | PAPEMLGGPEVFIFPPKPKDTLLIARTPEVTCVV VDLDPEDPEVQISWFVDGKQMQTAKTQPREEQFN GTYRVVSVLPIGHQDWLKGKQFTCKVNNKALPSP IERTISKARGQAHQPSVYVLPPSREELSKNTVSL TCLIKDFFPPDIDVEWQSNGQQEPESKYRTTPPQ LDEDGSYFLYSKLSVDKSRWQRGDTFICAVMHEA LHNHYTQESLSHSPGK | Exemplary variant canine IgG-B Fc CD16 enhancing binding mutant S10E |
| 94 | PAPEMLGGPSVFIFPPKPKDTLLIARTPEVTCVV VDLDPEDPEVQISWFVDGKQMQTAKTQPREEQFN GTYRVVSVLPIGHQDWLKGKQFTCKVNNKALPSP DERTISKARGQAHQPSVYVLPPSREELSKNTVSL TCLIKDFFPPDIDVEWQSNGQQEPESKYRTTPPQ LDEDGSYFLYSKLSVDKSRWQRGDTFICAVMHEA LHNHYTQESLSHSPGK | Exemplary variant canine IgG-B Fc CD16 enhancing binding mutant I103D |
| 95 | PAPEMLGGPSVFIFPPKPKDTLLIARTPEVTCVV VDLDPEDPEVQISWFVDGKQMQTAKTQPREEQFN GTYRVVSVLPIGHQDWLKGKQFTCKVNNKALPSP EERTISKARGQAHQPSVYVLPPSREELSKNTVSL TCLIKDFFPPDIDVEWQSNGQQEPESKYRTTPPQ LDEDGSYFLYSKLSVDKSRWQRGDTFICAVMHEA LHNHYTQESLSHSPGK | Exemplary variant canine IgG-B Fc CD16 enhancing binding mutant I103E |
| 96 | PAPEMLGGPDVFIFPPKPKDTLLIARTPEVTCVV VDLDPEDPEVQISWFVDGKQMQTAKTQPREEQFN GTYRVVSVLPIGHQDWLKGKQFTCKVNNKALPSP DERTISKARGQAHQPSVYVLPPSREELSKNTVSL TCLIKDFFPPDIDVEWQSNGQQEPESKYRTTPPQ LDEDGSYFLYSKLSVDKSRWQRGDTFICAVMHEA LHNHYTQESLSHSPGK | Exemplary variant canine IgG-B Fc CD16 enhancing binding mutant S10D I103D |
| 97 | PAPEMLGGPDVFIFPPKPKDTLLIARTPEVTCVV VDLDPEDPEVQISWFVDGKQMQTAKTQPREEQFN GTYRVVSVLPIGHQDWLKGKQFTCKVNNKALPSP EERTISKARGQAHQPSVYVLPPSREELSKNTVSL TCLIKDFFPPDIDVEWQSNGQQEPESKYRTTPPQ LDEDGSYFLYSKLSVDKSRWQRGDTFICAVMHEA LHNHYTQESLSHSPGK | Exemplary variant canine IgG-B Fc CD16 enhancing binding mutant S10D I103E |
| 98 | PAPEMLGGPEVFIFPPKPKDTLLIARTPEVTCVV VDLDPEDPEVQISWFVDGKQMQTAKTQPREEQFN | Exemplary variant canine IgG-B Fc |

TABLE 1-continued

| Description of Certain Sequences | | |
|---|---|---|
| SEQ ID NO: | SEQUENCE | DESCRIPTION |
| | GTYRVVSVLPIGHQDWLKGKQFTCKVNNKALPSP<br>DERTISKARGQAHQPSVYVLPPSREELSKNTVSL<br>TCLIKDFFPPDIDVEWQSNGQQEPESKYRTTPPQ<br>LDEDGSYFLYSKLSVDKSRWQRGDTFICAVMHEA<br>LHNHYTQESLSHSPGK | CD16 enhancing binding<br>mutant<br>S10E<br>I103D |
| 99 | PAPEMLGGPEVFIFPPKPKDTLLIARTPEVTCVV<br>VDLDPEDPEVQISWFVDGKQMQTAKTQPREEQFN<br>GTYRVVSVLPIGHQDWLKGKQFTCKVNNKALPSP<br>EERTISKARGQAHQPSVYVLPPSREELSKNTVSL<br>TCLIKDFFPPDIDVEWQSNGQQEPESKYRTTPPQ<br>LDEDGSYFLYSKLSVDKSRWQRGDTFICAVMHEA<br>LHNHYTQESLSHSPGK | Exemplary variant canine<br>IgG-B Fc<br>CD16 enhancing binding<br>mutant<br>S10E<br>I103E |

DESCRIPTION OF CERTAIN EMBODIMENTS

Antibodies that bind canine parvovirus and/or feline parvovirus are provided. Antibody heavy chains and light chains that are capable of forming antibodies that bind canine parvovirus and/or feline parvovirus are also provided. In addition, antibodies, heavy chains, and light chains comprising one or more particular complementary determining regions (CDRs) are provided. Polynucleotides encoding antibodies to canine parvovirus and/or feline parvovirus are provided. Methods of producing or purifying antibodies to canine parvovirus and/or feline parvovirus are also provided. Methods of providing passive immunity against infection with a canine or feline parvovirus and/or treatment of parvoviral infection using antibodies to canine parvovirus and/or feline parvovirus are provided.

For the convenience of the reader, the following definitions of terms used herein are provided.

As used herein, numerical terms such as Kd are calculated based upon scientific measurements and, thus, are subject to appropriate measurement error. In some instances, a numerical term may include numerical values that are rounded to the nearest significant figure.

As used herein, "a" or "an" means "at least one" or "one or more" unless otherwise specified. As used herein, the term "or" means "and/or" unless specified otherwise. In the context of a multiple dependent claim, the use of "or" when referring back to other claims refers to those claims in the alternative only.

Exemplary Parvovirus Antibodies

Novel antibodies directed against parvovirus are provided, for example antibodies that bind to canine parvovirus and/or feline parvovirus. Parvovirus antibodies provided herein include, but are not limited to, monoclonal antibodies, chimeric antibodies, caninized antibodies, and felinized antibodies.

Also provided herein are amino acid sequences of monoclonal parvovirus antibodies. For example, variable heavy chain CDRs (SEQ ID NOs: 4-6), variable light chain CDRs (SEQ ID NOs: 13-15), variable region heavy chain framework sequences (SEQ ID NOs: 7 and 8-11), and variable region light chain framework sequences (SEQ ID NOs: 16-19) for Mab A are provided. Also provided are variable heavy chain CDRs (SEQ ID NOs: 42-44), variable light chain CDRs (SEQ ID NOs: 52-54), variable region heavy chain framework sequences (SEQ ID NOs: 45, 47, 49, and 51), and variable region light chain framework sequences (SEQ ID NOs: 55, 57, 58, and 60) for Mab B. The amino acid sequences of the variable heavy chain and variable light chain of Mab A are provided (SEQ ID NOs: 20 and 22, respectively). The amino acid sequences of the variable heavy chain and variable light chain of Mab B are provided (SEQ ID NOs: 62 and 64, respectively).

In addition, the amino acid sequences of the CDRs, framework sequences, variable heavy and light chains of variant Mab A and Mab B antibodies are provided. The variable heavy chain CDRs (SEQ ID NOs 4-6), variable heavy chain framework regions (SEQ ID NOs: 8-10, and 12), the variable heavy chain (SEQ ID NO: 21), the variable light chain CDRs (SEQ ID NOs: 13-15), the variable light chain framework regions (SEQ ID NOSs: 16-19), and the variable light chain (SEQ ID NO: 22) of Mab A variant 2 (v2) are provided. The variable heavy chain CDRs (SEQ ID NOs 42-44), variable heavy chain framework regions (SEQ ID NOs: 46, 48, 50, and 51), the variable heavy chain (SEQ ID NO: 63), the variable light chain CDRs (SEQ ID NOs: 52-54), the variable light chain framework regions (SEQ ID NOSs: 56, 57, 59, and 61), and the variable light chain (SEQ ID NO: 65) of Mab B variant 2 (v2) are provided.

Also provided herein are chimeric canine, chimeric feline, caninized, and felinized antibodies derived from Mab A, Mab B, Mab A v2, and Mab B v2. In some embodiments, amino acid sequences of caninized and felinized Mab A, Mab B, Mab A v2, and Mab B v2 are provided, such as SEQ ID NOs: 34-41, 88, 77-80, 88, and 89. In some embodiments, amino acid sequences of chimeric antibodies derived from Mab A, Mab B, Mab A v2, and Mab B v2 are provided, such as SEQ ID NOs: 23-25, 28-33, and 66-76.

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments (such as Fab, F(ab')2, ScFv, minibody, diabody, triabody, and tetrabody) so long as they exhibit the desired antigen-binding activity. Canine, feline, and equine species have different varieties (classes) of antibodies that are shared by many mammalians.

The term antibody includes, but is not limited to, fragments that are capable of binding to an antigen, such as Fv, single-chain Fv (scFv), Fab, Fab', di-scFv, sdAb (single domain antibody) and (Fab')2 (including a chemically linked F(ab')2). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen combining sites and is still capable of cross-linking antigen. The term antibody also includes, but is not limited to, chimeric antibodies, humanized antibodies, and antibodies of various species such as mouse, human, cynomolgus monkey, canine, feline, equine, etc. Furthermore, for all antibody constructs provided herein, variants having the sequences from other organisms are also contemplated. Thus, if a murine version of an antibody is disclosed, one of skill in the art will appreciate how to transform the murine sequence based antibody into a cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, mouse scFv or a canine scFv). This denotes the sequences of at least part of the non-CDR regions, rather than the source of the construct. In some embodiments, the antibodies comprise a label or are conjugated to a second moiety.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

In some embodiments, the monoclonal antibody is Mab A, Mab A v2, Mab B, or Mab B v2.

"Amino acid sequence," means a sequence of amino acids residues in a peptide or protein. The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"Parvovirus" as used herein refers to any naturally occurring parvovirus or parvovirus variant, and includes canine parvovirus (CPV), such as CPV-2a, CPV-2b, and CPV-2c, and feline parvovirus (panleukopenia virus).

As used herein, the term "epitope" refers to a site on a target molecule (for example, an antigen, such as a protein, nucleic acid, carbohydrate or lipid) to which an antigen-binding molecule (for example, an antibody, antibody fragment, or scaffold protein containing antibody binding regions) binds. Epitopes often include a chemically active surface grouping of molecules such as amino acids, polypeptides or sugar side chains and have specific three dimensional structural characteristics as well as specific charge characteristics. Epitopes can be formed both from contiguous or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some examples an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between an antibody residue and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antibody. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

In some embodiments, the epitope comprises the amino acid sequence of SEQ ID NO: 1, SEQ ID NO: 2, and/or SEQ ID NO: 3.

The term "CDR" means a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, the contact definition, or a combination of the Kabat, Chothia, AbM, or contact definitions. The various CDRs within an antibody can be designated by their appropriate number and chain type, including, without limitation as CDR-H1, CDR-H2, CDR-H3, CDR-L1, CDR-L2, and CDR-L3. The term "CDR" is used herein to also encompass a "hypervariable region" or HVR, including hypervariable loops.

In some embodiments, a parvovirus antibody comprises a heavy chain comprising (a) a CDR-H1 comprising the amino acid sequence of SEQ ID NO: 4; (b) a CDR-H2 comprising the amino acid sequence of SEQ ID NO: 5; or (c) a CDR-H3 comprising the amino acid sequence of SEQ ID NO: 6. In some embodiments, a parvovirus antibody comprises a light chain comprising (a) a CDR-L1 comprising the amino acid sequence of SEQ ID NO: 13; (b) a CDR-L2 comprising the amino acid sequence of SEQ ID NO: 14; or (c) a CDR-L3 comprising the amino acid sequence of SEQ ID NO: 15.

In some embodiments, an a parvovirus antibody comprises a heavy chain comprising (a) a CDR-H1 comprising the amino acid sequence of SEQ ID NO: 42; (b) a CDR-H2 comprising the amino acid sequence of SEQ ID NO: 43; or (c) a CDR-H3 comprising the amino acid sequence of SEQ ID NO: 44. In some embodiments, a parvovirus antibody comprises a light chain comprising (a) a CDR-L1 comprising the amino acid sequence of SEQ ID NO: 52; (b) a CDR-L2 comprising the amino acid sequence of SEQ ID NO: 53; or (c) a CDR-L3 comprising the amino acid sequence of SEQ ID NO: 54.

In some embodiments, a parvovirus antibody comprises a heavy chain comprising (a) a CDR-H1 comprising the amino acid sequence of SEQ ID NO: 4 or a variant thereof wherein 1, 2, or 3 amino acids of the CDR-H1 is substituted by a different amino acid; (b) a CDR-H2 comprising the amino acid sequence of SEQ ID NO: 5 or a variant thereof wherein 1, 2, or 3 amino acids of the CDR-H2 is substituted by a different amino acid; and/or (c) a CDR-H3 comprising the amino acid sequence of SEQ ID NO: 6 or a variant thereof wherein 1, 2, or 3 amino acids of the CDR-H3 is substituted by a different amino acid. In some embodiments, a parvovirus antibody comprises a light chain comprising (a) a CDR-L1 comprising the amino acid sequence of SEQ ID NO: 13 or a variant thereof wherein 1, 2, or 3 amino acids of the CDR-L1 is substituted by a different amino acid; (b) a CDR-L2 comprising the amino acid sequence of SEQ ID NO: 14 or a variant thereof wherein 1, 2, or 3 amino acids of the CDR-L2 is substituted by a different amino acid; and/or (c) a CDR-L3 comprising the amino acid sequence of SEQ ID NO: 15 or a variant thereof wherein 1, 2, or 3 amino acids of the CDR-L3 is substituted by a different amino acid.

In some embodiments, an a parvovirus antibody comprises a heavy chain comprising (a) a CDR-H1 comprising the amino acid sequence of SEQ ID NO: 42 or a variant thereof wherein 1, 2, or 3 amino acids of the CDR-H1 is substituted by a different amino acid; (b) a CDR-H2 comprising the amino acid sequence of SEQ ID NO: 43 or a variant thereof wherein 1, 2, or 3 amino acids of the CDR-H2 is substituted by a different amino acid; and/or (c) a CDR-H3 comprising the amino acid sequence of SEQ ID NO: 44 or a variant thereof wherein 1, 2, or 3 amino acids of the CDR-H3 is substituted by a different amino acid. In some embodiments, a parvovirus antibody comprises a light chain comprising (a) a CDR-L1 comprising the amino acid sequence of SEQ ID NO: 52 or a variant thereof wherein 1, 2, or 3 amino acids of the CDR-L1 is substituted by a different amino acid; (b) a CDR-L2 comprising the amino acid sequence of SEQ ID NO: 53 or a variant thereof wherein 1, 2, or 3 amino acids of the CDR-L2 is substituted by a different amino acid; and/or (c) a CDR-L3 comprising the amino acid sequence of SEQ ID NO: 54 or a variant thereof wherein 1, 2, or 3 amino acids of the CDR-L3 is substituted by a different amino acid.

The term "variable region" as used herein refers to a region comprising at least three CDRs. In some embodiments, the variable region includes the three CDRs and at least one framework region ("FR"). The terms "heavy chain variable region" or "variable heavy chain" are used interchangeably to refer to a region comprising at least three heavy chain CDRs. The terms "light chain variable region" or "variable light chain" are used interchangeably to refer to a region comprising at least three light chain CDRs. In some embodiments, the variable heavy chain or variable light chain comprises at least one framework region. In some embodiments, an antibody comprises at least one heavy chain framework region selected from HC-FR1, HC-FR2, HC-FR3, and HC-FR4. In some embodiments, an antibody comprises at least one light chain framework region selected from LC-FR1, LC-FR2, LC-FR3, and LC-FR4. The framework regions may be juxtaposed between light chain CDRs or between heavy chain CDRs. For example, an antibody may comprise a variable heavy chain having the following structure: (HC-FR1)-(CDR-H1)-(HC-FR2)-(CDR-H2)-(HC-FR3)-(CDR-H3)-(HC-FR4). An antibody may comprise a variable heavy chain having the following structure: (CDR-H1)-(HC-FR2)-(CDR-H2)-(HC-FR3)-(CDR-H3). An antibody may also comprise a variable light chain having the following structure: (LC-FR1)-(CDR-L1)-(LC-FR2)-(CDR-L2)-(LC-FR3)-(CDR-L3)-(LC-FR4). An antibody may also comprise a variable light chain having the following structure: (CDR-L1)-(LC-FR2)-(CDR-L2)-(LC-FR3)-(CDR-L3).

In some embodiments, a parvovirus antibody comprises one or more of (a) a variable region heavy chain framework 1 (HC-FR1) sequence of SEQ ID NO: 7 or SEQ ID NO: 8, (b) a HC-FR2 sequence of SEQ ID NO: 9, (c) a HC-FR3 sequence of SEQ ID NO: 10, (d) a HC-FR4 sequence of SEQ ID NO: 11 or SEQ ID NO: 12, (e) a variable region light chain framework 1 (LC-FR1) sequence of SEQ ID NO: 16, (f) an LC-FR2 sequence of SEQ ID NO: 17, (g) an LC-FR3 sequence of SEQ ID NO: 18, or (h) an LC-FR4 sequence of SEQ ID NO: 19.

In some embodiments, a parvovirus antibody comprises one or more of (a) a variable region heavy chain framework 1 (HC-FR1) sequence of SEQ ID NO: 45 or SEQ ID NO: 46, (b) a HC-FR2 sequence of SEQ ID NO: 47 or SEQ ID NO: 48, (c) a HC-FR3 sequence of SEQ ID NO: 49 or SEQ ID NO: 50, (d) a HC-FR4 sequence of SEQ ID NO: 51, (e) a variable region light chain framework 1 (LC-FR1) sequence of SEQ ID NO: 55 or SEQ ID NO: 56, (f) an LC-FR2 sequence of SEQ ID NO: 57, (g) an LC-FR3 sequence of SEQ ID NO: 58 or SEQ ID NO: 59, or (h) an LC-FR4 sequence of SEQ ID NO: 60.

In some embodiments, a parvovirus antibody comprises a variable light chain sequence of SEQ ID NO: 22, SEQ ID NO: 87, SEQ ID NO: 41, SEQ ID NO: 64, SEQ ID NO: 65, SEQ ID NO: 89, SEQ ID NO: 82, or SEQ ID NO: 84. In some embodiments, a parvovirus antibody comprises a variable heavy chain sequence of SEQ ID NO: 20, SEQ ID NO: 21, SEQ ID NO: 85, SEQ ID NO: 86, SEQ ID NO: 40, SEQ ID NO: 62, SEQ ID NO: 63, SEQ ID NO: 88, SEQ ID NO: 81, or SEQ ID NO: 83.

In some embodiments, a parvovirus antibody comprises a variable heavy chain sequence of SEQ ID NO: 20 and a variable light chain sequence of SEQ ID NO: 22. In some embodiments, a parvovirus antibody comprises a variable heavy chain sequence of SEQ ID NO: 21 and a variable light chain sequence of SEQ ID NO: 22. In some embodiments, a parvovirus antibody comprises a variable heavy chain sequence of SEQ ID NO: 85 and a variable light chain sequence of SEQ ID NO: 87. In some embodiments, a parvovirus antibody comprises a variable heavy chain sequence of SEQ ID NO: 86 and a variable light chain sequence of SEQ ID NO: 87. In some embodiments, a parvovirus antibody comprises a variable heavy chain sequence of SEQ ID NO: 40 and a variable light chain sequence of SEQ ID NO: 41. In some embodiments, a parvovirus antibody comprises a variable heavy chain sequence of SEQ ID NO: 62 and a variable light chain sequence of SEQ ID NO: 64 or SEQ ID NO: 65. In some embodiments, a parvovirus antibody comprises a variable heavy chain sequence of SEQ ID NO: 63 and a variable light chain sequence of SEQ ID NO: 64 or SEQ ID NO: 65. In some embodiments, a parvovirus antibody comprises a variable heavy chain sequence of SEQ ID NO: 88 and a variable light chain sequence of SEQ ID NO: 89.

The term "constant region" as used herein refers to a region comprising at least three constant domains. The terms "heavy chain constant region" or "constant heavy chain" are used interchangeably to refer to a region comprising at least three heavy chain constant domains, CH1, CH2, and CH3. Nonlimiting exemplary heavy chain constant regions include γ, δ, α, ε, and μ. Each heavy chain constant region corresponds to an antibody isotype. For example, an antibody comprising a γ constant region is an IgG antibody, an antibody comprising a δ constant region is an IgD antibody, an antibody comprising an α constant region is an IgA antibody, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgA1 (comprising an $\alpha_1$ constant region) and IgA2 (comprising an $\alpha_2$ constant region) antibodies; and IgM antibodies include, but are not limited to IgM1 and IgM2. The terms "light chain constant region" or "constant light chain" are used interchangeably to refer to a region comprising a light chain constant domain, CL. Nonlimiting exemplary light chain constant regions include λ and κ. Non-function-altering deletions and alterations within the domains are encompassed within the scope of the term "constant region" unless designated otherwise. Canine and feline have antibody classes such as IgG, IgA, IgD, IgE, and IgM. Within the canine IgG antibody class are IgG-A, IgG-B, IgG-C, and IgG-D. Within the feline IgG antibody class are IgG1, IgG2a, and IgG2b.

The term "chimeric antibody" or "chimeric" refers to an antibody in which a portion of the heavy chain or light chain is derived from a particular source or species, while at least a part of the remainder of the heavy chain or light chain is derived from a different source or species. In some embodiments, a chimeric antibody refers to an antibody comprising at least one variable region from a first species (such as mouse, rat, cynomolgus monkey, etc.) and at least one constant region from a second species (such as human, dog, cat, equine, etc.). In some embodiments, a chimeric antibody comprises at least one mouse variable region and at least one canine constant region. In some embodiments, a chimeric antibody comprises at least one mouse variable region and at least one feline constant region. In some embodiments, all of the variable regions of a chimeric antibody are from a first species and all of the constant regions of the chimeric antibody are from a second species. In some embodiments, a chimeric antibody comprises a constant heavy chain region or constant light chain region from a companion animal. In some embodiments, a chimeric antibody comprises a mouse variable heavy and light chains and a companion animal constant heavy and light chains. For example, a chimeric antibody may comprise a mouse variable heavy and light chains and a canine constant heavy and light chains; a chimeric antibody may comprise a mouse variable heavy and light chains and a feline constant heavy and light chains; or a chimeric antibody may comprise a mouse variable heavy and light chains and an equine constant heavy and light chains.

In some embodiments, a parvovirus antibody comprises a chimeric antibody comprising: (a) (i) a heavy chain amino acid sequence of SEQ ID NO: 23; (ii) a light chain amino acid sequence of SEQ ID NO: 25; or (iii) a heavy chain amino acid sequence as in (i) and a light chain sequence as in (ii); (b) (i) a heavy chain amino acid sequence of SEQ ID NO: 24; (ii) a light chain amino acid sequence of SEQ ID NO: 25; or (iii) a heavy chain amino acid sequence as in (i) and a light chain sequence as in (ii); (c) (i) a heavy chain amino acid sequence of SEQ ID NO: 31; (ii) a light chain amino acid sequence of SEQ ID NO: 32; or (iii) a heavy chain amino acid sequence as in (i) and a light chain sequence as in (ii); (d) (i) a heavy chain amino acid sequence of SEQ ID NO: 31; (ii) a light chain amino acid sequence of SEQ ID NO: 33; or (iii) a heavy chain amino acid sequence as in (i) and a light chain sequence as in (ii); (e) (i) a heavy chain amino acid sequence of SEQ ID NO: 66; (ii) a light chain amino acid sequence of SEQ ID NO: 68; or (iii) a heavy chain amino acid sequence as in (i) and a light chain sequence as in (ii); (f) (i) a heavy chain amino acid sequence of SEQ ID NO: 67; (ii) a light chain amino acid sequence of SEQ ID NO: 69; or (iii) a heavy chain amino acid sequence as in (i) and a light chain sequence as in (ii); (g) (i) a heavy chain amino acid sequence of SEQ ID NO: 74; (ii) a light chain amino acid sequence of SEQ ID NO: 75; or (iii) a heavy chain amino acid sequence as in (i) and a light chain sequence as in (ii); or (h) (i) a heavy chain amino acid sequence of SEQ ID NO: 74; (ii) a light chain amino acid sequence of SEQ ID NO: 75; or (iii) a heavy chain amino acid sequence as in (i) and a light chain sequence as in (ii).

A "canine chimeric," "chimeric canine," or "canine chimeric antibody" refers to a chimeric antibody having at least a portion of a heavy chain or a portion of a light chain derived from a dog. A "feline chimeric," "chimeric feline," or "feline chimeric antibody" refers to a chimeric antibody having at least a portion of a heavy chain or a portion of a light chain derived from a cat. In some embodiments, a canine chimeric antibody comprises a mouse or rat variable heavy and light chains and a canine constant heavy and light chains. In some embodiments, a feline chimeric antibody comprises a mouse or rat variable heavy and light chains and a feline constant heavy and light chains.

In some embodiments, a parvovirus antibody comprises a canine heavy chain constant region selected from an IgG-A, IgG-B, IgG-C, and IgG-D constant region.

In some embodiments, a parvovirus antibody comprises a feline heavy chain constant region selected from an IgG1, IgG2a, and IgG2b constant region.

A "caninized antibody" means an antibody in which at least one amino acid in a portion of a non-canine variable region has been replaced with the corresponding amino acid from a canine variable region. In some embodiments, a caninized antibody comprises at least one canine constant region (e.g., a γ constant region, an α constant region, a δ constant region, an ε constant region, a μ constant region, or etc.) or fragment thereof. In some embodiments, a caninized antibody is an antibody fragment, such as Fab, scFv, (Fab')₂, etc. The term "caninized" also denotes forms of non-canine (for example, murine) antibodies that are chimeric immunoglobulins, immunoglobulin chains, or fragments thereof (such as Fv, Fab, Fab', F(ab')₂ or other antigen-binding sequences of antibodies) that contain minimal sequence of non-canine immunoglobulin. Caninized antibodies can include canine immunoglobulins (recipient antibody) in which residues from a CDR of the recipient are substituted by residues from a CDR of a non-canine species (donor antibody) such as mouse, rat, or rabbit having the desired specificity, affinity, and capacity. In some instances, Fv framework region (FR) residues of the canine immunoglobulin are replaced by corresponding non-canine residues. Furthermore, the caninized antibody can comprise residues that are found neither in the recipient antibody nor in the imported CDR or framework sequences, but are included to further refine and optimize antibody performance.

In some embodiments, at least one amino acid residue in a portion of a rat or a mouse variable heavy chain or a rat or a mouse variable light chain has been replaced with the corresponding amino acid from a canine variable region. In some embodiments, the modified chain is fused to a canine constant heavy chain or a canine constant light chain.

A "felinized antibody" means an antibody in which at least one amino acid in a portion of a non-feline variable region has been replaced with the corresponding amino acid from a feline variable region. In some embodiments, a felinized antibody comprises at least one feline constant region (e.g., a γ constant region, an α constant region, a δ constant region, an ε constant region, a μ constant region, or etc.) or fragment thereof. In some embodiments, a felinized antibody is an antibody fragment, such as Fab, scFv, (Fab')₂, etc. The term "felinized" also denotes forms of non-feline (for example, murine) antibodies that are chimeric immunoglobulins, immunoglobulin chains, or fragments thereof (such as Fv, Fab, Fab', F(ab')₂ or other antigen-binding sequences of antibodies) that contain minimal sequence of non-feline immunoglobulin. Felinized antibodies can include feline immunoglobulins (recipient antibody) in which residues from a CDR of the recipient are substituted by residues from a CDR of a non-feline species (donor antibody) such as mouse, rat, or rabbit having the desired specificity, affinity, and capacity. In some instances, Fv framework region (FR) residues of the feline immunoglobulin are replaced by corresponding non-feline residues. Furthermore, the felinized antibody can comprise residues that are found neither in the recipient antibody nor in the imported CDR or framework sequences, but are included to further refine and optimize antibody performance.

In some embodiments, at least one amino acid residue in a portion of a mouse variable heavy chain or a mouse variable light chain has been replaced with the corresponding amino acid from a feline variable region. In some embodiments, the modified chain is fused to a feline constant heavy chain or a canine constant light chain.

A "fragment crystallizable polypeptide" or "Fc polypeptide" is the portion of an antibody molecule that interacts with effector molecules and cells. It comprises the C-terminal portions of the immunoglobulin heavy chains. As used herein, an Fc polypeptide includes fragments of the Fc domain having one or more biological activities of an entire Fc polypeptide. An "effector function" of the Fc polypeptide is an action or activity performed in whole or in part by any antibody in response to a stimulus and may include complement fixation and/or ADCC (antibody-dependent cellular cytotoxicity) induction and/or ADCP (antibody-dependent cellular phagocytosis).

In some embodiments, a biological activity of an Fc polypeptide is the ability to bind FcRn. In some embodiments, a biological activity of an Fc polypeptide is the ability to bind C1q. In some embodiments, a biological activity of an Fc polypeptide is the ability to bind CD16. In some embodiments, a biological activity of an Fc polypeptide is the ability to bind protein A.

The term "IgX Fc" means the Fc region is derived from a particular antibody isotype (e.g., IgG, IgA, IgD, IgE, IgM, etc.), where "X" denotes the antibody isotype. Thus, "IgG Fc" denotes the Fc region of a γ chain, "IgA Fc" denotes the Fc region of an α chain, "IgD Fc" denotes the Fc region of a δ chain, "IgE Fc" denotes the Fc region of an ε chain, "IgM Fc" denotes the Fc region of a μ chain, etc. In some embodiments, the IgG Fc region comprises CH1, hinge, CH2, CH3, and CL1. "IgX-N-Fc" denotes that the Fc region is derived from a particular subclass of antibody isotype (such as canine IgG subclass A, B, C, or D; or feline IgG subclass 1, 2a, or 2b), where "N" denotes the subclass. In some embodiments, IgX Fc or IgX-N-Fc regions are derived from a companion animal, such as a dog or a cat. In some embodiments, IgG Fc regions are isolated from canine γ heavy chains, such as IgG-A, IgG-B, IgG-C, or IgG-D. In some instances, IgG Fc regions are isolated from feline γ heavy chains, such as IgG1, IgG2a, or IgG2b. Antibodies comprising an Fc region of IgG-A, IgG-B, IgG-C, or IgG-D may provide for higher expression levels in recombination production systems.

The terms "IgX Fc" and "IgX Fc polypeptide" include wild-type IgX Fc polypeptides and variant IgX Fc polypeptides, unless indicated otherwise.

In some embodiments, a variant IgG Fc polypeptide comprises a variant IgG Fc polypeptide of a companion animal species. In some embodiments, a variant IgG Fc polypeptide comprises a variant canine IgG Fc polypeptide or a feline IgG Fc polypeptide. In some embodiments, a variant IgG Fc polypeptide (e.g., a variant canine IgG-A Fc polypeptide, a variant canine IgG-C Fc polypeptide, or a variant canine IgG-D Fc polypeptide, variant feline IgG1a Fc polypeptide, variant feline IgG1b Fc polypeptide, or variant feline IgG2 Fc polypeptide) has an activity that the reference (e.g., wild-type) polypeptide substantially lacks.

An antibody may be modified to extend or shorten its half-life. In some embodiments involving a higher dose of antibody, a shorter half-life may be desirable for acute treatment. In some embodiments involving a lower dose of antibody, a longer half-life may be desirable for prolonged treatment. For example, as discussed below, mutations in IgG Fc that affect FcRn interactions may be introduced.

In some embodiments, a parvovirus antibody comprises a wild-type or variant IgG Fc having complement fixation activity (or complement-dependent cytotoxicity (CDC)). In some embodiments, a parvovirus antibody comprises a wild-type or variant IgG Fc having antibody-dependent cellular cytotoxicity (ADCC) activity. In some embodiments, a parvovirus antibody comprises a wild-type or variant IgG Fc having antibody-dependent cellular phagocytosis (ADCP) activity. In some embodiments, a parvovirus antibody comprises a wild-type or variant IgG Fc having complement fixation activity and/or ADCC activity and/or ADCP activity. IgG Fc polypeptides may be modified to have an effector function or to have an enhanced effector function.

In some embodiments, a parvovirus antibody comprises a wild-type or variant IgG Fc the binds to canine FcRn at low pH. In some embodiments, a parvovirus comprises a wild-type or variant IgG Fc that binds to C1q. In some embodiments, a parvovirus comprises a wild-type or variant IgG Fc that binds to CD16. In some embodiments, a parvovirus comprises a variant IgG Fc comprising one or more afucosylated glycan.

In some embodiments, a variant IgG Fc (e.g., a variant canine IgG Fc polypeptide or a variant feline IgG Fc polypeptide) has modified FcRn binding affinity compared to a reference polypeptide. In some embodiments, a variant IgG Fc has increased FcRn binding affinity at an acidic pH (e.g., at a pH in the range of from about 5.0 to about 6.5, such as at a pH of about 5.0, a pH of about 5.5, a pH of about 6.0, or a pH of about 6.5) compared to a reference polypeptide. Exemplary variant IgG Fc polypeptides having increased FcRn binding affinity are disclosed in WO 2020/082048, which is incorporated by reference herein in its entirety.

In some embodiments, a variant IgG Fc (e.g., a variant canine IgG Fc polypeptide or a variant feline IgG Fc polypeptide) has modified C1q binding affinity compared to a reference polypeptide. In some embodiments, a variant IgG Fc has increased C1q binding affinity compared to a reference polypeptide. Exemplary variant IgG Fc polypeptides having increased C1q binding affinity are disclosed in WO 2020/139984 (e.g., Example 2), which is incorporated by reference herein in its entirety.

In some embodiments, a variant IgG Fc (e.g., a variant canine IgG Fc polypeptide or a variant feline IgG Fc polypeptide) has modified CD16 binding affinity compared to a reference polypeptide. In some embodiments, a variant IgG Fc has increased CD16 binding affinity compared to a reference polypeptide. Exemplary variant IgG Fc polypeptides having increased CD16 binding affinity are disclosed in WO 2020/139984 (e.g., Example 2), which is incorporated by reference herein in its entirety.

In some embodiments, a variant canine IgG Fc has enhanced CD16 binding affinity compared to a reference polypeptide. In some embodiments a variant IgG Fc comprises a) an aspartic acid or a glutamic acid at a position corresponding to position 10 of SEQ ID NO: 91; b) an aspartic acid or a glutamic acid at position 10 of SEQ ID NO: 91; c) an aspartic acid or a glutamic acid at a position corresponding to position 103 of SEQ ID NO: 91; d) an aspartic acid or a glutamic acid at position 103 of SEQ ID NO: 91; e) an aspartic acid or a glutamic acid at a position corresponding to position 10 and/or position 103 of SEQ ID NO: 91; f) an aspartic acid or a glutamic acid at position 10 and/or position 103 of SEQ ID NO: 91. In some embodiments a variant IgG Fc comprises the amino acid sequence of SEQ ID NO: 92, SEQ ID NO: 93, SEQ ID NO: 94, SEQ ID NO: 95, SEQ ID NO: 96, SEQ ID NO: 97, SEQ ID NO: 98, or SEQ ID NO: 99.

In some embodiments, a variant IgG Fc (e.g., a variant canine IgG Fc polypeptide or a variant feline IgG Fc polypeptide) has modified Protein A binding affinity compared to a reference polypeptide. In some embodiments, a variant IgG Fc has increased Protein A binding affinity compared to a reference polypeptide. Exemplary variant IgG Fc polypeptides having increased Protein A binding affinity are disclosed in WO 2020/139984 (e.g., Example 2), which is incorporated by reference herein in its entirety.

The term "affinity" means the strength of the sum total of noncovalent interactions between a single binding site of a molecule (for example, an antibody) and its binding partner (for example, an antigen). The affinity of a molecule X for its partner Y can generally be represented by the dissociation constant ($K_D$). Affinity can be measured by common methods known in the art, such as, for example, immunoblot, ELISA KD, KinEx A, biolayer interferometry (BLI), or surface plasmon resonance devices.

The terms "$K_D$," "$K_d$," "Kd" or "Kd value" as used interchangeably to refer to the equilibrium dissociation constant of an antibody-antigen interaction. In some embodiments, the $K_d$ of the antibody is measured by using biolayer interferometry assays using a biosensor, such as an Octet® System (Pall ForteBio LLC, Fremont, CA) according to the supplier's instructions. Briefly, biotinylated antigen is bound to the sensor tip and the association of antibody is monitored for ninety seconds and the dissociation is monitored for 600 seconds. The buffer for dilutions and binding steps is 20 mM phosphate, 150 mM NaCl, pH 7.2. A buffer only blank curve is subtracted to correct for any drift. The data are fit to a 2:1 binding model using ForteBio data analysis software to determine association rate constant ($k_{on}$), dissociation rate constant ($k_{off}$), and the $K_d$. The equilibrium dissociation constant ($K_d$) is calculated as the ratio of $k_{off}/k_{on}$. The term "$k_{on}$" refers to the rate constant for association of an antibody to an antigen and the term "$k_{off}$" refers to the rate constant for dissociation of an antibody from the antibody/antigen complex.

The term "binds" to an antigen or epitope is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA KD, KinEx A, biolayer interferometry (BLI), surface plasmon resonance devices, or etc.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51: 19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is an Octet® system (Pall ForteBio LLC). See, e.g., Abdiche et al., 2008, *Anal. Biochem.* 377: 209-277.

In some embodiments, a parvovirus antibody binds to a canine parvovirus or a feline parvovirus with a dissociation constant (Kd) of less than $5\times10^{-6}$ M, less than $1\times10^{-6}$ M, less than $5\times10^{-7}$ M, less than $1\times10^{-7}$ M, less than $5\times10^{-8}$M, less than $1\times10^{-8}$M, less than $5\times10^{-9}$M, less than $1\times10^{-9}$M, less than $5\times10^{-10}$ M, less than $1\times10^{-10}$ M, less than $5\times10^{-11}$M, less than $1\times10^{-11}$ M, less than $5\times10^{-12}$ M, or less than $1\times10^{-12}$ M, as measured by biolayer interferometry. In some embodiments, a parvovirus antibody binds to a canine parvovirus or a feline parvovirus with a Kd of between $5\times10^{-6}$ M and $1\times10^{-6}$ M, between $5\times10^{-6}$ M and $5\times10^{-7}$ M, between $5\times10^{-6}$ M and $1\times10^{-7}$ M, between $5\times10^{-6}$ M and $5\times10^{-8}$M, $5\times10^{-6}$ M and $1\times10^{-8}$ M, between $5\times10^{-6}$ M and $5\times10^{-9}$ M, between $5\times10^{-6}$ M and $1\times10^{-9}$ M, between $5\times10^{-6}$ M and $5\times10^{-10}$ M, between $5\times10^{-6}$ M and $1\times10^{-10}$ M, between $5\times10^{-6}$ M and $5\times10^{-11}$M, between $5\times10^{-6}$ M and $1\times10^{-11}$M, between $5\times10^{-6}$M and $5\times10^{-12}$M, between $5\times10^{-6}$M and $1\times10^{-12}$M, between $1\times10^{-6}$ M and $5\times10^{-7}$ M, between $1\times10^{-6}$ M and $1\times10^{-7}$ M, between $1\times10^{-6}$M and $5\times10^{-8}$M, $1\times10^{-6}$M and $1\times10^{-8}$M, between $1\times10^{-6}$ M and $5\times10^{-9}$M, between $1\times10^{-7}$ M and $1\times10^{-9}$M, between $1\times10^{-7}$ M and $5\times10^{-10}$ M, between $1\times10^{-7}$ M and $1\times10^{-10}$ M, between $1\times10^{-6}$M and $5\times10^{-11}$M, between $1\times10^{-6}$ M and $1\times10^{-11}$ M, between $1\times10^{-6}$M and $5\times10^{-12}$M, between $1\times10^{-6}$M and $1\times10^{-12}$M, between $5\times10^{-7}$M and $1\times10^{-7}$M, between $5\times10^{-7}$M and $5\times10^{-8}$M, $5\times10^{-7}$M and $1\times10^{-8}$M, between $5\times10^{-7}$M and $5\times10^{-9}$M, between $5\times10^{-7}$M and $1\times10^{-9}$M, between $5\times10^{-7}$M and $5\times10^{-10}$ M, between $5\times10^{-7}$ M and $1\times10^{-10}$ M, between $5\times10^{-7}$M and $5\times10^{-11}$M, between $5\times10^{-7}$ M and $1\times10^{-11}$ M, between $5\times10^{-7}$M and $5\times10^{-12}$M, between $5\times10^{-7}$ M and $1\times10^{-12}$M, between $1\times10^{-7}$ M and $5\times10^{-8}$M, $1\times10^{-7}$ M and $1\times10^{-8}$ M, between $1\times10^{-7}$ M and $5\times10^{-9}$ M, between $1\times10^{-7}$ M and $1\times10^{-9}$ M, between $1\times10^{-7}$M and $5\times10^{-10}$ M, between $1\times10^{-7}$M and $1\times10^{-10}$ M, between $1\times10^{-7}$M and $5\times10^{-11}$ M, between $1\times10^{-7}$ M and $1\times10^{-11}$M, between $1\times10^{-7}$M and $5\times10^{-12}$ M, between $1\times10^{-7}$ M and $1\times10^{12}$M, between $5\times10^{-8}$M and $1\times10^{-8}$M, between $5\times10^{-8}$M and $5\times10^{-9}$M, between $5\times10^{-8}$ M and $1\times10^{-9}$M, between $5\times10^{-8}$ M and $5\times10^{-10}$ M, between $5\times10^{-8}$ M and $1\times10^{-10}$ M, between $5\times10^{-8}$ M and $5\times10^{-11}$M, between $5\times10^{-8}$M and $1\times10^{-11}$ M, between $5\times10^{-8}$M and $5\times10^{-12}$M, between $5\times10^{-8}$M and $1\times10^{-12}$M, $1\times10^{-8}$M and $5\times10^{-9}$M, between $1\times10^{-8}$M and $1\times10^{-9}$M, between $1\times10^{-8}$M and $5\times10^{-10}$ M, between $1\times10^{-8}$ M and $1\times10^{-10}$ M, between $1\times10^{-8}$M and $5\times10^{-11}$M, between $1\times10^{-8}$ M and $1\times10^{-11}$ M, between $1\times10^{-8}$M and $5\times10^{-12}$M, between $1\times10^{-8}$ M and $1\times10^{-12}$M, between $5\times10^{-9}$M and $1\times10^{-9}$M, between $5\times10^{-9}$M and $5\times10^{-10}$ between $5\times10^{-9}$M and $1\times10^{-10}$ M, between $5\times10^{-9}$M and $5\times10^{-11}$ M, M, between $5\times10^{-9}$M and $1\times10^{-11}$M, between $5\times10^{-9}$ M and $5\times10^{-12}$ M, between $5\times10^{-9}$M and $1\times10^{-12}$M, between $1\times10^{-9}$M and $5\times10^{-10}$ M, between $1\times10^{-9}$M and $1\times10^{-10}$ M, between $1\times10^{-9}$M and $5\times10^{-11}$M, between $1\times10^{-9}$M and $1\times10^{-11}$M, between $1\times10^{-9}$M and $5\times10^{-12}$ M, between $1\times10^{-9}$ M and $1\times10^{-12}$ M, between $5\times10^{-10}$ M and $1\times10^{-10}$ M, between $5\times10^{-10}$ M and $5\times10^{-11}$M, between, $1\times10^{-10}$ M and $5\times10^{-11}$M, $1\times10^{-10}$ M and $1\times10^{-11}$M, between $1\times10^{-10}$ M and $5\times10^{-12}$ M, between $1\times10^{-10}$ M and $1\times10^{-12}$M, between $5\times10^{-11}$M and $1\times10^{-12}$ M, between $5\times10^{-11}$ M and $5\times10^{-12}$M, between $5\times10^{-11}$ M and $1\times10^{-12}$ M, between $1\times10^{-11}$ M and $5\times10^{-12}$ M, or between $1\times10^{-11}$ M and $1\times10^{-12}$ M, as measured by biolayer interferometry. In some embodiments, a parvovirus antibody binds to a canine parvovirus or a feline parvovirus, as determined by immunoblot analysis.

"Wild-type" refers to a non-mutated version of a polypeptide that occurs in nature, or a fragment thereof. A wild-type polypeptide may be produced recombinantly.

A "variant" means a biologically active polypeptide having at least about 50% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, deleted, at the N- or C-terminus of the polypeptide.

In some embodiments, a variant has at least 1, 2, 3, 4, or 5 amino acids substituted by a different amino acid.

In some embodiments, a variant has at least about 50% sequence identity with the reference nucleic acid molecule or polypeptide after aligning the sequences and introducing gaps, if necessary, to achieve the maximum percent sequence identity, and not considering any conservative sequence identity as part of the sequence identity. Such variants include, for instance, polypeptides wherein one or more amino acid residues are added, deleted, at the N- or C-terminus of the polypeptide. In some embodiments, a variant has at least about 50% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 95% sequence identity, at least about 97% sequence identity, at least about 98% sequence identity, or at least about 99% sequence identity with the sequence of the reference nucleic acid or polypeptide.

As used herein, "position corresponding to position n," wherein n is any number, refers to an amino acid position of a subject polypeptide that aligns with position n of a reference polypeptide after aligning the amino acid sequences of the subject and reference polypeptides and introducing gaps. Alignment for purposes of whether a position of a subject polypeptide corresponds with position n of a reference polypeptide can be achieved in various ways that are within the skill in the art, for instance, using publicly available computer software such as BLAST, BLAST-2, CLUSTAL OMEGA, ALIGN, or MEGALIGN™ (DNAS-TAR) software. Those skilled in the art can determine appropriate parameters for alignment, including any parameters needed to achieve maximal alignment over the full length of two sequences being compared. In some embodiments, the subject polypeptide and the reference polypeptide are of different lengths.

A "point mutation" is a mutation that involves a single amino acid residue. The mutation may be the loss of an amino acid, substitution of one amino acid residue for another, or the insertion of an additional amino acid residue.

An "amino acid substitution" refers to the replacement of one amino acid in a polypeptide with another amino acid. In some embodiments, an amino acid substitution is a conservative substitution. Nonlimiting exemplary conservative amino acid substitutions are shown in Table 2. Amino acid substitutions may be introduced into a molecule of interest and the products screened for a desired activity, for example, retained/improved antigen binding, decreased immunogenicity, or improved ADCC or CDC or enhanced pharmacokinetics.

TABLE 2

| Original Residue | Exemplary Substitutions |
|---|---|
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes with another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters or enhancers) that regulate the expression of the polypeptide of interest, or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), 293 cells, and CHO cells, and their derivatives, such as 293-6E, DG44, CHO-S, and CHO-K cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) encoding an amino acid sequence(s) provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated." In some embodiments, the parvovirus antibody is purified using chromatography, such as size exclusion chromatography, ion exchange chromatography, protein A column chromatography, hydrophobic interaction chromatography, and CHT chromatography.

To "reduce" or "inhibit" means to decrease, reduce, or arrest an activity, function, or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy or non-diseased sample. In some examples, a reference is obtained from a non-diseased or non-treated sample of a companion animal. In some examples, a reference is obtained from one or more healthy animals of a particular species, which are not the animal being tested or treated.

The term "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 15% 20%, 25%, 30%, 35%, 40%, 45%, 50%, 60%, 70%, 80%, 90%, or 100% compared to the reference value.

In some embodiments, an parvovirus antibody may reduce parvovirus titers in a canine or a feline by at least 10%, at least 15%, at least 20%, at least 25%, at least 30%, at least 35%, at least 40%, at least 45%, at least 50%, at least 60%, at least 70%, at least 80%, at least 90%, or 100% compared to parvovirus titers in the absence of the antibody, as measured by a Hemagglutination Inhibition (HI) assay or Virus Neutralization (VN) assay. In some embodiments, the reduction in parvovirus titer is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Exemplary Pharmaceutical Compositions

The terms "pharmaceutical formulation" and "pharmaceutical composition" refer to a preparation which is in such form as to permit the biological activity of the active ingredient(s) to be effective, and which contains no additional components that are unacceptably toxic to a subject to which the formulation would be administered.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. Examples of pharmaceutically acceptable carriers include alumina; aluminum stearate; lecithin; serum proteins, such as human serum albumin, canine or other animal albumin; buffers such as phosphate, citrate, tromethamine or HEPES buffers; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts, colloidal silica, or magnesium trisilicate; polyvinyl pyrrolidone, cellulose-based substances; polyethylene glycol; sucrose; mannitol; or amino acids including, but not limited to, arginine.

The pharmaceutical composition can be stored in lyophilized form. Thus, in some embodiments, the preparation process includes a lyophilization step. The lyophilized composition may then be reformulated, typically as an aqueous composition suitable for parenteral administration, prior to administration to the dog, cat, or horse. In other embodiments, particularly where the antibody is highly stable to thermal and oxidative denaturation, the pharmaceutical composition can be stored as a liquid, i.e., as an aqueous composition, which may be administered directly, or with appropriate dilution, to the dog, cat, or horse. A lyophilized composition can be reconstituted with sterile Water for Injection (WFI). Anti-bacterial agents (e.g., bacteriostatic reagents, such benzyl alcohol, may be included. Thus, the invention provides pharmaceutical compositions in solid or liquid form.

The pH of the pharmaceutical compositions may be in the range of from about pH 5 to about pH 8, when administered. The compositions of the invention are sterile if they are to be used for therapeutic purposes. Sterility can be achieved by any of several means known in the art, including by filtration through sterile filtration membranes (e.g., 0.2 micron membranes). Sterility may be maintained with or without anti-bacterial agents.

In some embodiments, the pharmaceutically acceptable carrier or the pharmaceutical composition has a pH of from 5.0 to 6.2, from 5.0 to 6.0, or from 5.3 to 5.7. In some embodiments, the pharmaceutical carrier is phosphate buffered saline, pH 7.2. In some embodiments, the pharmaceutical carrier is 50 mM NaCitrate pH 7, 150 mM NaCl.

In some embodiments, the pharmaceutically acceptable carrier or a pharmaceutical composition comprises an anti-bacterial agent.

Exemplary Uses of Antibodies and Pharmaceutical Compositions

The antibodies or pharmaceutical compositions comprising the antibodies of the invention may be useful for providing passive immunity against infection with parvovirus and/or treating a parvoviral infection. As used herein, a "parvoviral infection" means a condition associated with, caused by, or characterized by, a parvoviral infection. Such conditions include, but are not limited to, infections confirmed by cage-side ELISA tests, hemagglutination assay (HA), histopathology, virus isolation or virus titers, or PCR. Infections with parvovirus often include fever, vomiting, diarrhea, lymphopenia, dehydration, and/or secondary septicemia.

As used herein, "treatment" is an approach for obtaining beneficial or desired clinical results. "Treatment" as used herein, covers any administration or application of a therapeutic for disease in a subject, such as a mammal, including a human and a companion animal (e.g., a canine or feline). For purposes of this disclosure, beneficial or desired clinical results include, but are not limited to, any one or more of: alleviation of one or more symptoms, prevention of mortality, diminishment of extent and severity of disease, preventing or delaying spread of disease, eliminating or shorting duration of viral shedding, preventing or delaying recurrence of disease, preventing or decreasing viral cytopathic effects, delay or slowing of disease progression, amelioration of the disease state, inhibiting the disease or progression of the disease, resolution of clinical signs of disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

In some embodiments, a parvovirus antibody or pharmaceutical compositions comprising it can be utilized in accordance with the methods herein to provide passive immunity against infection parvovirus and/or treat parvoviral infections. In some embodiments, a parvovirus antibody or pharmaceutical compositions is administered to subject, such as a companion animal (e.g., a canine or a feline) or a human to provide passive immunity against infection with parvovirus and/or treat an a parvoviral infection.

A "therapeutically effective amount" of a substance/molecule, agonist or antagonist may vary according to factors such as the type of disease to be treated, the disease state, the immune status of the individual subject, the virulent viral load encountered, the severity and extent of viremia, the severity and course of the disease, the type of therapeutic purpose, any previous therapy, the clinical history, the response to prior treatment, the maternally-derived antibody passive transfer status, the previous immunization status of the individual animal, the discretion of the attending veterinarian, age, sex, and weight of the subject, and the ability of the substance/molecule, agonist or antagonist to elicit a desired response in the subject. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic or prophylactic result.

In some embodiments, a parvovirus antibody or pharmaceutical composition comprising a parvovirus antibody is administered parenterally, by subcutaneous administration, intravenous infusion, or intramuscular injection. In some embodiments, a parvovirus antibody or pharmaceutical composition comprising a parvovirus antibody is administered as a single dose or multiple dose bolus injection. In some embodiments, a parvovirus antibody or pharmaceutical composition comprising a parvovirus antibody is administered by an intramuscular, an intravenous, an intraperitoneal, an intracerebrospinal, a subcutaneous, an intra-arterial, an intrasynovial, an intrathecal, or an inhalation route.

Parvovirus antibodies described herein may be administered in an amount in the range of 0.01 mg/kg body weight to 100 mg/kg body weight per dose. In some embodiments, parvovirus antibodies may be administered in an amount in the range of 0.5 mg/kg body weight to 50 mg/kg body weight per dose. In some embodiments, parvovirus antibodies may be administered in an amount in the range of 0.1 mg/kg body weight to 10 mg/kg body weight per dose. In some embodiments, parvovirus antibodies may be administered in an amount in the range of 0.1 mg/kg body weight to 100 mg/kg body weight per dose. In some embodiments, parvovirus antibodies may be administered in an amount in the range of 1 mg/kg body weight to 10 mg/kg body weight per dose. In some embodiments, parvovirus antibodies may be administered in an amount in the range of 0.5 mg/kg body weight to 100 mg/kg body, in the range of 1 mg/kg body weight to 100 mg/kg body weight, in the range of 5 mg/kg body weight to 100 mg/kg body weight, in the range of 10 mg/kg body weight to 100 mg/kg body weight, in the range of 20 mg/kg body weight to 100 mg/kg body weight, in the range of 50 mg/kg body weight to 100 mg/kg body weight, in the range of 1 mg/kg body weight to 10 mg/kg body weight, in the range of 5 mg/kg body weight to 10 mg/kg body weight, in the range of 0.5 mg/kg body weight to 10 mg/kg body weight, in the range of 0.01 mg/kg body weight to 0.5 mg/kg body weight, in the range of 0.01 mg/kg body weight to 0.1 mg/kg body weight, or in the range of 5 mg/kg body weight to 50 mg/kg body weight. In some embodiments, parvovirus antibodies may be administered in an amount of 0.5 mg/kg body weight.

A parvovirus antibody or a pharmaceutical composition comprising a parvovirus antibody can be administered to a subject, such as a human or companion animal (e.g., a canine or a feline) as a single dose, at one time or over a series of treatments. For example, a parvovirus antibody or a pharmaceutical composition comprising a parvovirus antibody may be administered at least once, more than once, at least twice, at least three times, at least four times, or at least five times.

In some embodiments, the dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

In some embodiments, the dose is administered to a subject, such as a human or companion animal (e.g., a canine or a feline) less than 1 week of age, less than 2 weeks of age, less than 3 weeks of age, less than 4 weeks of age, less than 5 weeks of age, less than 6 weeks of age, less than 6 weeks of age, less than 7 weeks of age, less than 8 weeks of age, less than 9 weeks of age, less than 10 weeks of age, less than 11 weeks of age, less than 12 weeks of age, less than 6 months of age, between 0 and 12 weeks of age, between 0 and 10 weeks of age, between 0 and 8 weeks of age, between 0 and 6 weeks of age, between 0 and 4 weeks of age, between 0 and 2 weeks of age, between 4 and 12 weeks of age, between 6 and 12 weeks of age, between 10 and 12 weeks of age, between 4 weeks and 6 months of age, between 2 months and 6 months of age, between 4 months and 6 months of age, between 6 months and 1 year of age, greater than 13 weeks of age, or greater than 1 year of age.

It may be advantageous to deliver the parvovirus antibody or a nucleic acid encoding the parvovirus antibody to an infant subject prenatally and/or postnatally to provide passive immunity against parvovirus infection. In some embodiments, the parvovirus antibody is administered to a pregnant or nursing maternal subject, such as a human or companion animal (e.g., a canine or a feline). In some embodiments, the parvovirus antibody is administered to the placenta of a pregnant subject.

In some embodiments, a method of providing passive immunity in an infant subject against infection with a canine or feline parvovirus comprises administering to a pregnant or nursing maternal subject a therapeutically effective amount of a monoclonal antibody that binds to the canine or feline parvovirus. In some embodiments the parvovirus antibody is administered to the placenta of a pregnant subject. In some embodiments, the parvovirus antibody is administered to a nursing subject.

Provided herein are methods of using the parvovirus antibodies, polypeptides and polynucleotides for detection, diagnosis and monitoring of a parvoviral infection. Provided herein are methods of determining whether a subject will respond to parvovirus antibody therapy. In some embodiments, the method comprises virus serum neutralization. In some embodiments, the method comprises detecting whether the subject has cells that express parvovirus using a parvovirus antibody. In some embodiments, the method of detection comprises contacting the sample with an antibody, polypeptide, or polynucleotide and determining whether the level of binding differs from that of a reference or comparison sample (such as a control). In some embodiments, the method may be useful to determine whether the antibodies or polypeptides described herein are an appropriate treatment for the subject.

In some embodiments, the sample is a biological sample. The term "biological sample" means a quantity of a substance from a living thing or formerly living thing. In some embodiments, the biological sample is a swab containing cellular debris, cell or cell/tissue lysate. In some embodiments, the biological sample includes, but is not limited to, blood, (for example, whole blood), plasma, serum, urine, synovial fluid, lymphatic tissue and epithelial cells.

In some embodiments, the cells or cell/tissue lysate are contacted with a parvovirus antibody and the binding between the antibody and the cell is determined. When the test cells show binding activity as compared to a reference cell of the same tissue type, it may indicate that the subject would benefit from treatment with a parvovirus antibody. In some embodiments, the test cells are from tissue of a subject, such as a human or companion animal (e.g., a canine or a feline).

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (for example $^{125}I$, $^{131}I$, $^{35}S$, $^{3}H$, or $^{32}P$), enzymes (for example, alkaline phosphatase, horseradish peroxidase, luciferase, or b-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art. In some embodiments, the parvovirus antibodies need not be labeled, and the presence thereof can be detected using a second labeled antibody which binds to the first parvovirus antibody. In some embodiments, the parvovirus antibody can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987). The parvovirus antibodies and polypeptides can also be used for in vivo diagnostic assays, such as in vivo imaging. Generally, the antibody or the polypeptide is labeled with a radionuclide (such as $^{111}In$, $^{99}Tc$, $^{14}C$, $^{131}I$, $^{125}I$, $^{3}H$, or any other radionuclide label, including those outlined herein) so that the cells or tissue of interest can be localized using immunoscintiography. The antibody may also be used as staining reagent in pathology using techniques well known in the art.

In some embodiments, a first antibody is used for a diagnostic and a second antibody is used as a therapeutic. In some embodiments, the first and second antibodies are different. In some embodiments, the first and second antibodies can both bind to the antigen at the same time, by binding to separate epitopes.

The following examples illustrate particular aspects of the disclosure and are not intended in any way to limit the disclosure.

EXAMPLES

Example 1

Preparation of Chimeric Canine Antibodies Mab A and Mab B

Structural analysis of canine parvovirus and feline parvovirus complexed with antibody fragments from eight different neutralizing monoclonal antibodies were reported in Hafenstein S., et al, J Virol. 2009 June, 83(11):5556-66. Incomplete amino acid sequence information was provided for rat Mab E and Mab F Fab fragments, which exhibited canine parvovirus neutralization in an in vitro assay. The incomplete amino acid sequences for the variable heavy chain and variable light chain of Mab E are SEQ ID NOs. 81 and 82, respectively. The incomplete amino acid sequences for the variable heavy chain and variable light chain of Mab F are SEQ ID NOs. 83 and 84, respectively.

Three-dimensional protein structure analysis was performed to construct a redesigned first framework region for both heavy and light chains of Mab E and Mab F. The amino acid sequences of the heavy and light chain of redesigned monoclonal antibodies, designated Mab A and Mab B, are SEQ ID NO: 20 (Mab A heavy chain), SEQ ID NO: 22 (Mab A light chain), SEQ ID NO: 62 (Mab B heavy chain), and SEQ ID NO: 64 (Mab B light chain).

DNA sequences encoding a chimeric antibody were designed for fusions of Mab A VH (SEQ ID NO: 20) and Mab B VH (SEQ ID NO: 62) to canine constant IgG-B heavy chain and Mab A VL (SEQ ID NO: 22) and Mab B LC (SEQ ID NO: 64) to canine constant κ light chain resulting in SEQ ID NO: 23 (Chimeric A HC IgG-B), SEQ ID NO: 66 (Chimeric B HC IgG-B), SEQ ID NO: 25 (Chimeric A LC κ), and SEQ ID NO: 68 (Chimeric B LC κ). The heavy chain and light chain nucleotide sequences were synthesized chemically and inserted into an expression vector suitable for transfection into a mammalian host cell. Following transfection of heavy and light chain vector pairs into cells and culture, antibodies were affinity purified from the culture media using CaptivA® Protein A Affinity Resin (Repligen). The purified Chimeric Canine Mab A and Mab B antibodies were confirmed by SDS-PAGE analysis (data not shown).

Chimeric antibodies may also be designed and prepared based on fusions of Mab A VH (SEQ ID NO: 20) and Mab B VH (SEQ ID NO: 62) to canine constant IgG-A, IgG-C, and IgG-D heavy chains.

Example 2

Chimeric Canine Antibodies Mab A and Mab B Activity

Both purified Chimeric Canine Mab A and Mab B (formulated in PBS, pH 7.2 at 200 μg/mL) were used for assessing anti-canine parvovirus activity using a hemagglutination inhibition (HI) assay. The assay was performed at Companion Animal Vaccine and Immuno Diagnostic Service Laboratory, University of Wisconsin, essentially as described by Carmichael, et al., Am J of Vet Res. 1980 May, 41 (5):784-91. Serial dilutions of samples of Chimeric Canine Mab A and Chimeric Canine Mab B incubated with CPV were prepared. Porcine red blood cells were then added. Canine parvovirus induces porcine red blood cells to agglutinate. Both Chimeric Canine Mab A and Chimeric Canine Mab B prevented agglutination. Both antibodies resulted in a CPV-2b HI of 40960, while irrelevant canine IgG produced HI of <20. Most vaccinated dogs are understood to have antibody HI around 1280.

Furthermore, the activity of the antibodies to prevent live CPV from infecting and destroying cells was analyzed using Virus Serum Neutralization assay.

Example 3

Variant VH and VL Sequences for Enhanced Expression of Chimeric Canine Mab A and Mab B Chimeric Canine Mab A and Chimeric Canine Mab B consistently expressed poorly in transient CHOS or stable CHOK1 cells. To enhance expression levels, three-dimensional protein structure analysis was performed to identify VH and VL amino acid residues suitable for modification. Multiple constructs with various mutations in VH and VL were generated. The expression level of antibodies having combinations of canine IgG-B with VH and VL variants were tested.

Enhanced expression variants were analyzed for their specific activity by canine parvovirus HI assay. In these experiments, each of the antibody variants tested was formulated in PBS, pH 7.2 at 200 μg/mL. Both Chimeric Canine Mab A (SEQ ID NOs: 23 and 25) and Chimeric Canine Mab B (SEQ ID NOs: 66 and 68) demonstrated a CPV-2b HI of 10240. Enhanced expression variants, Chimeric Canine Mab A v2 (SEQ ID NOs: 24 and 25) and Chimeric Canine Mab B v2 (SEQ ID NOs: 67 and 69), maintained the same HI value of 10240, while other variants displayed lower specific activity.

Example 4

Parvovirus Infection Assay Activity (SVN)

To determine the ability of Chimeric Canine Mab A v2 (SEQ ID NOs: 24 and 25) and Chimeric Canine Mab B v2 (SEQ ID NOs: 67 and 69) to prevent live parvovirus from infecting and destroying cells, a serum virus neutralization (SVN) assay was performed. In this assay, Madin Darby Canine Kidney (MDCK) cells were grown. Serial dilutions of antibody were mixed with a fixed titer of parvovirus. The mixture was then incubated with the cells. After incubation, the cells were examined by microscopy to identify the viral cytopathic effect (CPE). The readout is the final dilution of the antibody sample where it reached limits in preventing parvovirus from causing the cytopathic effect.

Both Chimeric Canine Mab A v2 (1) kept at 4° C. and (2) subjected to 7 freeze-thaw cycles at 200 ug/mL had the same activity: SVN for CPV-2b 32000 and SVN for CPV2c 8000.

Example 5

Stability of Chimeric Canine Mab A v2 and Mab B v2

Stability of Chimeric Canine Mab A v2 (SEQ ID NOs: 24 and 25) at 25 mg/mL and Chimeric Canine Mab B v2 (SEQ ID NOs: 67 and 69) at 20.5 mg/mL was tested. Chimeric Canine Mab A v2 and Chimeric Canine Mab B v2 have similar specific activity by HI assay at a concentration of about 25 mg/mL and about 20.5 mg/mL, respectively.

Both Chimeric Canine Mab A v2 and Chimeric Canine Mab B v2 produced and purified from CHOK1 stable pool can be readily concentrated to 25 mg/mL in PBS, pH7.2, suggesting that both antibodies have no solubility concerns.

Chimeric Canine Mab A v2 and Chimeric Canine Mab B v2 are monomeric (>99%) at neutral pH and after storage for 10 hours at pH 4.1, as assessed by size-exclusion high performance liquid chromatography (HPLC). In this analysis, monomer and aggregates of antibodies were separated by SEC-HPLC, using Agilent 1100 system, Shodex KW803 column (8 mm×300 mm) with a KW-G guard column, and mobile phase buffer of 2×PBS pH7.2 (270 mM NaCl, 5.4 mM KCl, 8.6 mM Na2HPO4, 2.8 mM KPO4) at α constant flow rate of 0.5 mL/minute. The column was calibrated using Bio Rad markers (Catalog No. 151-1901) composed of Thyroglobulin, γ-globulin, Ovalbumin, Myoglobin and Vitamin B12.

Chimeric Canine Mab A v2 real-time stability in (1) PBS, pH 7.2 at 25 mg/mL and (2) 50 mM NaCitrate pH 7, 150 mM NaCl at 25 mg/mL at various temperatures were evaluated. The HPLC-SEC results at ten months are summarized in Table 3.

TABLE 3

| Buffer | Temperature | % HMW | Chimeric Canine Mab A v2 (% monomer) |
|---|---|---|---|
| PBS pH 7.2 | −80° C. (control) | <LOQ | 100 |
| | −20° C. | <LOQ | 100 |
| | 4° C. | <LOQ | 100 |
| | 25° C. | 2.1% | 97.9 |
| 50 mM NaCitrate pH 7, 150 mM NaCl | −80° C. (control) | <LOQ | 100 |
| | −20° C. | <LOQ | 100 |

Stability was also tested by subjecting the antibodies to three freeze-thaw cycles with freezing at −70° C. and thawing at room temperature. No loss of activity was observed for either antibody in terms of both CPV-2b HI and CPV-2c HI value.

Stability was further tested by subjecting the antibodies to seven freeze-thaw cycles with freezing at −20° C. and thawing at room temperature. Both antibodies maintained full activity as measured by HI assay.

Thermostability of the two antibodies in different formulations and across a range of pH was analyzed using differential scanning fluorescence (DSF). The melting temperature (Tm) of each antibody at the different conditions were measured. Buffer and 12 μg of antibody were mixed together with 1× Protein thermal shift dye (Applied Biosystem, Catalog No. 4461146). A melting curve was performed with StepOne Real Time PCR System (Applied Biosystem, Catalog No. 4376357). The temperature was increased from 25° C. to 99° C. with a ramp rate of 1% according to the manufacturer's instructions. The data was analyzed by Protein Thermal Shift™ Software v1.0 (Applied Biosystem, Catalog No. 4466038) to determine the Tm, which was calculated as the highest value derived from taking the first derivative of the protein melting curve. For each of the formulations tested, including PBS pH7.2, Chimeric Canine Mab A v2 was significantly more stable than Chimeric Canine Mab B v2.

Example 6

VLP Bindings of Chimeric Canine Antibodies Mab A v2 and Mab B v2

Apparent affinity of Chimeric Canine Mab A v2 (SEQ ID NOs: 24 and 25) and Chimeric Canine Mab B v2 (SEQ ID NOs: 67 and 69) with parvovirus VLP was measured. First, biotinylated Chimeric Canine Mab A v2 and Chimeric Canine Mab B v2 were bound to streptavidin sensor tips. Then, binding of recombinant canine parvovirus CPV2b capsid (Advanced ImmunoChemical Inc Cat #8-CPV) to the Mab-bound sensor tip was assessed.

Chimeric Canine Mab A v2 and Chimeric Canine Mab B v2 antibodies each exhibited affinity to canine CPV 2b VLP with kinetics potentially sufficient for therapeutic activity. The binding analysis was performed using an Octet Biosensor as follows. Briefly, Chimeric Canine Mab A v2 (SEQ ID NOs: 24 and 25) and Chimeric Canine Mab B v2 (SEQ ID NOs: 67 and 69) was biotinylated through amine chemistry. The free unreacted biotin was removed by extensive dialysis. Biotinylated Chimeric Canine Mab A v2 and Chimeric Canine Mab B v2 was captured on streptavidin sensor tips. The association of either Mab A v2 or Mab B v2 and canine CPV 2b VLP (40 μg/mL) was monitored for 300 seconds. Dissociation was monitored for 300 seconds. A biotinylated irrelevant canine IgG-B was used as negative control. The data were fit to a 1:1 binding model using ForteBio™ data analysis software to determine the kon, koff, and the Kd. The buffer for dilutions and all binding steps was 20 mM phosphate, 150 mM NaCl, pH 7.2. The Kd of Chimeric Canine Mab A v2 and VLP2b was $9.78\times10^{-11}$ M and of Chimeric Canine Mab B v2 and VLP2b was $9.38\times10^{-12}$ M (See FIG. 2).

Example 7

Caninization of Mab A v2 and Mab B v2

To reduce potential immunogenicity, particularly where repeated administration of antibodies A or B are needed, VH and VL from Mab A v2 and B v2 were subjected to caninization. A number of caninized VH and VL were designed, expressed, and purified. Good expressors were selected for specific activity using CPV2b HI assay. Caninized A HC v3 IgG-B (SEQ ID NO: 37) plus Caninized A LC κ (SEQ ID NO: 39) and Caninized A HC v4 IgG-B (SEQ ID NO: 38) plus Caninized A LC κ (SEQ ID NO: 39) maintained full activity compared to Chimeric A HC IgG-B (SEQ ID NO: 23) plus Chimeric A LC κ (SEQ ID NO: 25) and compared to Chimeric A HC v2 IgG-B (SEQ ID NO: 24) plus Chimeric A LC κ (SEQ ID NO: 25). Caninized B HC v3 IgG-B (SEQ ID NO: 79) plus Caninized B LC v3 κ (SEQ ID NO: 80) maintained full activity compared to Chimeric B HC IgG-B (SEQ ID NO: 66) plus Chimeric B LC κ (SEQ ID NO: 68) and compared to Chimeric B HC v2 IgG-B (SEQ ID NO: 67) plus Chimeric B LC v2 κ (SEQ ID NO: 69).

Example 8

Feline Chimeric Mab A and Mab B

Chimeric Canine Mab A v2 (SEQ ID NOs: 24 and 25) and Chimeric Canine Mab B v2 (SEQ ID NOs: 67 and 69) showed activity in a feline parvovirus HI assay. Chimeric Canine Mab A v2 at 200 m/mL exhibited a feline parvovirus HI of 262144, while Chimeric Canine Mab B v2 at 200 ug/ml exhibited a feline parvovirus HI of 131072.

Thus, Mab A and Mab B may be used in feline Parvovirus (panleukopenia virus) prevention or treatment. Furthermore, chimeric feline Mab A variable heavy chain and feline IgG-1 was designed to pair with chimeric feline Mab A variable light chain and feline kappa (SEQ ID NOs: 31 and 32). To remove potential heterogeneity, a mutation that removes the glycosylation site can be introduced to make chimeric feline Mab A-IgG1 paired with an aglycosylated kappa (e.g., SEQ ID NOs: 31 and 33).

Further, chimeric feline Mab B variable heavy chain and feline IgG-1 was designed to pair with chimeric feline Mab B variable light chain and feline kappa (SEQ ID NOs: 74 and 75). A mutation that removes the glycosylation site can be introduced to make chimeric feline Mab A-IgG1 paired with an aglycosylated kappa (e.g., SEQ ID NOs: 74 and 76).

Example 9

Safety and Pharmacodynamics in Puppies

An in vivo study was performed using Chimeric Canine Mab A (SEQ ID NOs: 23 and 25) and Chimeric Canine Mab B (SEQ ID NOs: 66 and 68) monoclonal antibodies. The objectives of this study were to evaluate safety, effect of Chimeric Canine Mab A and Chimeric Canine Mab B on Canine Parvovirus-2 (CPV-2) titers, virus neutralization, and response to a monovalent modified live vaccine after treatment with the two antibodies in purpose-bred, unvaccinated, healthy puppies. See study design summary in Table 4, below.

TABLE 4

| | |
|---|---|
| Identity | Anti-Canine Parvovirus Neutralizing Antibodies Chimeric Canine Mab A (SEQ ID NOs: 23 and 25) and Chimeric Canine Mab B (SEQ ID NOs: 66 and 68). |
| Protocol Number | KB-030-PK-301 |
| Protocol Title | Pilot Pharmacodynamic and Safety Study of Mab A and Mab B in Purpose Bred Puppies |
| Materials and Methods | The study was open label<br>Non-GLP<br>Single-dose laboratory PD and safety study in unvaccinated, CPV-2 titer negative, healthy beagles<br>Puppies were randomized to one of two equal treatment groups (3 to Mab A:3 to Mab B)<br>Allocation occurred using a randomization list supplied by Sponsor<br>Concomitant medications were given for coccidia and helminth prophylaxis during the acclimation phase. |
| Study Population | 6 healthy female beagle puppies<br>10-12 weeks of age<br>Weight at least 1.5 kg<br>Sourced from Ridglan Farms, Wisconsin |
| Study Dates | Study Initiation/Acclimation: 21 Jan. 2019<br>TA Administered: 28 Jan. 2019<br>Study End: 9 May 2019 |

After randomization when puppies were allocated into two groups (3 Mab A (Dog IDs BDW-8, DEW-8, and DFW-8):3 Mab B (Dog IDs CTW-8, CWW-8, and DHW-8). Puppies received the respective antibody in a single intravenous dose (5 mg/kg) via a clipped and prepared cephalic vein on study Day 0. A monovalent CPV vaccine, Nobivac 1-Pv (Merck Animal Health, Kenilworth, NJ) was initially administered to puppies at titers of 80 or lower. A second dose was administered at 21 days after the first dose. A third dose was administered if the puppy had not seroconverted at about 21 days after the second dose.

Puppies were monitored using Hemagglutination Inhibition (HI) and Virus Neutralization (VN) for a total of 100 days. HI quantifies the amount of antibody in a serum sample and VN is utilized to determine the ability of an antibody to prevent live virus from infecting and destroying cells. The puppies were also followed to determine if they seroconverted following CPV vaccination.

All puppies were validated to have HI titers of <20 on Day 0 before intravenous administration of Mab A or B antibodies. Day 1 HI titers after administration of Mab A or B were between 2560 and 5120. Titers were monitored for 100 days to document the degradation of the antibodies and evaluate serum half-life.

Figure 3A:
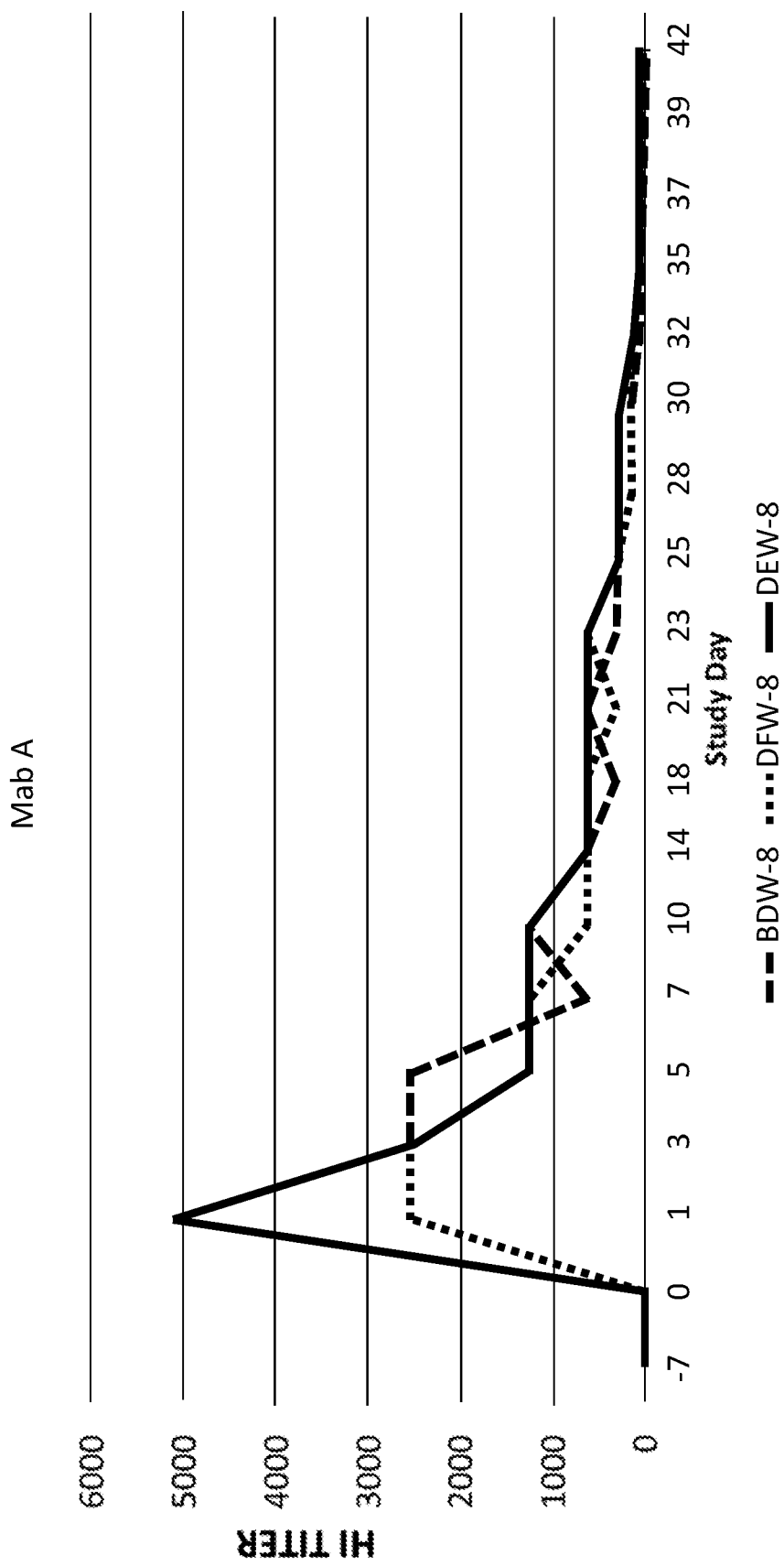
FIG. 3A shows the HI assay titers for the Mab A group.
Figure 3B:
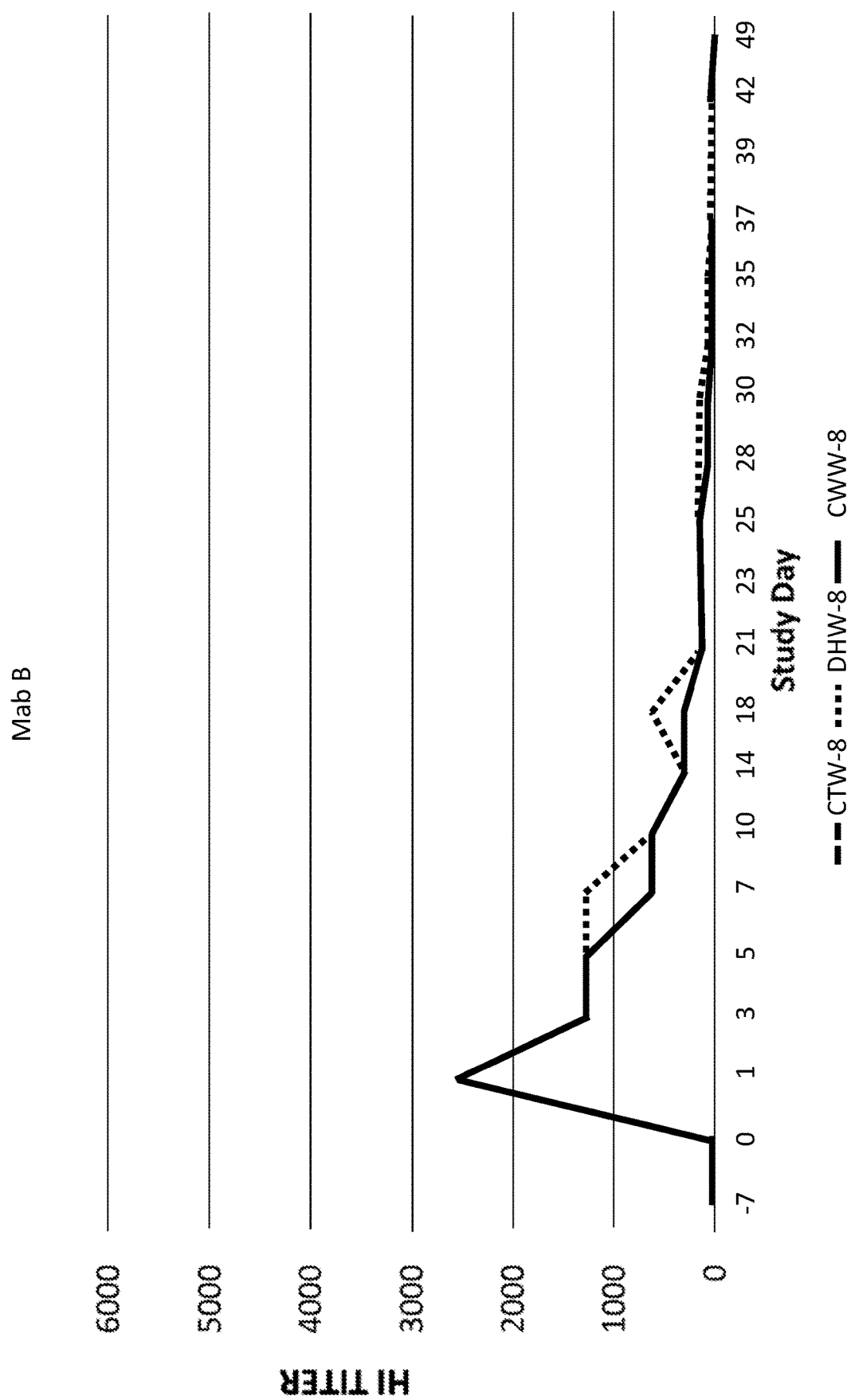
FIG. 3B shows the HI assay titers for the Mab B group.
Figure 3C:
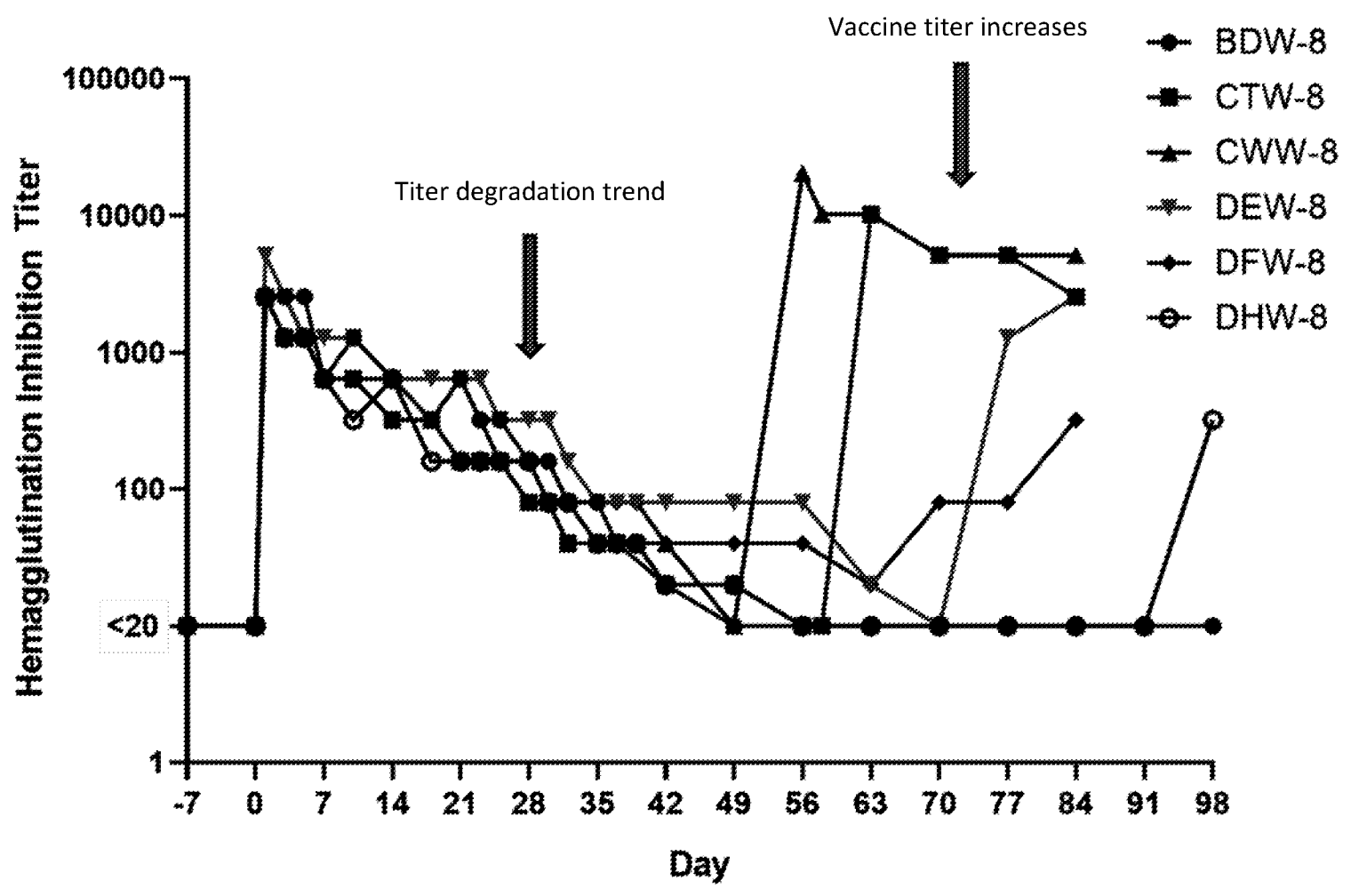

On Day 37 when titers from individual puppies began to fall to 1:40, vaccinations began to be administered to assess neutralization of vaccinal CPV-2. Mab A or B antibodies were documented to block immunization at varying levels in the puppies. Puppies were given subsequent doses of vaccination on schedule and response was verified. Vaccinal seroconversion ultimately occurred in 5 of the 6 puppies. The HI assay titers for both groups of animals are reflected in the Table 5, below and in FIG. 3A (Mab A group), FIG. 3B (Mab B group), and FIG. 3C (both groups combined).

Figure 4A:
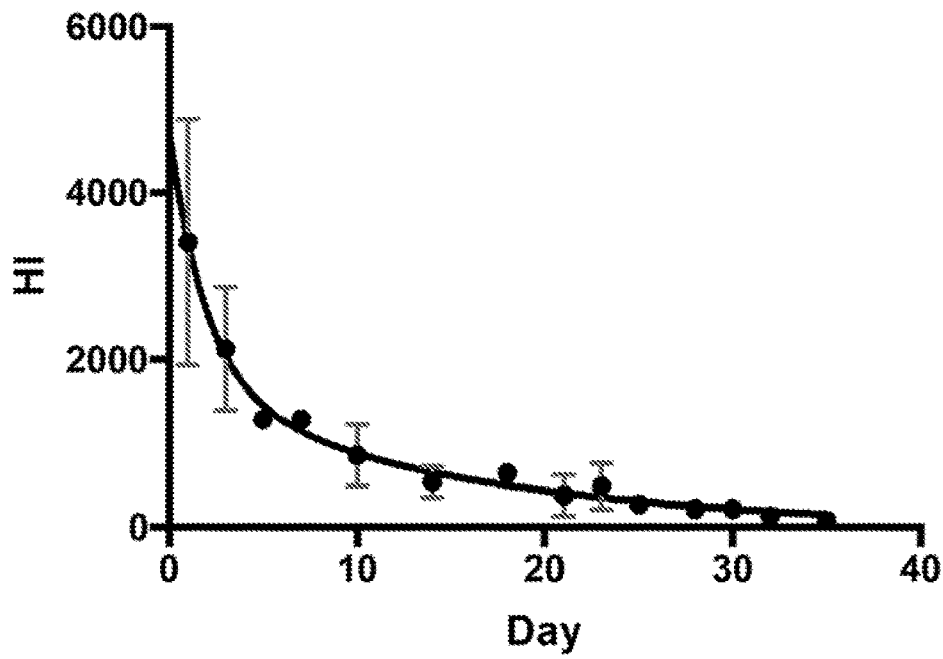
FIG. 4A shows two phase decay kinetics of Mab A v2.
Figure 4B:
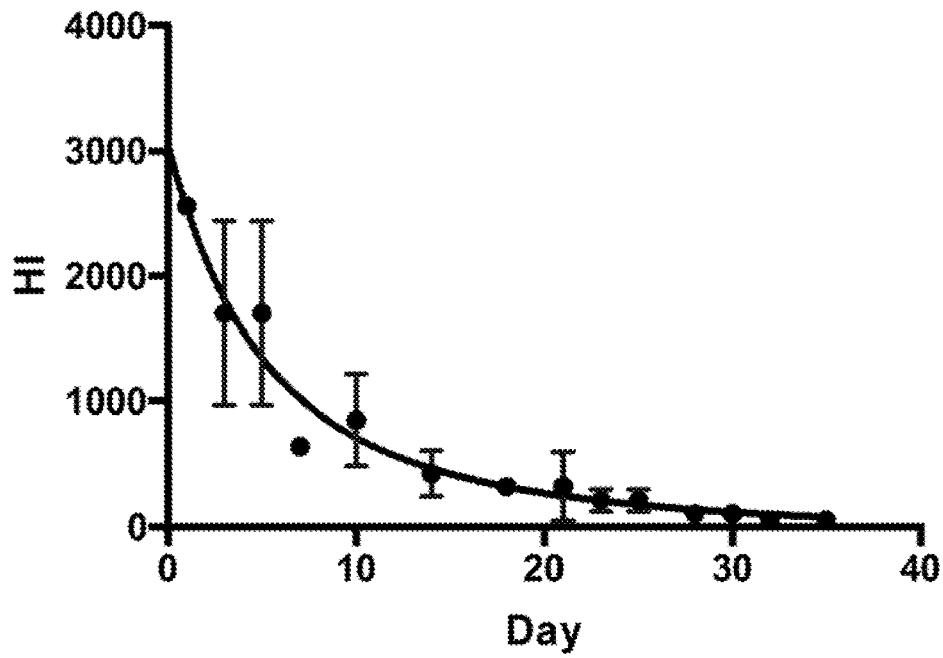
FIG. 4B shows two phase decay kinetics of Mab B v2.

Two phase decay kinetics was used to obtain the fast distribution and slow phase decay using HI as function of time. Half-life of Chimeric Canine Mab A was 10.1 days (FIG. 4A) while half-life of Chimeric Canine Mab B was 8.6 days (FIG. 4B). Serum VN assays mirrored the HI titers (See Table 6, below). The half-life roughly matches maternally-derived antibody. (Carmichael, L E, Joubert, J C and Pollock, RVH; "A Modified Live Canine Parvovirus Vaccine. II. Immune Response;" Cornell Vet, Volume 73, Pages 13-29; 1983).

This initial pharmacodynamic study demonstrates that intravenously administered Chimeric Canine Mab A (SEQ ID NOs: 23 and 25) and Chimeric Canine Mab B (SEQ ID NOs: 66 and 68) resulted in initial antibody titers between 2560 and 5120 within 24 hours post-administration. Additionally, VN follows HI titers very closely. The approximate half-life of the antibodies is between 7 and 10 days. The duration of immunity (i.e., the duration in which the HI titer was maintained at 80 or higher), ranged from 30-42 days after one dose of Chimeric Canine Mab A or Chimeric Canine Mab B. Interference with vaccination is likely until the antibody degrades sufficiently to no longer neutralize vaccinal CPV-2. Both Chimeric Canine Mab A and Chimeric Canine Mab B resulted in high titers, were well-tolerated and no adverse events or injection site reactions were reported.

The initial CPV vaccination did not result in seroconversion in 5 out of 6 puppies, potentially due to residual Chimeric Canine Mab A or B antibodies neutralizing the vaccine. Blocking of vaccinal virus replication by both Canine Mab A or Chimeric Canine Mab B was the first in vivo correlation to the in vitro neutralization data. Subsequently, three puppies seroconverted after the second and one after the third vaccination.

Regarding puppy CWW-8, seroconversion on Day 56 did not correlate with the timeframe of vaccination administered on Day 37. It is suspected that vaccinal virus shedding from other puppies in the study exposed CWW-8 and produced the seroconversion once the titers were <20.

TABLE 5

| Animal ID | Day -7 | Day 0 | Day 1 | Day 3 | Day 5 | Day 7 | Day 10 | Day 14 | Day 18 | Day 21 | Day 23 | Day 25 | Day 28 | Day 30 | Day 32 |
|---|---|---|---|---|---|---|---|---|---|---|---|---|---|---|---|
| | | | | | Hemagglutination Inhibition Assay/Parvovirus titer | | | | | | | | | | |
| BDW-8 | <20 | <20 | 2560 | 2560 | 2560 | 640 | 1280 | 640 | 320 | 640 | 320 | 320 | 160 | 160 | 80 |
| DEW-8 | <20 | <20 | 5120 | 2560 | 1280 | 1280 | 1280 | 640 | 640 | 640 | 640 | 320 | 320 | 320 | 160 |
| DFW-8 | <20 | <20 | 2560 | 2560 | 1280 | 1280 | 640 | 640 | 640 | 320 | 640 | 320 | 160 | 160 | 160 |
| CTW-8 | <20 | <20 | 2560 | 1280 | 1280 | 640 | 640 | 320 | 320 | 160 | 160 | 160 | 80 | 80 | 40 |
| CWW-8 | <20 | <20 | 2560 | 1280 | 1280 | 640 | 640 | 320 | 320 | 160 | 160 | 160 | 80 | 80 | 40 |
| DHW-8 | <20 | <20 | 2560 | 1280 | 1280 | 1280 | 640 | 320 | 640 | 160 | 160 | 160 | 160 | 160 | 80 |

| Animal ID | Day 35 | Day 37 | Day 39 | Day 42 | Day 49 | Day 56 | Day 58 | Day 63 | Day 70 | Day 77 | Day 84 | Day 87 | Day 91 | Day 98 |
|---|---|---|---|---|---|---|---|---|---|---|---|---|---|---|
| | Hemagglutination Inhibition Assay/Parvovirus titer | | | | | | | | | | | | | |
| BDW-8 | 80 | 40 | 40 | 20[1] | <20 | <20 | | <20[2] | <20 | <20 | <20 | XX[4] | <20 | <20 |
| DEW-8 | 80 | 80 | 80 | 80[1] | 40 | 40 | | 20[2] | <20 | 1280[3] | 2560 | | | |
| DFW-8 | 80 | 80 | 80 | 40[1] | 40 | 40 | | 20[2] | 80[3] | 80 | 320 | | | |
| CTW-8 | 40 | 40[1] | | 20 | 20 | <20 | <20[2] | 10240[3] | 5120 | 5120 | 2560 | | | |
| CWW-8 | 40 | 40[1] | | 40 | <20 | 20480[3] | 10240[2] | 10240 | 5120 | 5120 | 5120 | | | |
| DHW-8 | 80 | 40 | 40 | 20[1] | 20 | <20 | | <20[2] | <20 | <20 | <20 | XX[4] | <20 | 320[3] |

[1] 1st Monovalent parvo vaccine given
[2] 2nd Monovalent parvo vaccine given
[3] Vaccinal Seroconversion
[4] 3rd Monovalent parvo vaccine given

TABLE 6

| Animal ID | Study Day | | | | | | | | | | |
|---|---|---|---|---|---|---|---|---|---|---|---|
| | Day 0 | Day 1 | Day 7 | Day 14 | Day 21 | Day 28 | Day 35 | Day 42 | Day 29 | Day 63 | Day 84 |
| | | | | | Virus Neutralization Assay | | | | | | |
| BDW-8 | <2 | 1024 | 512 | 256 | 128 | 32 | 32 | __16__ | 8 | *2* | 2 |
| DEW-8 | <2 | 1024 | 512 | 256 | 128 | 64 | 32 | __32__ | 16 | *4* | 1024 |
| DFW-8 | <2 | 1024 | 512 | 256 | 128 | 16 | 32 | __16__ | 16 | *8* | 32 |
| CTW-8 | <2 | 512 | 256 | 64 | 64 | 32 | __16__ | 4 | 4 | >4096 | 1024 |
| CWW-8 | <2 | 512 | 256 | 128 | 64 | 32 | __16__ | 16 | 4 | >4096 | 4096 |
| DHW-8 | <2 | 1024 | 256 | 128 | 64 | 32 | __16__ | __8__ | 8 | *4* | <2 |

Underline = 1st Monovalent parvo vaccine given
Italic = 2nd Monovalent parvo vaccine given Example 10

Prevention and Treatment

This in vivo study utilized MabA v2 antibody. The objective of this study was to validate the dose of live CPV-2 that will be used to challenge dogs in future pivotal studies of MabA v2 and to provide proof of concept for MabA v2 for two indications, both as a prophylactic treatment to prevent CPV-2 infection and as a therapeutic treatment for dogs with CPV-2 infection. See study design summary in Table 7, below.

TABLE 7

| | |
|---|---|
| Identity | Anti-Canine Parvovirus Neutralizing Antibody Chimeric Canine Mab A v2 (SEQ ID NOs: 24 and 25) |
| Protocol Number | KB-030-PLC-301 |
| Protocol Title | Evaluation of the Efficacy of Mab A v2 as a Prophylactic and Therapeutic Treatment in Dogs to Prevent Clinical Signs of CPV-2 Infection |
| Materials and Methods | The study was open label Non-GLP Single-dose laboratory PD and safety study in unvaccinated, CPV-2 titer negative, healthy beagles Puppies were randomized to one of six equal treatment groups |
| Study Population | 12 healthy beagle puppies Equal numbers of males and females 11 weeks of age Weight at least 1.5 kg Sourced from Ridglan Farms Inc., Wisconsin |
| Study Dates | Study Day 1: 22 Jun. 2019 CPV-2 Inoculation: 25 Jun. 2019 Study End: 7 Jul. 2019 |

Twelve dogs were randomized and assigned to one of 6 groups with a male and female in each group. Groups 1-3 were only to receive the live CPV-2 challenge in order to validate the dose required to produce required morbidity and mortality at three different viral logs. Dogs in groups 4 and 5 received Mab A v2 as a prophylactic treatment before inoculation with live CPV-2b. Dogs in group 6 were given Mab A v2 after challenge and confirmed development CPV-2 infection via fecal cage-side ELISA SNAP Test. See Table 8 (below) for CPV-2 inoculation challenge schedule.

TABLE 8

| Group | Number of Dogs | Challenge | Study Day of Inoculation | Route | Dose |
|---|---|---|---|---|---|
| 1 | 2 | CPV-2b | Day 4 | IN | $10^2$ TCID$_{50}$ |
| 2 | 2 | CPV-2b | Day 4 | IN | $10^4$ TCID$_{50}$ |

TABLE 8-continued

| Group | Number of Dogs | Challenge | Study Day of Inoculation | Route | Dose |
|---|---|---|---|---|---|
| 3 | 2 | CPV-2b | Day 4 | IN | $10^6$ TCID$_{50}$ |
| 4* | 2 | CPV-2b | Day 4 | IN | $10^6$ TCID$_{50}$ |
| 5* | 2 | CPV-2b | Day 4 | IN | $10^6$ TCID$_{50}$ |
| 6** | 2 | CPV-2b | Day 4 | IN | $10^6$ TCID$_{50}$ |

*Groups 4 and 5 were treated with Mab on Day 1 per Table 9
**Group 6 was treated with Mab after CPV-2 infection was confirmed by detection of virus in feces (via cage-side CPV-2 ELISA) per Table 10

Groups 4 and 5 were given MabA v2 on study Day 1 per Table 9, below.

TABLE 9

| Group | Number of Dogs | Treatment | Study Day of Treatment | Route | Dose |
|---|---|---|---|---|---|
| 4 | 2 | Mab A v2 | Day 1 | IV | 5 mg/kg |
| 5 | 2 | Mab A v2 | Day 1 | SC | 5 mg/kg |

Group 6 was given Mab A v2 on study Day 7, after each puppy had developed a positive cage-side CPV-2 ELISA test documenting CPV-2 in the feces confirming parvovirus infection. See Table 10, below.

TABLE 10

| Group | Number of Dogs | Treatment | Study Day of Treatment | Route | Dose |
|---|---|---|---|---|---|
| 6 | 2 | Mab A v2 | Upon detection of virus in feces | IV | 5 mg/kg |

This study provided the first pharmacodynamic data on MabA v2 administered subcutaneously. The intravenously administered dose in group 4 dogs provided instantaneous rise in HI titers as predicted. The subcutaneously administered dose in group 5 dogs produced comparable titers over a 24-hour period. In Table 11, below, it can be seen how the intravenous and sub-cutaneous doses differ in timing at which the peak post-administration of MabA v2 HI titers were achieved.

As shown in Table 12, below, administration of MabA v2 produced circulating antibody titers in the dogs within 24 hours (IV) and 48 hours (SC) after administration. Protective passive antibody titers were maintained for 16 days in face of a high load virulent challenge.

TABLE 11

| Treatment Group | Treatment | Dog ID | Serum HI Titers | | | | | | | | |
|---|---|---|---|---|---|---|---|---|---|---|---|
| | | | Day 1 | Day 2 | Day 3 | Day 4 | Day 6 | Day 8 | Day 11 | Day 15 | Day 16 |
| 1 | None | AA1001 | <20 | <20 | <20 | <20 | <20 | <20 | 2560 | 20480 | >20480 |
| | | AA1101 | <20 | <20 | <20 | <20 | <20 | <20 | 320 | 20480 | >20480 |
| 2 | None | AA2001 | <20 | <20 | <20 | <20 | <20 | <20 | 160 | >20480 | >20480 |
| | | AA2101 | <20 | <20 | <20 | <20 | <20 | <20 | 10240 | NA | NA |
| 3 | None | AA3001 | <20 | <20 | <20 | <20 | <20 | <20 | no sample | NA | NA |
| | | AA3101 | <20 | <20 | <20 | <20 | <20 | <20 | 2560 | NA | NA |
| 4 | Mab A v2 (Day 1, IV) | AA4001 | 5120 | 5120 | 5120 | 5120 | 2560 | 2560 | 1280 | 2560 | 2560 |
| | | AA4101 | 10240 | 5120 | 5120 | 5120 | 2560 | 2560 | 2560 | 1280 | 2560 |
| 5 | Mab A v2 (Day 1, SC) | AA5001 | <20 | 2560 | 2560 | 2560 | 2560 | 2560 | 2560 | 1280 | 2560 |
| | | AA5101 | <20 | 2560 | 2560 | 2560 | 2560 | 2560 | 5120 | 1280 | 1280 |
| 6 | Mab A v2 (upon detection of CPV-2 in feces, IV) | AA6001 | <20 | <20 | <20 | <20 | <20 | 5120 | 5120 | 5120 | 10240 |
| | | AA6101 | <20 | <20 | <20 | <20 | <20 | 5120 | 10240 | 10240 | 10240 |

TABLE 12

| Treatment Group | Treatment | Dog ID | CPV-2 SVN Antibody Titers | | | | | | | | |
|---|---|---|---|---|---|---|---|---|---|---|---|
| | | | Day 1 | Day 2 | Day 3 | Day 4 | Day 6 | Day 8 | Day 11 | Day 15 | Day 16 |
| 1 | None | AA1001 | <10 | <10 | <10 | <10 | <10 | <10 | 2560 | 10240 | 10240 |
| | | AA1101 | <10 | <10 | <10 | <10 | <10 | <10 | 160 | 20480 | 5120 |
| 2 | None | AA2001 | <10 | <10 | <10 | <10 | <10 | <10 | 160 | 5120 | 10240 |
| | | AA2101 | <10 | <10 | <10 | <10 | <10 | <10 | 2560 | NA | NA |
| 3 | None | AA3001 | <10 | <10 | <10 | <10 | <10 | <10 | no sample | NA | NA |
| | | AA3101 | <10 | <10 | <10 | <10 | <10 | <10 | 2560 | NA | NA |
| 4 | Mab A v2 (Day 1, IV) | AA4001 | 2560 | 2560 | 1280 | 1280 | 1280 | 640 | 640 | 320 | 320 |
| | | AA4101 | 2560 | 1280 | 1280 | 1280 | 1280 | 640 | 320 | 320 | 320 |
| 5 | Mab A v2 (Day 1, SC) | AA5001 | <10 | 640 | 640 | 1280 | 640 | 640 | 640 | 320 | 320 |
| | | AA5101 | <10 | 640 | 640 | 1280 | 1280 | 640 | 640 | 320 | 320 |
| 6 | Mab A v2 (upon detection of CPV-2 in feces, IV) | AA6001 | <10 | <10 | <10 | <10 | <10 | 1280 | 5120 | 5120 | 5120 |
| | | AA6101 | <10 | <10 | <10 | <10 | <10 | 640 | 5120 | 5120 | 5210 |

NA Not applicable

On Day 1, groups 4 and 5 were given MabA v2 intravenously or subcutaneously, respectively. On Day 4, all 12 dogs in all 6 groups were administered virulent CPV-2 intranasally per the inoculation dose in Table 8. For a total of 14 days, the dogs were monitored every 6 hours to record General Health Observations (GHO), every 12 hours to document clinical scores (via validated system, Mohr et al, 2003), and frequent sampling of blood for hematology, HI, and VN as well as fecal hemagglutination assay (HA). Additionally, all dogs were given a cage-side CPV-2 ELISA test every day after inoculation until tested positive to evaluate when parvovirus infection was present. Table 13 summarizes the clinical signs of CPV-2 observed during the study.

TABLE 13

| Group | Dog ID | Diarrhea, blood or mucus in feces | RT ≥ 103.4° F. | Lymphopenia ≥ 50% | Fecal Viral HA | Early Euthanasia |
|---|---|---|---|---|---|---|
| 1 | AA1001 | + | − | − | + | − |
| | AA1101 | − | − | − | − | − |
| 2 | AA2001 | + | − | − | + | − |
| | AA2101 | + | − | + | + | + (at study day 11) |
| 3 | AA3001 | − | − | + | + | + (at study day 10) |
| | AA3101 | + | + | + | + | + (at study day 11) |
| 4 | AA4001 | − | − | − | − | − |
| | AA4101 | − | − | − | − | − |
| 5 | AA5001 | − | − | − | − | − |
| | AA5101 | − | − | − | − | − |
| 6 | AA6001 | − | − | + | − | − |
| | AA6101 | − | − | + | + | − |

Dogs in groups 3 and 6 (those who were challenged with $10^6$ live CPV-2 and not pre-treated with MabA v2) showed positive cage-side CPV-2 ELISA tests on the third or fourth day post-inoculation. Both dogs in group 3 (effectively the control group) developed profound classic clinical signs of parvovirus infection including depression, vomiting, bloody diarrhea, progressive dehydration and were moribund and euthanized by 7 days post-inoculation. Both dogs in group 6 tested positive on cage-side CPV-2 ELISA test 3 days after inoculation with live CPV-2. After confirming the positive cage-side CPV-2 ELISA test they were subsequently treated with Mab A v2 intravenously at 5 mg/kg. They received no additional adjunctive or supportive care.

While the dogs in group 3 continued to get sicker and eventually became moribund and were humanely euthanized, the dogs in group 6 survived and experienced full clinical recovery during the study period. Group 6 dogs also returned to a negative cage-side CPV-2 ELISA test, indicating that they were no longer shedding viral particles.

All dogs in groups 4 and 5 given Mab A v2 as a prophylactic treatment not only survived, but remained healthy (e.g. never developed a positive cage-side CPV-2 ELISA and never exhibited clinical signs of parvovirus infection).

Anatomic histopathology of Groups 3-6 following humane euthanasia at scheduled study completion was performed, unless euthanasia was performed early for humane reasons. Groups 4 and 5 showed no significant pathologic changes. Group 6 showed lymphoid depletion of the thymus, but the other organs examined were normal. Group 3 showed lymphoid depletion of all lymphoid organs, moderate to severe small intestinal villus atrophy/necrosis with mild to severe crypt necrosis indicative of CPV-2 infection.

This pilot proof of concept study demonstrated Mab A v2 is promising as a prophylactic and therapeutic intervention. All dogs in the prophylactic groups (n=4) never developed parvovirus infection and remained clinically normal. All dogs in the therapeutic group (n=2) which were confirmed to be infected with parvovirus survived and experienced full clinical recovery after administration of Mab A v2 with no other adjunctive or supportive treatments. This study also validated that sub-cutaneous dosing of Mab A v2 for prophylaxis is a viable option. Finally, the product was well-tolerated with no adverse events or injection site reactions. In this proof of concept study, prophylactic administration of Mab A v2 prior to challenge protected 100% of puppies from CPV-2 infection. In addition, 100% of puppies given therapeutic administration of Mab A v2 after confirmed CPV infection survived and recovered.

Example 11

Therapeutic Treatment Pivotal Effectiveness Study

This pivotal study evaluates the effectiveness of Mab A v2 as a treatment of canine parvovirus (CPV) disease. Satisfactory completion of this study and demonstration of efficacy may support a label claim stating, "This product has been shown to be effective for the treatment of dogs 13 weeks of age or older against canine parvovirus (CPV) disease."

This GCP, randomized, blinded, placebo-controlled study is 14 days in length following at least 7-days acclimation period. A total of 28 naïve, CPV-2 titer negative dogs (≤13 weeks old on Day 0, of any sex, and weighing ≥1.5 kg) are randomized to the study at a 3:1 ratio to two groups (n=21 dogs in Group 1 and n=7 in Group 2) as per Table 14.

During acclimation, the dogs are acclimated to feeding, housing and handling procedures while being administered anthelmintic and antibiotic medications to eliminate common helminth and coccidia infections.

The day of CPV-2b challenge is considered as Day 0. On Day 0 all dogs in Groups 1 and 2 are administered virulent CPV-2b at a dose of approximately $1 \times 10^6$ TCID$_{50}$ intranasally (IN) (approximately 1 mL volume; approximately 0.5 mL per nostril). On the same day as detection of CPV in feces (via positive cage-side CPV SNAP test) each dog is administered Mab A v2 or Control Product (CP; phosphate buffered saline (PBS)) via intravenous (IV) injection to an accessible vein (e.g., cephalic) catheter using a luer-lock syringe. Mab A v2 is administered in a single 5 mg/kg dose based on body weight. The CP has a pH of 7.2±0.2. The dose for Mab A v2Mab A v2 and CP is calculated as follows:

{(Body weight in kg)×(5 mg/kg)}÷{25 mg/mL}=volume in mL to be injected

At the scheduled times outlined in Table 15 individual dog health is closely monitored for 14 days with physical examinations (PEs), general health observations (GHO), measurement of rectal temperature (RT), cage-side CPV SNP test, serum HI, fecal hemagglutination assay (HA), serum biochemistry, and hematology.

The primary efficacy variable is prevention of mortality from CPV infection in Group 1 dogs versus Group 2 dogs.

See treatment groups in Table 14 below.

TABLE 14

| Group | Number of Dogs | Treatment | Day | Route | Concentration (mg/mL) | Dose |
|---|---|---|---|---|---|---|
| 1 | 21 | IVP | Day of Positive CPV SNAP Test | IV | 25 mg/mL | 5 mg/kg |
| 2 | 7 | CP | Day of Positive CPV SNAP Test | IV | NA | Volume equivalent to Group 1 |

Randomization. This study may require a two-step randomization. The first step is to determine which 28 dogs are enrolled in the study. Dogs are then randomized at a block size of 4 based on litter if possible, with a 3:1 ratio to Groups 1 and 2, respectively. The randomization is based on random numbers generated by the PLAN procedure in SAS (version 9.4 or later, SAS Institute, Cary NC) using the randomized selection method with a seed number.

After arrival to the Test Facility, dogs are placed into cages in 2 rooms based on the order of arrival, and dogs from the same litter/block stay in the same room if possible. Dogs might get secondary exposure to virus that is shed from infected dogs. To keep a similar level of secondary virus exposure for both treatment groups and to maintain blinding to Test Facility personnel, each room contains both treatment groups. After the 28 dogs are selected, their cages are sequentially numbered from 1-28. Dogs from the same litter have adjacent cage numbers, with litters of 4 taking earlier numbers (e.g., 1-4, 5-8, etc.) per room. One room should contain cage numbers 1-12, and the other room contain cage numbers 13-28. The dogs are enrolled in the order of cage numbers in the randomization list.

Study Blinding. The Investigator and all other Test Facility Personnel (excluding the Dispenser and one designated person who restrains dogs for dosing) do not have knowledge of the actual treatment group assignment at Day 0. Only the Dispenser and the person designated for restraining dogs during dosing at the Test Facility have access to actual treatment group assignment (Mab A v2 or CP) for each dog. The Dispenser and the dog restrainer/holder do not perform any study assessments.

Specifications. A total of at least 30 purpose-bred, unvaccinated, CPV-2 seronegative (HI<20), healthy Beagle dogs are procured. The dogs are confirmed CPV negative via CPV SNAP test upon arrival to the Test Facility. Although the study enrollment includes 28 dogs, two additional dogs are purchased to ensure dog numbers are met after screening and acclimation. Ideally, the 30 dogs are comprised of 7 litters with 4 dogs per litter, plus 2 dogs from another litter (a partial litter).

Pivotal Potency Determination. The pivotal efficacy serial sets the release potency of subsequent serials, each serial needs to be at, or above potency of the pivotal efficacy serial as compared in the potency assay in order to be considered satisfactory for release. In order to set a Master Reference for the potency assay, the pivotal efficacy serial is tested using the reference monitoring assay(s). The testing is conducted on Day 0±7 days of administration for the first efficacy dose administered to the study dogs.

Observations

Physical Examination (PE). Physical examinations are performed on all dogs by the Test Facility Veterinarian on at least Days −7, −1, Mab A v2/CP dosing day, Day 13 and on an unscheduled basis when necessary. Physical examinations include a comprehensive assessment of all body systems, including hydration status and BW, and are recorded.

Food Consumption. Once daily, qualitative assessment of food consumption is made in conjunction with general health observations (GHOs). All abnormalities in food consumption observed are recorded.

General Health Observations (GHOs) and Measurement of Rectal Temperature (RT). GHOs are conducted by the Test Facility Veterinarian or their designee at least once daily during the acclimation period from Day −7 through Day −1. GHOs are conducted every 12 hours (±1 hour) starting on Day 0 through Day 12. Beginning on Day 0, in conjunction with each GHO, the RT is also measured using a calibrated thermometer in Fahrenheit scale.

Specific GHO information are collected on these four parameters:
- Attitude—recorded as normal, mild to moderate depression, severe depression, or collapsed or moribund
- Appetite—recorded as normal, voluntarily eats small amounts, no interest in food, or not offered
- Vomiting—recorded as absent, mild (once per 12 hours), moderate (2-5 times per 12 hours), or severe (≥6 times per 12 hours)
- Feces—recorded as well-formed or absent, soft or pasty feces, watery non-bloody diarrhea, or water, bloody diarrhea GHOs may also include other observations in addition to these four parameters. These parameters are documented for each dog at each observation period.

Cage-side CPV SNAP Test. Cage-side CPV ELISA tests are performed using the IDEXX CPV SNAP test according to the manufacturer's instructions. Preliminary CPV SNAP tests are performed on all dogs upon arrival on Day −7 from the Vendor to confirm the dogs do not have active CPV infection. Subsequent CPV SNAP tests are evaluated at a consistent time of morning from Day −1 through study termination. In the unlikely event that a dog does not test positive on CPV SNAP test and therefore does not receive Mab A v2/CP, it is excluded from efficacy analysis.

Serum CPV-2 Hemagglutination (HI) Testing. Whole blood samples are collected (approximately 1.5 mL) from all dogs via a jugular, cephalic, or lateral saphenous vein into serum separator tubes and processed to serum on Days −7, 0, 3, 4, 6, 8, 10, and 13 with the Day 0 sample being collected prior to being challenged with virulent CPV-2b. Samples are also collected prior to unscheduled euthanasia. Samples are inventoried and expedited in shipment on dry ice to the Laboratory Investigator at the earliest opportunity. Samples are stored at frozen conditions (≤−60° C.) until shipment. Data are recorded.

Fecal CPV-2 Hemagglutination Assay (HA) Testing. A bulk fecal sample is collected from each dog on Day 0 through study termination. Bulk feces is collected from each dog into a 50 mL tube, individually frozen, and kept for fecal HA testing to validate CPV SNAP test results and to meet one of the four CPV-2b infection criteria. Fecal samples are homogenized prior to HA testing to maximize accuracy of results and sample size. Procedures for collection, storage and shipping of feces follow the Laboratory Investigator's instructions. Data are recorded.

CPV-2b Infection Criteria. The criteria for CPV infection are in accordance with 9 CFR § 113.317, (c), (3), (i). This regulation defines the four criteria for an active CPV infection. A valid CPV-2b challenge should produce three of the four criteria or mortality in at least four of seven CP dogs. Per 9 CFR § 113.317 definition, the four criteria of parvovirus are as follows:

- Body temp ≥103.4° F.
- Lymphopenia of ≥50% of pre-challenge normal
- Diarrhea, mucus and/or blood in the feces
- Viral hemagglutinins at a level of ≥1:64 in a 1:5 dilution of feces (or a test of equal sensitivity)

These four criteria are monitored daily in all dogs via q 12-hour GHOs including rectal temperature (RT), hematology at specified intervals to monitor lymphocyte counts, and CPV SNAP tests which are performed daily with results verified via fecal HA. Post challenge, dogs from either group that die due to CPV infection are considered a mortality from CPV infection. Dogs that are deemed moribund and must be euthanized via the rescue clause are also considered a mortality from CPV infection.

Clinical Pathology (Hematology and Clinical Biochemistry). On Day −7 a baseline complete blood count (CBC) and biochemical profile is evaluated to verify the dogs are healthy with no pre-existing conditions. On Days −1, 0, 3, 4, 5, 6, 7, 8, 10 and 13 blood is collected for CBC to monitor blood lymphocyte counts. The samples should be collected at a consistent time each morning and recorded. Approximately 0.5 mL of blood is collected for hematology and approximately 1 mL of blood is collected for clinical biochemistry via any accessible vein (e.g. jugular, cephalic, or lateral saphenous vein). All samples are analyzed to evaluate CBC data in real-time to determine if lymphopenia has occurred which is one of the four clinical signs consistent with active CPV per 9 CFR 113.317.

Effectiveness Outcomes

Primary Outcome. The primary efficacy variable is CPV-induced mortality. Mortality rate in Mab A v2 and CP groups is calculated. The prevented fraction (PF) and lower 95% confidence limit is calculated to compare the Mab A v2 group to the CP group with Room as a stratified variable using the Cochran-Mantel-Haenszel method (the FREQ procedure in SAS, SAS Institute, Cary NC, version 9.4 or later). In case the PF cannot be generated due to the data (e.g., 100% Mab A v2 survival rate), and results are homogenous across rooms, the same analysis without Room as a stratified variable is conducted. The primary efficacy endpoint is met if the lower 95% confidence limit of the PF is >0 and the mortality rate in the CP group is higher than the Mab A v2 group. Mortality in Mab A v2/CP dogs is defined as death from CPV infection or dogs which are deemed moribund and must be euthanized via the rescue clause. In the unlikely event that a dog does not test positive on CPV SNAP test and therefore does not receive Mab A v2/CP, it is excluded from efficacy analysis.

Rescue Clause. If an individual dog is deemed moribund by the Test Facility Veterinarian, they can remove the dog from the study via the rescue clause and elect euthanasia. Dogs removed from the study for humane reasons are included in the efficacy assessment as a "mortality" unless the reason for euthanasia is unrelated to CPV.

The schedule of events is provided in Table 15 below.

6. Use syringe (without needle) with nasal canula to administer 0.5 mL into each nostril.
7. Restraint is by hand; no sedation is needed.
8. Handler holds the dog's head up with nose slightly elevated during dosing.
9. Allow a few seconds time between each nostril for the dog to swallow and be comfortable.
10. Expect that some challenge material may be expelled from the nostrils.

TABLE 15

| | Acclimation | | | | | | | In-Life | | | |
|---|---|---|---|---|---|---|---|---|---|---|---|
| | Study Day | | | | | | | | | | |
| | Day −7 | Day −6 | Day −5 | Day −4 | Day −3 | Day −2 | Day −1 | Day 0 | Day 1 | Day 2 | Day 3 |
| GHOs and RT[1] | X | X | X | X | X | X | X | q12 | q12 | q12 | q12 |
| PE and BW[2] | X | | | | | | X | | | | |
| IVP/CP Dose[3] | | | | | | | | | TBD | | |
| Intranasal CVP-2b Challenge | | | | | | | | X | | | |
| Randomization | | | | | | | X | | | | |
| Hematology | X | | | | | | X | X | | | X |
| Biochemistry | X | | | | | | | | | | |
| CPV SNAP Test | X | | | | | | X | X | X | X | X |
| CPV-2 HI (serum) | X | | | | | | | X | | | X |
| Bulk feces collection for CPV-2 HA (feces)[4] | | | | | | | | X | X | X | X |
| Fenbendazole | X | X | X | X | X | | | | | | |
| Sulfadimethoxine | X | X | X | X | X | | | | | | |
| Study Termination | | | | | | | | | | | |

| | In-Life | | | | | | | | | | May also be |
|---|---|---|---|---|---|---|---|---|---|---|---|
| | Study Day | | | | | | | | | | |
| | Day 4 | Day 5 | Day 6 | Day 7 | Day 8 | Day 9 | Day 10 | Day 11 | Day 12 | Day 13 | Unscheduled |
| GHOs and RT[1] | q12 | q12 | q12 | q12 | q12 | q12 | q12 | q12 | q12 | | X |
| PE and BW[2] | | | | | | | | | | X | X |
| IVP/CP Dose[3] | | | | | | | | | | | |
| Intranasal CVP-2b Challenge | | | | | | | | | | | |
| Randomization | | | | | | | | | | | |
| Hematology | X | X | X | X | X | | X | | | X | |
| Biochemistry | | | | | | | | | | | |
| CPV SNAP Test | X | X | X | X | X | X | X | X | X | X | X |
| CPV-2 HI (serum) | X | | X | | X | | X | | | X | |
| Bulk feces collection for CPV-2 HA (feces)[4] | X | X | X | X | X | X | X | X | X | X | X |
| Fenbendazole | | | | | | | | | | | |
| Sulfadimethoxine | | | | | | | | | | | |
| Study Termination | | | | | | | | | | X | |

[1] GHOs occur at least once daily during Acclimation. On Day 0, GHOs and rectal temperature (RT) are recorded every 12 hours (±1 hour) through study termination.
[2] PE and BW are also performed on the same day as IVP/CP Dosing.
[3] IVP/CP Dose are administered upon detection of CPV-2 in individual dog's feces using the CPV SNAP test.
[4] Fecal HA are conducted to verify parvovirus infection and validate CPV SNAP test results.

The following is the Canine Parvovirus Challenge Inoculation Procedure:
1. Remove food ~12 hours before the challenge material is administered. Water remains available.
2. Remove the challenge material from the ultracold (−80° C.) freezer and allow to thaw at room temperature approximately 1 hour before use.
3. Thaw five extra aliquots in order to have back-up doses in case of handling error.
4. Retain challenge material on wet ice until use.
5. Draw up 1 mL aliquot challenge material with a syringe one dose at a time.
11. Record Dog ID, date and time on the Animal Challenge Record as dosing is completed.
12. Return food to all dogs immediately after dosing.
13. Return unused challenge material to −80° C. freezer, label as "retention aliquot, date".
14. Retain aliquot until study end and return to the Laboratory Investigator.

The following is the Bulk Feces Collection Procedure:
1. Select individual fecal pile (or section of pile) that appears to be most abnormal.
2. Using a separate wooden tongue depressor, collect up to several grams of feces from each individual dog— one collection per dog per day. Highly diarrheic feces may need to be collected using a syringe.
3. Place feces into 50 mL conical plastic centrifuge tube. Tube should be no more than half full.
4. Label with Dog ID and date.
5. Store in plastic freezer bags, grouped by date and treatment group.
6. Freeze at −80° C. until shipping to the Laboratory Investigator.
7. At the end of the collection period, ship all collected feces on dry ice to arrive overnight to the Laboratory Investigator.

Example 12

Prophylaxis Pivotal Effectiveness Study

The purpose of this pivotal study is to evaluate the effectiveness of Mab A v2 as a prophylactic therapy to prevent clinic signs of canine parvovirus (CPV) infection.

Satisfactory completion of this study and demonstration of efficacy may support a label claim stating, "This product has been shown to be effective for passive immunity of healthy dogs 13 weeks of age or older against canine parvovirus (CPV) disease".

This GCP, randomized, blinded, placebo-controlled study is 14 days in length following at least a 7-day acclimation period. A total of 25 naïve, CPV-2 seronegative (CPV hemagglutination inhibition (HI) titer <20) dogs are randomized to two groups (n=20 dogs in Group 1 and n=5 in Group 2) as per Table 16. Dogs are ≤13 weeks old on Day 0, of any sex, weigh ≥1.5 kg upon arrival and are in good health and free from any clinical signs of disease at study start.

During acclimation, the dogs are acclimated to feeding, housing and handling procedures while being administered anthelmintic and antibiotic medications to eliminate common helminth and coccidia infections.

On Day 0, all dogs are administered their assigned Mab A v2 (Group 1) or Control Product [CP; Group 2; phosphate buffered saline (PBS)] via subcutaneous (SC) injection. Mab A v2 is administered in a single 5 mg/kg dose based on body weight. The CP has a pH of 7.2±0.2 administered in a volume equal to Group 1. The dose for Mab A v2 and CP is calculated as follows:

{(Body weight in kg)×(5 mg/kg)}÷{25 mg/mL}=volume in mL to be injected

Local and systemic safety data are collected from Day 0 (post treatment) to Day 2. On Day 3 all dogs from both Groups 1 and 2 are administered virulent CPV-2b at a dose of approximately $1\times10^6$ $TCID_{50}$/mL intranasally (IN) (a volume equaling approximately 0.5 mL per nostril).

At scheduled times outlined in Table 17 individual dog health is closely monitored for 14 days with physical examinations (PEs), measurement of rectal temperature (RT), cage-side CPV-2 ELISA IDEXX SNAP test (CPV SNAP test), serum hemagglutination inhibition assay (HI), fecal hemagglutination assay (HA), and hematology.

The primary efficacy variable is prevention of CPV infection in Group 1 dogs as defined by the criteria of 9 CFR § 113.317, (c), (3), (i):
Body temp ≥103.4° F.
Lymphopenia of ≥50% of pre-CPV-2b challenge normal
Diarrhea, mucus and/or blood in feces
Viral hemagglutinins at a level of ≥1:64 in a 1:5 dilution of feces (or a test of equal sensitivity)

Efficacy is demonstrated if at least 80% of Group 2 (CP) dogs have at least three of the four criteria outlined in 9 CFR § 113.317, (c), (3), (i) and if at least 19 Mab A v2 treated dogs remain alive and show ≤1 of the four possible clinical signs.

See treatment groups in Table 16 below.

TABLE 16

| Group | Number of Dogs | Treatment | Route | Concentration (mg/mL) | Dose |
|---|---|---|---|---|---|
| 1 | 20 | Mab A v2 | SC | 25 mg/mL | 5 mg/kg |
| 2 | 5 | CP | SC | 25 NA | Volume equivalent to Group 1 |

Randomization. This study may require a two-step randomization. The first step is to determine which 25 dogs are enrolled in the study. Dogs are then randomized at a block size of 5 with a 4:1 ratio to Groups 1 and 2, respectively. The randomization is based on random numbers generated by the PLAN procedure in SAS (version 9.4 or later, SAS Institute, Cary NC) using the randomized selection method with a seed number.

After arrival to the Test Facility, dogs are placed into cages in 2 rooms based on the order of arrival, and dogs from the same litter/block stay in the same room if possible. Dogs might get secondary exposure to virus that is shed from infected dogs. To keep a similar level of secondary virus exposure for both treatment groups and to maintain blinding to Test Facility personnel, each room contains both treatment groups. After the 25 dogs are selected, their cages are sequentially numbered from 1-25. Dogs from the same litter have adjacent cage numbers, with litters of 5 taking earlier numbers (e.g., 1-5, 6-10, etc.) per room. One room should contain cage numbers 1-10, and the other room contain cage numbers 11-25. The dogs are enrolled in the order of cage numbers in the randomization list.

Masking of Study. The Investigator and all other Test Facility Personnel (excluding the Dispenser and one designated person who restrains dogs for dosing) do not have knowledge of the actual treatment group assignment at Day 0. Only the Dispenser and the person designated for restraining dogs during dosing at the Test Facility has access to actual treatment group assignment (Mab A v2 or CP) for each dog. The Dispenser and the dog restrainer/holder do not perform any study assessments.

Specifications. A total of at least 27 purpose-bred, unvaccinated, CPV-2 seronegative (HI<20), healthy Beagle dogs re procured. The dogs are confirmed CPV negative via CPV SNAP test upon arrival to the Test Facility. Although the study enrollment includes 25 dogs, two additional dogs are purchased to ensure dog numbers are met after screening and acclimation. Ideally, the 27 dogs are comprised of 5 litters with 5 dogs per litter, plus 2 dogs from another litter (a partial litter).

Observations

Physical Examination (PE). Physical examinations are performed on all dogs by the Test Facility Veterinarian on Days −7, 0, 3, 13 and on an unscheduled basis when necessary. Physical examinations include a comprehensive assessment of all body systems, including hydration status and BW.

Food Consumption. Once daily, qualitative assessment of food consumption is made in conjunction with general health observations (GHOs). All abnormalities in food consumption observed are recorded.

Injection Site Observations (ISO). ISO is made at 4 hours±1 hour after administration of Mab A v2/CP for clinical signs of local inflammation (e.g. erythema, heat or swelling) once daily on Day 1 and Day 2. The size of any reactions is recorded. All abnormalities observed are recorded.

General Health Observations (GHOs) and Measurement of Rectal Temperature (RT). GHOs are conducted by the Test Facility Veterinarian or their designee once daily during the acclimation period from Day −7 through Day −1. GHOs are conducted every 12 hours (±1 hour) from Day 0 through Day 12 or on an unscheduled basis. Beginning on Day 0, in conjunction with each GHO, the rectal temperature (RT) is also measured using a calibrated thermometer in Fahrenheit scale. General health observations include, but are not be limited to, observations of general physical appearance, abnormalities of food or water consumption, and/or occurrence of vomiting or diarrhea. The condition of all dogs, including those without abnormal signs, are documented.

Cage-side CPV ELISA (CPV SNAP Test). Cage-side CPV ELISA tests are performed using the IDEXX CPV SNAP test according to the manufacturer's instructions. Preliminary CPV SNAP tests are performed on all dogs upon arrival on Day −7 from the Vendor to confirm the dogs do not have active CPV infection. Subsequent CPV SNAP tests are evaluated at a consistent time of morning on Day 0, Day 3 (prior to inoculation with virulent CPV-2b) and then once daily through study termination. CPV SNAP test data are recorded.

Serum CPV-2 Hemagglutination (HI) Testing. Whole blood samples are collected (~1.5 mL) from all dogs via a jugular, cephalic, or lateral saphenous vein into serum separator tubes and processed to serum at a consistent time of morning on Days −7, 0, 2, 3, 4, 6, 8, 10, and 13 with the Day 3 sample being collected prior to inoculation with virulent CPV-2b. Samples are also collected prior to unscheduled euthanasia. Samples are inventoried and expedited in shipment on dry ice to the Laboratory Investigator at the earliest opportunity. Samples are stored at frozen conditions (≤−60° C.) until shipment. Data are recorded.

Fecal CPV-2 Hemagglutination Assay (HA) Testing. A bulk fecal sample is collected from each dog on Day 0, and Day 3 through study termination at a consistent time of morning. Bulk feces is collected from each dog into a 50 mL tube, individually frozen, and kept for fecal HA testing to validate CPV SNAP test results and to meet one of the four CPV-2b infection criteria. Fecal samples are homogenized prior to HA testing to maximize accuracy of results and sample size. Procedures for collection, storage and shipping of feces follow the Laboratory Investigator's instructions. Data are recorded.

CPV-2b Infection Criteria. The criteria for CPV infection are in accordance with 9 CFR § 113.317, (c), (3), (i). This regulation defines the four criteria for an active CPV infection. A valid CPV-2b challenge should produce three of the four criteria in at least 80% of the challenge control dogs. Per 9 CFR § 113.317 definition, the four criteria of parvovirus are as follows:

Body temp ≥103.4° F.
Lymphopenia of ≥50% of pre-challenge normal
Diarrhea, mucus and/or blood in the feces
Viral hemagglutinins at a level of ≥1:64 in a 1:5 dilution of feces (or a test of equal sensitivity)

These four criteria are monitored daily in all dogs via q 12-hour GHOs including rectal temperature (RT), hematology at specified intervals to monitor lymphocyte counts, and CPV SNAP tests which are performed daily with results verified via fecal HA.

Clinical Pathology (Hematology and Clinical Biochemistry). On Day −7 a baseline complete blood count (CBC) and biochemical profile is evaluated to verify the dogs are healthy with no pre-existing conditions. On Days 0, 3, 5, 6, 7, 8, 9, 10 and 13 blood is collected for CBC to monitor blood lymphocyte counts. The samples are collected at a consistent time each morning and recorded. Approximately 0.5 mL of blood is collected for hematology and approximately 1 mL of blood is collected for clinical biochemistry via any accessible vein (e.g. jugular, cephalic, or lateral saphenous vein). All samples are analyzed to evaluate CBC data in real-time to determine if lymphopenia has occurred which is one of the four clinical signs consistent with active CPV per 9 CFR 113.317.

Effectiveness Outcomes

Primary Outcome. The primary efficacy variable is prevention of CPV infection as defined by the criteria of 9 CFR § 113.317, (c), (3), (i):

Body temp ≥103.4° F.
Lymphopenia of ≥50% of pre-CPV-2b challenge normal (Average of Days −7, 0 and 3 pre-challenge)
Diarrhea, mucus and/or blood in feces
Viral hemagglutinins at a level of ≥1:64 in a 1:5 dilution of feces (or a test of equal sensitivity) Efficacy is established if 80% of control dogs have three of the four criteria outlined in 9 CFR 113.317 and if at least 19 Mab A v2 treated dogs remain alive and show ≤1 of the four possible clinical signs.

Second Outcomes. Secondary outcomes such as CPV SNAP test results, serum HI titers, or other parameters may be evaluated.

Safety Outcomes. Dogs from this pivotal study are applied to the required number of dogs treated in the Mab A v2 Pivotal Field Safety Study. Safety evaluation is through collation of all local and systemic adverse events (AEs) from Day 0 (post-treatment) through Day 3. Specifically, dogs are monitored for injection site reactions such as erythema, heat and swellings (via daily ISO) and systemic reactions, including anaphylaxis post administration of Mab A v2. The AE data are not statistically analyzed but are summarized and tabulated for final reporting.

Serious AE. A serious AE is any AE that results in death, is life-threatening, results in persistent or significant disability/incapacity, or a congenital anomaly or birth defect. The Study Investigator notifies the Clinical Development Manager within 24 hours of the occurrence of any serious AE.

The schedule of events is provided in Table 17 below.

TABLE 17

| | Acclimation Phase | | | | | | | Treatment/Observation | | | |
|---|---|---|---|---|---|---|---|---|---|---|---|
| | Study Day | | | | | | | | | | |
| | Day −7 | Day −6 | Day −5 | Day −4 | Day −3 | Day −2 | Day −1 | Day 0 | Day 1 | Day 2 | Day 3 |
| GHOs [1] | X | X | X | X | X | X | X | q 12 | q 12 | q 12 | q 12 |

TABLE 17-continued

| | Day −6 | Day −5 | Day −4 | Day −3 | Day −2 | Day −1 | Day 0 | Day 1 | Day 2 | Day 3 |
|---|---|---|---|---|---|---|---|---|---|---|
| Randomization | | | | | | X | | | | |
| PE | X | | | | | | X | | | X |
| Rectal Temperature (RT) | | | | | | | q12 | q12 | q12 | q12 |
| IVP/CP Dose | | | | | | | X | | | |
| Intranasal CVP-2b Challenge | | | | | | | | | | X |
| ISO | | | | | | | X | X | X | |
| Hematology | X | | | | | | X | | | X |
| Biochemistry | X | | | | | | | | | |
| CPV SNAP Test[2] | X | | | | | | X | | | X |
| CPV-2 HI (serum) | X | | | | | | X | | X | X |
| Bulk feces collection for CPV-2 HA (feces)[3] | X | | | | | | | | | X |
| Fenbendazole | X | X | X | X | X | | | | | |
| Sulfadimethoxine | X | X | X | X | X | | | | | |

| | Treatment/Observation Study Day | | | | | | | | | |
|---|---|---|---|---|---|---|---|---|---|---|
| | Day 4 | Day 5 | Day 6 | Day 7 | Day 8 | Day 9 | Day 10 | Day 11 | Day 12 | Day 13 | Unscheduled |
| GHOs [1] | q12 | q12 | q12 | q12 | q12 | q12 | q12 | q12 | q12 | X | X |
| Randomization | | | | | | | | | | | |
| PE | | | | | | | | | | X | X |
| Rectal Temperature (RT) | q12 | q12 | q12 | q12 | q12 | q12 | q12 | q12 | q12 | q12 | X |
| IVP/CP Dose | | | | | | | | | | | |
| Intranasal CVP-2b Challenge | | | | | | | | | | | |
| ISO | | | | | | | | | | | |
| Hematology | | X | X | X | X | X | X | | | X | |
| Biochemistry | | | | | | | | | | | |
| CPV SNAP Test[2] | X | X | X | X | X | X | X | X | X | X | X |
| CPV-2 HI (serum) | X | | X | | X | | X | | | X | |
| Bulk feces collection for CPV-2 HA (feces)[3] | X | X | X | X | X | X | X | X | X | X | X |
| Fenbendazole | | | | | | | | | | | |
| Sulfadimethoxine | | | | | | | | | | | | q = Every
GHO = General health observation
PE = Physical examination
CPV-2 = Canine Parvovirus type 2
HI = Hemagglutinin inhibition assay
HA = Hemagglutinin assay
IVP = Investigational Veterinary Product
ISO = Injection Site Observation

[1] GHOs occur every 24 hours during acclimation. After administration of the IVP/CP on Day 0, GHOs are increased to every 12 hours. General health observations includes, but is not limited to, observations of general physical appearance, abnormalities of food or water consumption, and/or occurrence of vomiting or diarrhea.
[2] CPV-2 SNAP test may also be evaluated if a dog is found to have fever, lethargy, vomiting or diarrhea or other signs which the Investigator or Test Facility Veterinarian determines may indicate parvovirus infection.
[3] Fecal HA is conducted to verify parvovirus infection and validate CPV-2 SNAP test results.

The following is the Canine Parvovirus Challenge Inoculation Procedure:
1. Remove food approximately 12 hours before the challenge material is administered. Water remains available.
2. Remove the challenge material from the ultracold (−80° C.) freezer and allow to thaw at room temperature approximately 1 hour before use.
3. Thaw five extra aliquots in order to have back-up doses in case of handling error.
4. Retain challenge material on wet ice until use.
5. Draw up 1 mL aliquot challenge material with a syringe one dose at a time.
6. Use syringe (without needle) with nasal canula to administer 0.5 mL into each nostril.
7. Restraint is by hand; no sedation is needed.
8. Handler holds the dog's head up with nose slightly elevated during dosing.
9. Allow a few seconds time between each nostril for the dog to swallow and be comfortable.
10. Expect that some challenge material may be expelled from the nostrils.
11. Record Dog ID, date and time on the Animal Challenge Record as dosing is completed.
12. Return food to all dogs immediately after dosing.
13. Return unused challenge material to −80° C. freezer, label as "retention aliquot, date".
14. Retain aliquot until study end and return to the Laboratory Investigator.

The following is the Bulk Feces Collection Procedure:
1. Select individual fecal pile (or section of pile) that appears to be most abnormal.
2. Using a separate wooden tongue depressor, collect up to several grams of feces from each individual dog—one collection per dog per day. Highly diarrheic feces may need to be collected using a syringe.

3. Place feces into 50 mL conical plastic centrifuge tube. Tube should be no more than half full.
4. Label with Dog ID and date.
5. Store in plastic freezer bags, grouped by date and treatment group.
6. Freeze at −80° C. until shipping to the Laboratory Investigator.
7. At the end of the collection period, ship all collected feces on dry ice to arrive overnight to the Laboratory Investigator.

Example 13

Half-Life Degradation and Lack of Antibody Interference

This in vivo study monitors degradation of Mab A v2 in vivo and evaluates the duration hemagglutination inhibition (HI) titer levels remain sufficient to neutralize vaccinal strains of CPV. The following objectives are addressed:
  Characterizes the half-life degradation of Mab A v2 after subcutaneous (SC) administration
  Determines the timeframe after administration that Mab A v2 will no longer inhibit active immunization against parvovirus (lack of antibody interference, or LOAI)

Serologic monitoring of HI titers after administration of Mab A v2 may characterize the degradation half-life. LOAI is determined by active immune responses against parvovirus after vaccine administration in at least 80% of dogs within each group. Active response is defined as a four-fold increase in titer over baseline (seroconversion) with achievement of antibody titers equal to or above a 1:80 dilution as determined by HI. This level of antibody response provides immunity against canine parvovirus, as shown by challenge of immunity studies (Pollock and Carmichael, JAVMA 1982 Jan. 1; 180(1):37-42).

Secondarily, safety data are collected post treatment and prior to CPV immunization which may be used contribute to the total number of dogs required to meet the 300-dog minimum requirement by the USDA-CVB to satisfy Veterinary Services Memorandum (VSM) No. 800.204.

Satisfactory completion of this study and demonstration when LOAI to CPV immunization occurs may support two label claims stating:

"This product has been shown to passively immunize healthy dogs 13 weeks of age or older for prevention of canine parvovirus (CPV) disease."

"This product has been shown to be effective for the treatment of canine parvovirus (CPV) disease in dogs 13 weeks of age or older."

In example 9 above, describing prior study KB-030-PK-301, Mab A v2 neutralized vaccinal CPV much like maternally derived antibody. The current study may provide information regarding the timing of CPV vaccination subsequent to administration of the Mab A v2 as a prophylactic therapy.

This is a randomized, non-blinded, open label, GCP study conducted in healthy CPV seronegative Beagle dogs. The study is up to 113 days in length with a 7-day acclimation period. During acclimation, the dogs are acclimated to feeding, housing and handling procedures; and receive an anthelmintic and antibiotic medications to eliminate common helminth and coccidia infections.

On Day 0, 5 mg/kg of Mab A v2 is administered SC in the interscapular region to Groups 1 and 2. Groups 3 and 4 do not receive Mab A v2. From Day 0 to Day 41, general health observations (GHOs), physical examinations (PEs) and injection site observations (ISO) are collected at various time points to monitor the dogs for any local and systemic reactions to the Mab A v2.

On Day 42, one pre-assigned monovalent CPV vaccine is administered to Groups 1 and 3, and another pre-assigned monovalent CPV vaccine is administered to Groups 2 and 4. Each dog is administered the pre-assigned monovalent CPV vaccine (either Vaccine 1 or Vaccine 2) on Day 42 after serum has been collected for HI titers. If vaccinal seroconversion is not documented after the previous vaccine, a booster vaccination ("$2^{nd}$ CPV vaccine") is administered 3 weeks after the first vaccine, on Day 63. If vaccinal seroconversion is not documented after the $2^{nd}$ CPV vaccine, a third booster of the pre-assigned monovalent CPV vaccine ("$3^{rd}$ booster) is administered on Day 84. Study Exit by individual dogs occurs upon receipt of HI results which document seroconversion. In the event that some dogs have not mounted an immune response to vaccination after Day 91 HI titers, a fourth and final monovalent CPV booster ("$4^{th}$ booster") is administered on Day 105. Serum hemagglutination inhibition (HI) titers are measured at various time points to monitor degradation of Mab A v2 and when LOAI to CPV vaccination occurs.

From Day 43 to Study Exit, GHOs and PEs are collected at various time points to monitor the dogs for general health.

The two monovalent CPV vaccines to be preassigned and administered in the study are:

| Vaccine 1 | |
|---|---|
| Registered name: | Nobivac ® Canine 1-PV |
| Vaccine: | Canine parvovirus (modified live) |
| Pharmaceutical form: | Sterile injectable solution |
| Test dose: | 1 mL (1 dose) |
| Route of administration: | Subcutaneous |
| Manufacturer: | Merck Animal Health |
| Packaging: | Individual vials per manufacturer packaging |
| Storage conditions: | 2-7° C. |
| Accountable unit: | 1 vial |
| Vaccine 2 | |
| Registered name: | Recombitek ® |
| Vaccine: | Canine parvovirus (modified live) |
| Pharmaceutical form: | Sterile injectable solution |
| Test dose: | 1 mL (1 dose) |
| Route of administration: | Subcutaneous |
| Manufacturer: | Merial |
| Packaging: | Individual vials per manufacturer packaging |
| Storage conditions: | 2-7° C. |
| Accountable unit: | 1 vial |

See treatment groups in Table 18 below.

TABLE 18

| Group | Number of Dogs | Treatment | Route | Concentration (mg/mL) | Dose | Monovalent Vaccine to be Administered |
|---|---|---|---|---|---|---|
| 1 | ≥10 | Mab A v2 | SC | 25 mg/mL | 5 mg/kg | Vaccine 1 |
| 2 | ≥10 | Mab A v2 | SC | 25 mg/mL | 5 mg/kg | Vaccine 2 |
| 3* | ≥5 | None | NA | NA | NA | Vaccine 1 |
| 4* | ≥5 | None | NA | NA | NA | Vaccine 2 |

Vaccine 1 = Nobivac Canine 1-PV ® (Merck);
Vaccine 2 = Recombitek ® (Merial)

Randomization. Dogs (≤13 weeks old on Day 0, of any sex, and weighing ≥1.5 kg) are randomized at a 2:2:1:1 ratio to Groups 1 through 4 on or before Day 0 using a randomization list provided by the Sponsor's Study Programmer.

Treatment is randomly assigned within each block of 6 dogs. The randomization is based on random numbers generated by the PLAN procedure in SAS (SAS Institute, Cary NC, version 9.4 or later) using the randomized selection method with a seed number.

Observations

Physical Examinations (PEs). PEs are performed on all days on Days −7, 0, Study Exit and on an unscheduled basis when necessary. Physical examinations include a comprehensive assessment of all body systems, including hydration status and body weight (BW).

Injection Site Observations (ISOs). On Day −3 the injection site is clipped in preparation for dosing on Day 0. Prior to dosing, the clipped injection site is evaluated and recorded as free of any inflammation or clipper burn. Beginning on Day 0, the injection site is evaluated once daily through Day 14 for local injection site reactions including but not limited to erythema, heat, and swelling (e.g. nodule). The size of any reactions is recorded. Any injection site reaction observed is documented on the Injection Site Observation Form and is recorded as an adverse event (AE).

General Health Observations (GHOs). GHOs are conducted by the Study Investigator or a designee once daily from Day −7 through Study Termination. General health observations include, but are not limited to, observations of general physical appearance, abnormalities of food or water consumption, and/or occurrence of vomiting or diarrhea. The condition of all dogs, including those without abnormal signs, is documented on the General Health Observation Form for each dog at each observation period. On Days −7, 0 and Study Exit when PEs are conducted, the PE replaces the GHO.

Serum CPV-2 Hemagglutination (HI) Testing. Whole blood samples are collected (approximately 1.5 mL) from all dogs via a jugular, cephalic, or lateral saphenous vein and are placed into serum separator tubes and processed to serum on Days −7, 0, 1, 7, 14, 21, 28, 35, 42, 49, 56, 63, 70, 77, 84, 91, 98, 105, 112. If seroconversion is documented on HI, subsequent scheduled sampling ceases, and the individual dog exits the study. Samples are stored at frozen conditions (60 to −80° C.) until they are delivered to the Analytical Laboratory at the earliest opportunity.

Clinical Pathology. On Day −7 a baseline complete blood count (CBC) and biochemical profile are evaluated to verify the dogs are healthy with no pre-existing conditions. Approximately 0.5 mL of blood is collected for hematology and approximately 1 mL is collected for clinical biochemistry from the jugular, cephalic, or lateral saphenous vein.

Adverse Events (AE). An AE is defined as any observation in dogs that is unfavorable, unexpected, and unintended, and occurs after the use of a veterinary product, whether or not considered to be product related. Once experimental treatment is initiated (Day 0 when Mab A v2 is administered), any abnormal GHO, PE, or ISO is considered an AE.

Primary Endpoint. The primary endpoint for each group is the number of days from Day 0 to the time when ≥80% of dogs within the group have demonstrated CPV seroconversion via serum HI titers to the monovalent CPV vaccination. Seroconversion is defined as a four-fold increase in titer over baseline with achievement of antibody titers equal to or above a 1:80 dilution as determined by serum HI titers. The number of dogs per group that have demonstrated an immune response to vaccines and the study day when this occurred is not statistically analyzed but summarized and tabulated for final reporting.

See the schedule of events in Table 19 below.

TABLE 19

| Study Day | Fenbendazole & Sulfadimethoxine | Randomization[1] | Body Weight | Physical Exam | General Health Observations | Mab Av2 Administration | Injection Site Observations[2] | Serum CPV-2 HI Testing | CBC | Clinical Bio-chemistry | Clip Hair at Injection Site | 1st Monovalent CPV vaccine | 2nd Monovalent CPV vaccine[3] | 3rd Monovalent CPV Vaccine[3] | 4th Monovalent CPV Vaccine[3] |
|---|---|---|---|---|---|---|---|---|---|---|---|---|---|---|---|
| -7 | X | | | | | | | | | | | | | | |
| -6 | X | | | | | | | | | | | | | | |
| -5 | X | | | | | | | | | | | | | | |
| -4 | X | | X | X | X | | | X | X | X | | | | | |
| -3 | | | | | X | | | | | | X | | | | |
| -2 | | | | | X | | | | | | | | | | |
| -1 | | | | | X | | | | | | | | | | |
| 0 | | X | X | X | X | X | | X | | | | | | | |
| 1 | | | | | X | | X | X | | | | | | | |
| 2-6 | | | | | X | | X | | | | | | | | |
| 7 | | | | | X | | X | X | | | | | | | |
| 8-13 | | | | | X | | X | | | | | | | | |
| 14 | | | | | X | | | X | | | | | | | |
| 15-20 | | | | | X | | | | | | | | | | |
| 21 | | | | | X | | | X | | | | | | | |
| 22-27 | | | | | X | | | | | | | | | | |
| 28 | | | | | X | | | X | | | | | | | |
| 29-34 | | | | | X | | | | | | | | | | |
| 35 | | | | | X | | | X | | | | | | | |
| 36-41 | | | | | X | | | | | | | | | | |
| 42 | | | | | X | | | X | | | | X | | | |
| 43-48 | | | | | X | | | | | | | | | | |
| 49 | | | | | X | | | X | | | | | | | |
| 50-55 | | | | | X | | | | | | | | | | |
| 56 | | | | | X | | | X | | | | | | | |
| 57-62 | | | | | X | | | | | | | | | | |
| 63 | | | | | X | | | X | | | | | X | | |
| 64-69 | | | | | X | | | | | | | | | | |
| 70 | | | | | X | | | X | | | | | | | |
| 71-76 | | | | | X | | | | | | | | | | |
| 77 | | | | | X | | | X | | | | | | | |
| 78-83 | | | | | X | | | | | | | | | | |
| 84 | | | | | X | | | X | | | | | | X | |
| 85-90 | | | | | X | | | | | | | | | | |
| 91 | | | | | X | | | X | | | | | | | |
| 92-97 | | | | | X | | | | | | | | | | |
| 98 | | | | | X | | | X | | | | | | | |
| 99-104 | | | | | X | | | | | | | | | | |
| 105 | | | | | X | | | X | | | | | | | X |
| 106-111 | | | | | X | | | | | | | | | | |
| 112 | | | X | X | X | | | X | | | | | | | |

[1] Randomization occurs on or before Day 0.
[2] Injection Site Observations for clinical signs of intolerance (e.g. erythema, heat, swelling) are made daily from Day 0, prior to dosing and after dosing, through Day 14. All abnormal observations are characterized (e.g. size of swelling) and documented on the Injection Site Observation CRF
[3] 2nd, 3rd, and 4th CPV vaccines are only administered to dogs who have not demonstrated seroconversion from the previous vaccine

Example 14

Multi-Center, Pivotal Safety Study in Healthy Dogs

This in vivo field safety study evaluates the local and systemic tolerance of MabA v2. Individual dogs are observed for injection site inflammation (including but not limited to erythema, heat and/or swelling) and for systemic reactions (e.g. anaphylaxis).

A minimum of 300 dogs are administered Mab A v2, either via subcutaneous (SC) (n=150) or via intravenous (IV) (n=150) routes. The safety data collected during this study is intended to meet the pivotal field safety 300-dog requirement for the United States Department of Agriculture Center for Veterinary Biologics (USDA-CVB).

Satisfactory completion of this study and demonstration of safety may support two label claims stating:

"This product has been shown to be effective for passive immunity of healthy dogs 10 weeks of age or older for prevention of canine parvovirus (CPV) disease."

"This product has been shown to be effective for the treatment of canine parvovirus (CPV) disease in dogs 10 weeks of age or older."

Dose volume is calculated in mL by the EDC system based on Day 0 body weight (BW). The dose is calculated by the EDC System as follows:

$$\{(\text{Body weight in kg}) \times (5 \text{ mg/kg})\} \div \{\text{TBD mg/mL}\} = \text{volume in mL to be injected}$$

Subcutaneous doses are administered into the subcutis of the interscapular region. Intravenous doses re administered in a cephalic vein.

At scheduled times outlined in Table 20, individual dog health is closely monitored via physical examinations (PEs), injection site observations (ISO) and general health observations (GHOs).

Safety evaluation is through collation of all adverse events (AEs). Specifically, dogs are monitored for injection site reactions such as erythema, heat or swelling (via daily ISO) and for systemic reactions, including anaphylaxis, post administration of Mab A v2. The AE data are not statistically analyzed but are summarized and tabulated.

See treatment groups in Table 20 below.

TABLE 20

| Group | Number of Dogs of Minimum Age (≤10 weeks) | Number of Dogs of Older Age (>10 weeks) | Mab A v2 Treatment | Route | Concentration (mg/mL) | Dose |
|---|---|---|---|---|---|---|
| 1 | ≥25 | ≥50 | PLS No. 1 | SC | TBD | 5 mg/kg |
| 2 | ≥25 | ≥50 | PLS No. 2 | SC | TBD | 5 mg/kg |
| 3 | ≥25 | ≥50 | PLS No. 1 | IV | TBD | 5 mg/kg |
| 4 | ≥25 | ≥50 | PLS No. 2 | IV | TBD | 5 mg/kg |

This is a randomized, non-masked, GCP field safety study conducted in young, healthy, purpose-bred dogs. This study is 16 days in length at each study site. At least 100 minimum age dogs (≤10 weeks of age) of any gender, and at least 200 dogs older than the minimum age (>10 weeks of age) of any gender, are enrolled into the study.

Exclusion criteria. The dog:
Is currently enrolled in another study.
Has been enrolled in another study within the previous 30 days.
Has received chimeric biologics ≤90 days prior to Day −2.
Is not cooperative for study procedures.
Is not reasonably expected to survive the duration of the study.
Has any pre-existing skin conditions which may confound ISOs.
Has current medical history suggesting a significant comorbidity (e.g., polyuria, polydipsia, polyphagia, vomiting or diarrhea, unexplained weight loss, etc.).

The minimum age dogs are located in one site (Ridglan Farms (Mount Horeb, WI)) whereas the remaining dogs are divided among Test Facilities in three geographic regions. A minimum of three Test Facilities located in three separate geographical regions and unique breeding colonies to diversify genetics as much as possible are used. At each site, dogs are randomized 1:1:1:1 to Groups 1, 2, 3 and 4 as per Table 20.

On Day 0, all dogs are administered Mab A v2 either SC or IV. Two different pre-licensing serials (PLS) of Mab A v2 are administered in this study. Within each age group and treatment method group, approximately half of the dogs randomly receive PLS No. 1 and the other half randomly receive PLS No. 2.

Randomization. Due to challenges with finding Test Facilities with appropriately aged dogs, the approximately 100 minimum age dogs is sourced from one location. Approximately 200 remaining dogs are divided among Test Facilities in at least three geographic regions and are divided as evenly as possible amongst the Test Facilities. Randomization is stratified by the Test Facility site into blocks containing four dogs. Within each site, dogs are randomized at a 1:1:1:1 ratio to Groups 1 (PLS No. 1, SC), 2 (PLS No. 2, SC), 3 (PLS No. 1, IV), and 4 (PLS No. 2, IV). The randomization is based on random numbers generated by the PLAN procedure in SAS (SAS Institute, Cary NC, version 9.4 or later) using the randomized selection method with a seed number.

Acclimation. This study is conducted in Test Facilities where the dogs are previously acclimated to diet, housing, handling procedures, etc. Therefore, only a 2 day acclimation phase is implemented to ensure dogs meet the enrollment criteria and to clip the injection sites on Day −2.

Physical Examination (PE). A PE is performed by on site veterinarian on Days −2, 0 (pre-dose), 7, and 14. PEs include a subjective assessment of general appearance and attitude, otic, ocular, oral, mucous membranes, respiratory, cardiovascular, gastrointestinal, neurologic, musculoskeletal, integumentary and genitourinary. VeDDRA low level terminology is utilized to describe specific PE abnormalities. Abnormalities (excluding pre-existing conditions and worsening abnormalities) recorded after Day 0 are considered as AEs.

Injection Site Observations (ISO). On Day −2 the injection site is clipped in preparation for dosing on Day 0. Prior to treatment, the clipped injection site is evaluated and recorded as free of any inflammation or clipper burn. Beginning on Day 0 through Day 14, the injection site location is evaluated once daily for local injection site reactions including but not limited to erythema, heat, swelling (e.g. nodule). The size of any reactions is recorded. Any injection site reaction observed is recorded as an AE.

General Health Observations (GHOs). GHOs re conducted once daily beginning on acclimation through study end with one exception: On Days −2, 0, 7 and 14 when PEs are performed, the PE replaces the GHO. General health observations include, but are not limited to, observations of general physical appearance, abnormalities of food or water consumption, and/or occurrence of vomiting or diarrhea. VeDDRA low level terminology is utilized to describe specific observations. The condition of all dogs, including those without abnormal signs, is documented.

Body weights. On Day 0, BW (recorded in kilograms (kg)) is measured using a calibrated scale and recorded. Dogs may be weighed fed or fasted. Body weights are documented.

Safety Population. The safety population consists of all dogs who receive Mab A v2.

Safety Outcomes. Safety evaluation is through collation of all AEs. Specifically, dogs are monitored for injection site reactions such as erythema, heat or swelling (via daily ISO) and systemic reactions, including anaphylaxis post administration of Mab A v2. The AE data are not statistically analyzed but are summarized and tabulated.

Adverse Events (AE). An AE is defined as any observation in dogs that is unfavorable, unexpected, and unintended, and occurs after the use of a veterinary product, whether or not considered to be product related. All AEs are documented and recorded using low level VEDDRA terms.

Serious AE. An AE that is fatal or life-threatening or requires professional intervention (e.g., the dog's health is such that the Investigator determines that the dog should either be euthanized or receive medical treatment).

Non-Serious AE. An AE that is not severe enough to require professional intervention or removal of the dog from the study.

See the schedule of events in Table 21 below.

TABLE 21

| Event | Day −2 | Day 0 | Days 1-6 | Day 7 | Days 8-13 | Day 14 | Unscheduled |
|---|---|---|---|---|---|---|---|
| Clip Hair Over Injection Site | √ | | | | | | |
| Inclusion/Exclusion Criteria | √ | | | | | | |
| Signalment | √ | | | | | | |
| Physical Exam with Body Weight | √ | √ | | √ | | √ | √ |
| Mab A v2 Administration | | √ | | | | | |
| General Health Observations (GHOs)* | | | √ | | √ | | |
| Injection Site Observation (ISO)** | | √ | √ | √ | √ | √ | √ |
| Record Adverse Events | | √ | √ | √ | √ | √ | √ |
| Study Exit | | | | | | √ | √ |

*GHOs include, but are not limited to, observations of general physical appearance, abnormalities of food or water consumption, and/or occurrence of vomiting or diarrhea.
*The injection site is evaluated once daily from Days 0 to 14 for clinical signs of local inflammation (including but not limited to erythema, heat, swelling, nodules). Size of reactions are recorded.

Example 15

Figure 5:
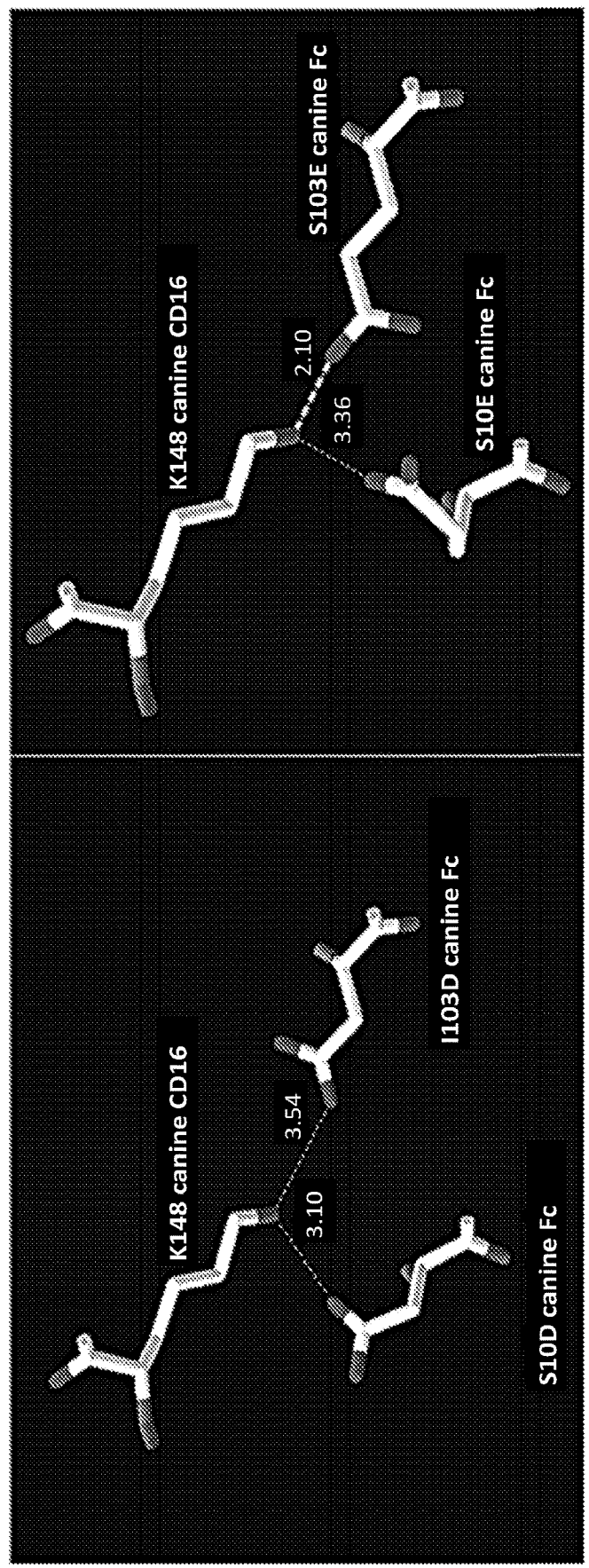
FIG. 5 shows structural models of variant canine IgG-B Fc polypeptide sequences of Example 15 and canine CD16.

Identification of Variant Canine IgG-B Fc Polypeptides for Enhanced ADCC Activity Structural models of canine CD16 and canine IgG-B Fc were prepared using the structural coordinates of human IgG1 Fc/CD16 complex (1e4k1.pdb) as template. See Sondermann P., "The 3.2-A Crystal Structure of the Human IgG1 Fc Fragment-Fc gammaRIII complex," Nature 406 (6793):267-73 (2000). Amino acid residues that appear to interact between wild-type canine IgG-B Fc (SEQ ID NO: 91) and canine CD16 (SEQ ID NO: 90) were identified. Both Ser10 and Ile103 of canine IgG-B Fc SEQ ID NO: 91 are in close proximity to Lys148 of canine CD16 SEQ ID NO: 90. To gain electrostatic interaction, Ser10 and/or Ile103 of canine IgG-B Fc SEQ ID NO: 90 may be substituted with acidic amino acids Asp or Glu to introduce a salt bridge to K148 of canine CD16 SEQ ID NO: 90. The distance between Ser10Asp and Lys148; between Ser10Glu and Lys148; between Ile103Asp and Lys148; and between Ile103Glu and Lys148 are each less than 4 Å (FIG. 5). Exemplary variant canine IgG-B Fc polypeptide sequences for enhanced ADCC activity include SEQ ID NO: 92, SEQ ID NO: 93, SEQ ID NO: 94, SEQ ID NO: 95, SEQ ID NO: 96, SEQ ID NO: 97, SEQ ID NO: 98, and SEQ ID NO: 99. Such variant canine IgG-B Fc polypeptides may be used to in place of wild-type canine IgG-B Fc to enhance the killing of parvovirus infected cells.

REFERENCES

1. S. Nandi, Manoj Kumar. Canine Parvovirus: Current Perspective. Indian J. Virol. 2010; 21(1):31-44.
2. Carla Miranda, Gertrude Thompson. Canine parvovirus: the worldwide occurrence of antigenic variants. Journal of General Virology. 2016; 97, 2043-2057.
3. Melissa Kennedy, Adesola Odunayo. Canine Parvovirus. Clinician's Brief. 2017.
4. Brindhalakshmi B, Mukhopadhyay H K, Antony P X, Thanislass J, Vijayalakshmi P, Mangadevi N. Isolation and molecular characterization of canine and feline parvovirus strains—an updated review. Journal of Dairy, Veterinary & Animal Research. 2016; 3(5):164-169.
5. Emilee Venn, Karolina Preisner, Pedro Boscan, David Twedt, Lauren A. Sullivan. Evaluation of an outpatient protocol in the treatment of canine parvoviral enteritis. Journal of Veterinary Emergency and Critical Care. 2017; 27(1):52-65.

The invention claimed is:

1. An antibody that binds to canine parvovirus and/or feline parvovirus, wherein the antibody comprises:
    (a) (i) a CDR-H1 comprising the amino acid sequence of SEQ ID NO: 4,
        (ii) a CDR-H2 comprising the amino acid sequence of SEQ ID NO: 5,
        (iii) a CDR-H3 comprising the amino acid sequence of SEQ ID NO: 6, and
    (b) (i) a CDR-L1 comprising the amino acid sequence of SEQ ID NO: 13,
        (ii) a CDR-L2 comprising the amino acid sequence of SEQ ID NO: 14,
        (iii) a CDR-L3 comprising the amino acid sequence of SEQ ID NO: 15, and
    wherein the heavy chain sequence is at least 95% identical to SEQ ID NO: 24 and the light chain sequence is at least 95% identical to SEQ ID NO: 25.

2. The antibody of claim 1, wherein the heavy chain sequence is at least 98% identical to SEQ ID NO: 24 and the light chain sequence is at least 98% identical to SEQ ID NO: 25.

3. The antibody of claim 1, wherein the heavy chain sequence is at least 99% identical to SEQ ID NO: 24 and the light chain sequence is at least 99% identical to SEQ ID NO: 25.

4. The antibody of claim 1, wherein said antibody is isolated.

5. The antibody of claim 1, wherein said antibody is a chimeric antibody.

6. The antibody of claim 1, wherein the antibody binds to an epitope comprising the amino acid sequence of SEQ ID NO: 1, SEQ ID NO: 2, and/or SEQ ID NO: 3.

7. The antibody of claim 1, wherein the antibody binds to canine parvovirus or feline parvovirus as determined by immunoblot analysis and/or biolayer interferometry.

8. The antibody of claim 1, wherein the antibody at a concentration of 200 µg/mL has an hemagglutination inhibition value of at least 8000, of at least 16000, or of at least 32000.

9. The antibody of claim 1, wherein the antibody is a monoclonal antibody.

10. An isolated nucleic acid encoding the antibody of claim 1.

11. A host cell comprising the nucleic acid of claim 10.

12. A method of producing an antibody comprising culturing the host cell of claim 11 and isolating the antibody.

13. A pharmaceutical composition comprising the antibody of claim 1 and a pharmaceutically acceptable carrier.

14. The pharmaceutical composition of claim 13, wherein the pharmaceutically acceptable carrier is phosphate buffered saline.

15. A method of providing passive immunity in a canine or a feline subject against infection with a canine or feline parvovirus comprising administering to the subject a therapeutically effective amount of the antibody of claim 1 that binds to the canine or feline parvovirus.

16. The method of claim 15, wherein the antibody is administered before or after exposure to the canine or feline parvovirus or after infection with the canine or feline parvovirus.

17. The method of claim 16, wherein the antibody is administered after the subject has exhibited at least one symptoms selected from the group consisting of fever, vomiting, diarrhea, lymphopenia, and septicemia.

18. An antibody that binds to canine parvovirus and/or feline parvovirus, wherein the antibody comprises:
    (a) (i) a CDR-H1 comprising the amino acid sequence of SEQ ID NO: 4,
        (ii) a CDR-H2 comprising the amino acid sequence of SEQ ID NO: 5,
        (iii) a CDR-H3 comprising the amino acid sequence of SEQ ID NO: 6, and
    (b) (i) a CDR-L1 comprising the amino acid sequence of SEQ ID NO: 13,
        (ii) a CDR-L2 comprising the amino acid sequence of SEQ ID NO: 14,
        (iii) a CDR-L3 comprising the amino acid sequence of SEQ ID NO: 15, and
    wherein the heavy chain sequence comprises SEQ ID NO: 24 with optionally 1, 2, 3, 4, or 5 amino acid substitutions and the light chain sequence comprises SEQ ID NO: 25 with optionally 1, 2, 3, 4, or 5 amino acid substitutions.

19. The antibody of claim 18, wherein said amino acid substitutions are conservative substitutions.

20. A method of treating a canine or feline parvoviral infection in a canine or a feline subject comprising administering to the subject a therapeutically effective amount of the antibody of claim 1 that binds to the canine or feline parvovirus.

21. A method for detecting a parvoviral infection in a sample from a canine or a feline subject comprising contacting the sample with the antibody of claim 1 under conditions permissive for the binding of the antibody to a parvovirus, and detecting whether a complex is formed between the antibody and the parvovirus in the sample.

22. A variant IgG Fc polypeptide comprising:
a) an aspartic acid or a glutamic acid at a position corresponding to position 10 of SEQ ID NO: 91;
b) an aspartic acid or a glutamic acid at position 10 of SEQ ID NO: 91;
c) an aspartic acid or a glutamic acid at a position corresponding to position 103 of SEQ ID NO: 91;
d) an aspartic acid or a glutamic acid at position 103 of SEQ ID NO: 91;
e) an aspartic acid or a glutamic acid at a position corresponding to position 10 and/or position 103 of SEQ ID NO: 91; or
f) an aspartic acid or a glutamic acid at position 10 and/or position 103 of SEQ ID NO: 91.

23. The antibody of claim 1, wherein the heavy chain comprises a variable heavy chain framework region (HC-FR1) comprising the amino acid sequence of SEQ ID NO: 8.

24. The antibody of claim 2, wherein the heavy chain comprises a HC-FR1 comprising the amino acid sequence of SEQ ID NO: 8.

25. The antibody of claim 19, wherein the heavy chain comprises a HC-FR1 comprising the amino acid sequence of SEQ ID NO: 8.

26. The antibody of claim 18, wherein the antibody comprises:
(a) (i) a CDR-H1 comprising the amino acid sequence of SEQ ID NO: 4,
(ii) a CDR-H2 comprising the amino acid sequence of SEQ ID NO: 5,
(iii) a CDR-H3 comprising the amino acid sequence of SEQ ID NO: 6, and
(b) (i) a CDR-L1 comprising the amino acid sequence of SEQ ID NO: 13,
(ii) a CDR-L2 comprising the amino acid sequence of SEQ ID NO: 14,
(iii) a CDR-L3 comprising the amino acid sequence of SEQ ID NO: 15, and
wherein the heavy chain sequence comprises SEQ ID NO: 24 and the light chain sequence comprises SEQ ID NO: 25.

27. The antibody of claim 1, wherein the antibody binds to canine parvovirus.

28. The antibody of claim 19, wherein the antibody binds to canine parvovirus.

* * * * *